(12) United States Patent
Hahn et al.

(10) Patent No.: US 8,637,260 B2
(45) Date of Patent: Jan. 28, 2014

(54) PHOSPHORYLATED RAIA

(75) Inventors: William C. Hahn, Newton, MA (US); Laura Corral, San Francisco, CA (US); Anna A. Sablina, Kessel-lo (BE)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/108,951

(22) Filed: May 16, 2011

(65) Prior Publication Data

US 2011/0306057 A1    Dec. 15, 2011

Related U.S. Application Data

(63) Continuation of application No. 12/599,826, filed as application No. PCT/US2008/006177 on May 14, 2008, now abandoned.

(60) Provisional application No. 60/917,745, filed on May 14, 2007.

(51) Int. Cl.
*C12Q 1/00* (2006.01)
*G01N 33/53* (2006.01)
*G01N 33/567* (2006.01)
*G01N 33/574* (2006.01)

(52) U.S. Cl.
USPC .............. 435/7.1; 435/4; 435/6.14; 435/7.21; 435/7.23; 435/7.92

(58) Field of Classification Search
USPC ................... 435/4, 6.14, 7.1, 7.21, 7.23, 7.92
See application file for complete search history.

(56) References Cited

U.S. PATENT DOCUMENTS 7,991,557 B2 * 8/2011 Liew et al. ................... 702/19
2004/0033495 A1 * 2/2004 Murray et al. ................. 435/6

* cited by examiner

*Primary Examiner* — Alana Harris Dent
(74) *Attorney, Agent, or Firm* — Fish & Richardson P.C.

(57) ABSTRACT

Antibodies that are specific for human Ra1A that is phosphorylated at one or both of Ser183 and Ser194 are described as various methods such antibodies, including diagnostic methods and screening methods.

6 Claims, 27 Drawing Sheets

List of proteins found associated with PP2A Aα and Aβ subunits.

| Aα | Aβ |
|---|---|
| Striatin | Striatin |
| SG2NA | SG2NA |
| B55α | B55α |
| Cα | B56ε |
|  | Cα |
| MCM3 | |
| CDC2 | |
| Prdx1,2 | |
| DJ-1 | |
| Rabs 18, 7, 11 | |
| CH 60 | |
| EF2 | |
| Rap1a | RalA |
| APC10 | CDK4 |
| TNFR-associated | Annexin V |
| domain (TRADD) | FGFR1 oncogene partner |
|  | HDAC1 |
|  | Collagenase stimulating factor |

{ PP2A subunits (top section)

FIG. 6B

IP: FLAG — 293T: Vector, FLAG-Aα, FLAG-Aβ

- FLAG
- SG2NA
- cdc2
- cdk4
- HDAC1
- RalA
- FGFR1-OP

FIG. 6C

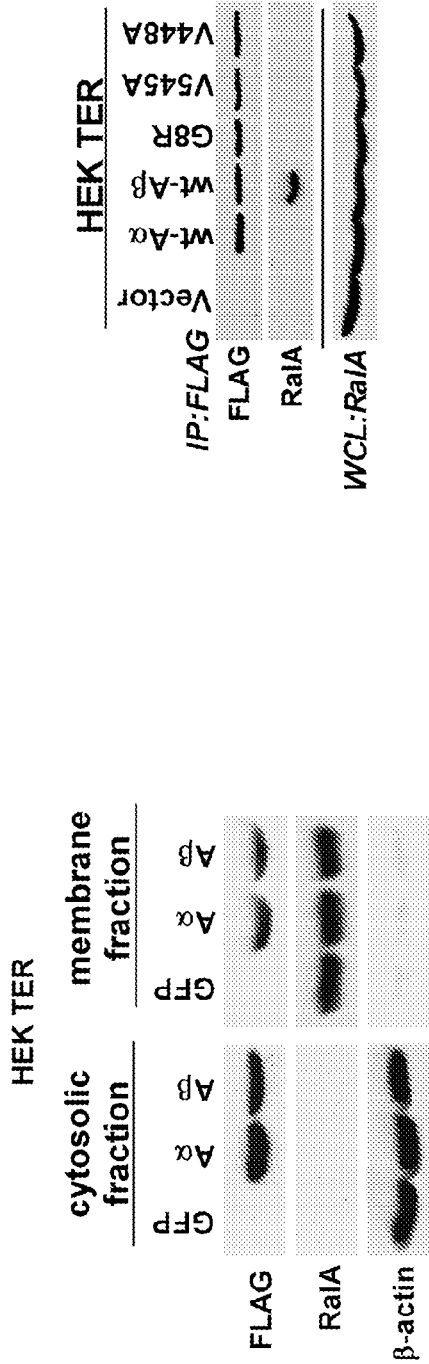
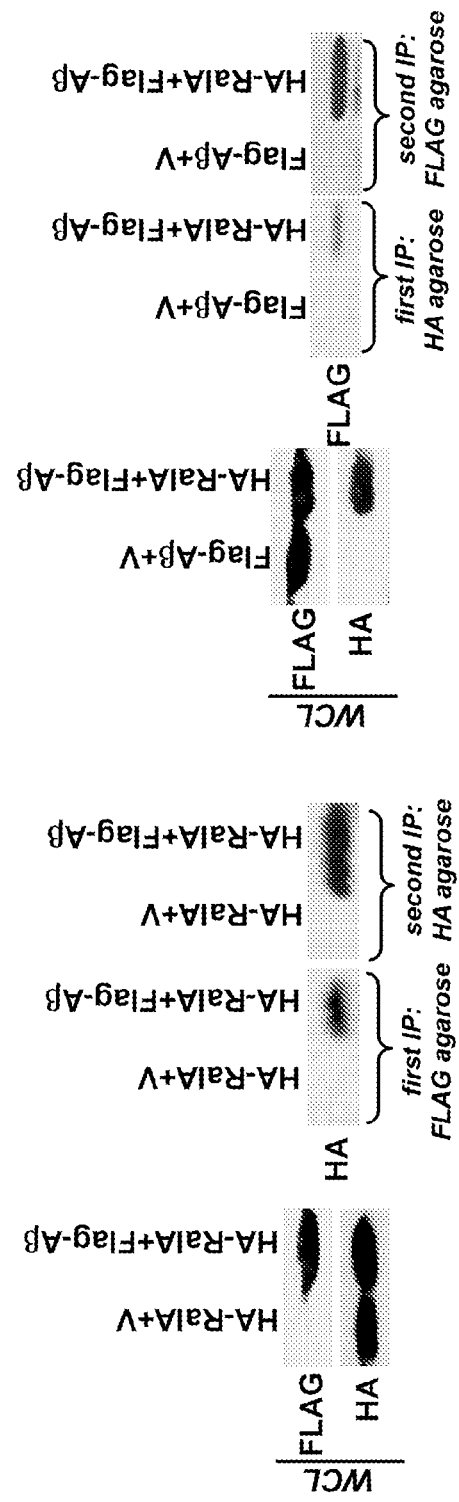

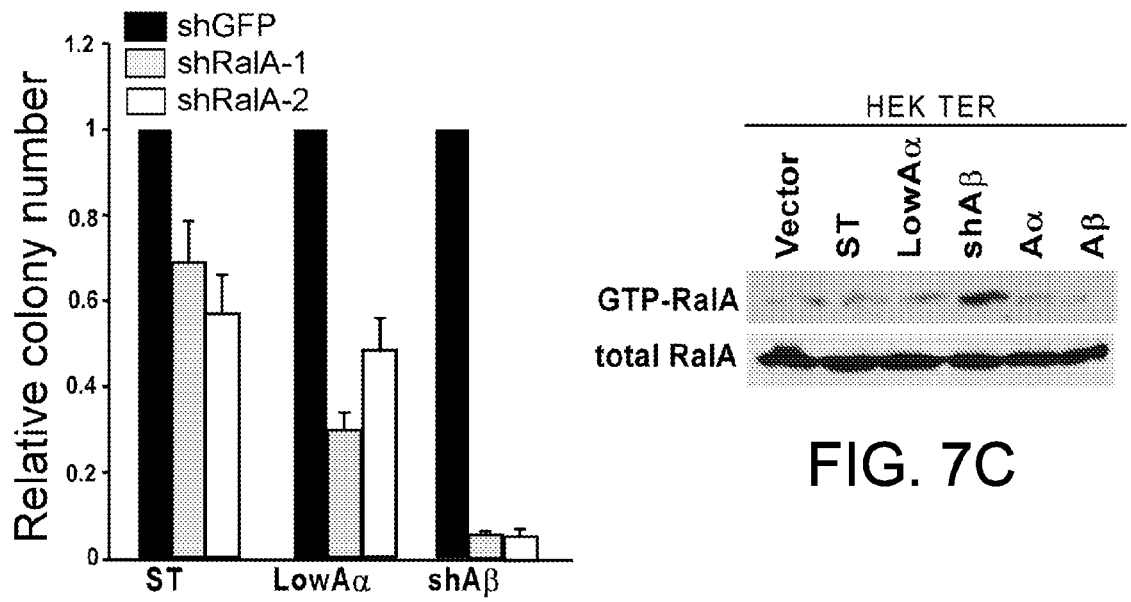
FIG. 7B
FIG. 7C
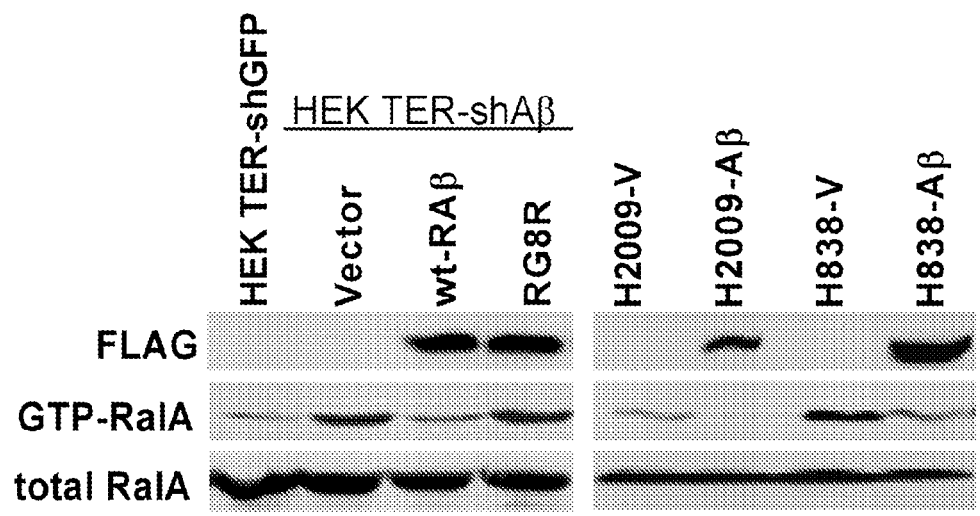
FIG. 7D

SEQ ID NO: 1
PP2A Aα subunit
GenBank Accession No. J02902

```
   1 gaattccggt tctcactctt gacgttgtcc agctccagca ccttggcaac tccccagct
  61 tggacggccg gcccgccgct ccatggggga gtcatctgag cacagctgct ggccgcagtc
 121 tgacaggaaa gggacggagc caagatggcg gcggccgacg cgacgactc gctgtacccc
 181 atcgcggtgc tcatagacga actccgcaat gaggacgttc agcttcgcct caacagcatc
 241 aagaagctgt ccaccatcgc cttggccctt ggggttgaaa ggacccgaag tgagcttctg
 301 cctttcctta cagataccat ctatgatgaa gatgaggtcc tcctggccct ggcagaacag
 361 ctggaacct tcactaccct gytggaggc ccagagtacg tgcactgcct gtgccaccg
 421 ctggagtcgc tggccacagt ggaggagaca gtggtgcggg acaaggcagt ggagtcctta
 481 cgggccatct cacacgagca ctcgccctct gacctggagg cgcactttgt gcgctagtg
 541 aagcggctgg cgggcggcga ctggttcacc tcccgcacct cggctgcgg cctcttctcc
 601 gtctgctacc ccgagtgtc cagtgctgtg aaggcggaac ttgacagta cttccggaac
 661 ctgtgctcag atgacacccc catggtgcgg cgggccgcag cctccaagct gggggagttt
 721 gccaaggtgc tggagctgga caacgtcaag agtgagatca tccccatgtt ctccaacctg
 781 gcctctgacg agcaggactc ggtgcggctg ctggcggtgg aggcgtgcgt gaacatcgcc
 841 cagcttctgc cccaggagga tctggaggcc ctggtgatgc ccactctgcg ccaggccgct
 901 gaagacaagt cctgggccgt ccgctacatg gtggctgaca gttcacaga gtccagaaa
 961 gcagtgggc ctgagatcac caagacagac ctggtccctg ccttccagaa cctgatgaaa
1021 gactgtgagg ccgaggtgag ggccgcagcc tcccacaagg tcaaagagtt ctgtgaaaac
1081 ctctcagctg actgtcggga gatgtgatc atgtcccaga tcttgccctg catcaaggag
1141 ctggtgtccg atgccaacca acatgtcaag tctgccctgg cctcagtcat catgggtctc
1201 tctcccatct tgggcaaaga caacacatc gagcacctct gccctctt cctggctcag
1261 ctgaaggatg agtgccctga ggtacggctg aacatcatct ctaacctgga ctgtgtgaac
1321 gaggtgattg catccggca gctgtcccag tcctgctcc ctgccattgt ggagctggct
1381 gaggacgcca gtggcgggt gcggctggcc atcattgagt acatgccct cctggctgga
1441 cagctggagg tggagttctt tgatgagaaa cttaactcct tgtgcatggc ctggcttgtg
1501 gatcatgtat atgccatccg cgaggcagcc accagcaacc tgaagaagct agtggaaaag
1561 tttgggaagg agtgggccca tgccacaatc atccccaagg tcttggccat gtccggagac
1621 cccaactacc tgcaccgcat gactacgtc ttctgcatca atgtgctgtc tgaggtctgt
1681 gggcaggaca tcaccaccaa gcacatgcta cccacggttc tgcgcatggc tgggaccccg
1741 gttgccaatg tccgcttcaa tgtggccaag tctctgcaga gatagggcc catcctggac
1801 aacagcacct tgcagagtga agtcaagccc atcctagaga agctgaccca ggaccaggat
1861 gtggacgtca aatacttgc ccaggaggct ctgactgttc tgtctctcgc tgatgctgg
1921 aagaggagca aacactggcc tctggtgtcc ccctccaac ccccacaagt ccctctttgg
1981 ggagacactg gggggccttt ggctgtcact ccctgtgcat ggtctgaccc caggcccctt
2041 cccccagcac ggttcctcct ctcccagcc tggaagatg tctcactgtc cacctcccaa
2101 cggctagggg agcacggggt tggacaggac agtgaccttg ggaggaaggg gctactccgc
2161 catccttaaa agccatggag ccggaggtgg caattcaccg aattc
```

FIG. 11-1

SEQ ID NO: 2
PP2A Aβ subunit
GenBank Accession No. AF087438

```
   1 gggtgaccag cagcaggagg agaaagaaca tggcgggcgc atcagagctc gggaccggcc
  61 caggagcagc gggtggagat ggagatgatt cgctataccc gatcgcggtt ttaatcgacg
 121 agctccgcaa tgaagacgtg cagctccgac tcaacagtat taagaagtta tcaacaattg
 181 ccctagcact tggagtagaa aggacccgaa gtgaattgtt gccatttctt acagatacaa
 241 tttatgatga acatgaggta ctattagctc ttgctgagca gctgggaaat ttcactggcc
 301 tagtgggagg tcctgacttt gcccactgtc tgctgcctcc tttggaaaat ctggcaactg
 361 tggaagagac tgttgttcgt gacaaggctg tggagtccct gagacagatc tcccaggagc
 421 atactcctgt tgctctggaa gcttattttg tacctctggt gaaacgctta gcaagtgggg
 481 attggttcac ctctcgcaca tctgcatgtg gtttgttcag cgtttgctat cccagggcat
 541 caaatgctgt taaagcagaa atcagacagc aattccgttc ctgtgctca gatgacacac
 601 caatggtacg acgtgctgct gcttccaaat tgggtgaatt tgcaaagtt ttggaattag
 661 acagtgtgaa aagtgaaatt gttccactgt tcactagtct agcttcagat gaacaggatt
 721 cagtgcgcct ccttgctgtg gaagcttgtg tcagtattgc ccagttattg tctcaggatg
 781 accttgagac tttggtgatg cctacacttc gacaagcagc agaagataaa tcttggcgcg
 841 ttcgctatat ggtggctgac agatttcag agctccagaa agccatgggt cctaaaatca
 901 ccctaaatga cctcatcccc gcctttcaga acctacttaa agactgtgaa gctgaagtcc
 961 gggcagctgc tgcccacaaa gtaaaagaac ttggtgagaa cttgcccatt gaagatagag
1021 agaccataat tatgaatcaa attctgcctt atataaagga attagtatcc gataccaatc
1081 aacatgtcaa atcggctcta gcttctgtaa ttatgggatt gtctactatt ttgggcaaag
1141 aaaataccat tgaacatctt ctacctcttt tcttagctca gttaaaggat gagtgtcctg
1201 acgttcgttt gaatatcatc tccaatttgg attgtgtaaa tgaagtgatt ggaatccgtc
1261 agctctctca gtctctcctt cctgccatag tggagctggc agaagatgcc aaatggaggg
1321 tccgcctggc catcattgag tatatgccgc tgctggcagg ccagctgggt gtggaattct
1381 ttgatgaaaa gctgaattct ttatgtatgg cttggctcgt ggaccatgta tacgccatcc
1441 gagaagctgc caccaacaac ctcatgaaac tagttcagaa gtttggtaca gagtgggccc
1501 aaaatactat tgttcccaaa gtgttagtaa tggcaaatga tcctaattac ttgcatagaa
1561 tgaccacttt attctgcatt aatgcactgt ctgaggcctg tggtcaggaa ataactacta
1621 agcaaatgct gcccatcgta ttaaaaatgg caggagacca agtagcaaat gttcgcttca
1681 atgtggccaa atctctacaa aagattggac caattctaga taccaatgct ttacaggagg
1741 aagtgaagcc agtactacag aagttaggtc aagatgaaga catggatgtc aaatactttg
1801 cacaggaagc tataagtgtt cttgcattgg cataatgagg agcaggaggg aaaaggcctt
1861 tactagattc ttgtcacaaa tttctagtca atgtgttctt aactgggtgg agaaagaatg
1921 ga
```

FIG. 11-2

SEQ ID NO: 8
GenBank Accession No. NP_006237
  1 mssapttpps vdkvdgfsrk svrkarqkrs qsssqfrsgg kpieltplpl lkdvpsseqp
 61 elfikkiggc cvifdfmdti sdlkmkeykr stlnelvdyi tisrgciteq typevvrnvs
121 cnifrtipps dsnefdpeed eptleaswph lqlvyeffir flesqefqps iakkyidqkf
181 vlqileifds edprerdylk tvlhriygkf lglrafirkq innifirfvy etehfngvae
241 lleilgsiin gfaiplkaeh kqflvkvlip lhtvrslslf haqlaycivq flekdpslte
301 pvirglmkfw pktcsqkevm figeleeild viepsqfvki qeplfkqiak cvssphfqva
361 eralyywnne yimslieens nvilpimfss lyriskehwn paivaivynv ikafmemnst
421 mfdeltatyk sdrqrekkke kereelwkkl edielkrglr rdgiipt SEQ ID NO: 9
GenBank Accession No. NM_005402
RalA MAANKPKGQN SLALHKVIMV GSGGVGKSAL TLQFMYDEFV EDYEPTKADS YRKKVVLDGE EVQIDILDTA
GQEDYAAIRD NYFRSGEGFL CVFSITEMES FAATADFREQ ILRVKEDENV PFLLVGNKSD LEDKRQVSVE
EAKNRAEQWN VNYVETSAKT RANVDKVFFD LMREIRARKM EDSKEKNGKK KRKSLAKRIR ERCCIL

SEQ ID NO:10
GenBank Accession No. NM_005402
RalA nucleotide sequence
```
   1 aagtgatctg tggcggctgc tgcagagccg ccaggaggag ggtggatctc cccagagcaa
  61 agcgtcggag tcctcctcct cctcctcctc ctcctcctcc tcctcctcca gccgcccagg
 121 ctccccgcc acccgtcaga ctcctcctte gaccgctccc ggcgcggggc cttccaggcg
 181 acaaggaccg agtaccctcc ggccggagcc acgcagccgc ggcttccgga gccctggggg
 241 cggcggactg gctcgcggtg cagattcttc ttaatccttt ggtgaaaact gagacacaaa
 301 atggctgcaa ataagcccaa gggtcagaat tctttggctt tacacaaagt catcatggtg
 361 ggcagtggtg gcgtgggcaa gtcagctctg actctacagt tcatgtacga tgagtttgtg
 421 gaggactatg agcctaccaa agcagacagc tatcggaaga aggtagtgct agatggggag
 481 gaagtccaga tcgatatctt agatacagct gggcaggagg actacgctgc aattagagac
 541 aactacttcc gaagtgggga gggggttcctc tgtgttttct ctattacaga aatggaatcc
 601 tttgcagcta cagctgactt cagggagcag attttaagag taaaagaaga tgagaatgtt
 661 ccatttctac tggttggtaa caaatcagat ttagaagata aagacaggt ttctgtagaa
 721 gaggcaaaaa acagagctga gcagtggaat gttaactacg tggaaacatc tgctaaaaca
 781 cgagctaatg ttgacaaggt attttttgat taatgagag aaattcgagc gagaaagatg
 841 gaagacagca agaaaagaa tgaaaaaaag aagaggaaaa gttagccaa gagaatcaga
 901 gaaagatgct gcattttata atcaaagcc aaactccttt cttatcttga ccatactaat
 961 aaatataatt tataagcatt gccattgaag gcttaattga ctgaaattac tttaacattt
1021 tggaaattgt tgtatatcac taaaagcatg aattggaact gcaatgaaag tcaaatttac
1081 tttaaaaaga aattaatatg gcttcaccaa gaagcaaagt tcaacttatt tcataattgc
1141 ctacatttat catggtcctg aatgtagcgt gtaagcttgt gtttcttggg cagtctttct
1201 tgaaattgaa gaggtgaaat gggggtgggg agtgggagga aaggtgactt cctctggtgt
1261 ttattataaa gcttaaattt tatatcattt taaaatgtct tggtcttcta ctgccttgaa
1321 aaatgacaat tgtgaacatg atagttaaac taccactttt tttaaccatt attatgcaaa
1381 atttagaaga aaagttattg gcatggttgt tgcatatagt taaactgaga gtaattcatc
1441 tgtgaatctg ctttaattac ctggtgagta acttagaaaa gtggtgtaaa cttgtacatg
1501 gaatttttg aatatgcctt aatttagaaa ctgaaaaata tctggtata tcattctggg
1561 tgtgttctta ctgacaccag gggtccgctg cccatgtgt ctggtgaga aaatatatgc
1621 ctgcacagc ttttgtatag aaaattcttg agaagtaact gtccgctaga agtctgtcca
1681 aatttaaaat gtgtgccata ttctggttct tgaaaataag attccagagc tctttgatcg
1741 cttttaataa actgcaagtt catttttaaat gaagggcag catatatact tgcaagataa
1801 ttttcagctg caaggattca gcaccagtta tgtttgaatg aaccctcctt ttctctgaga
1861 ttctggtccc tggaaatccc tttctgctag tggtgagcat gtaagtgtta agttttttaat
1921 ctggagcag ggcataggaa gaaaatgtca gtagtgctaa tgcattttgc actagaacgc
1981 ttcgggaaaa tattcatgct tgccatctgt tcattctaa atttatattc ataaagttac
2041 agtttgatac aggaattatt aggagtaatt cttttctgtt tctgtttata atgaagaaca
2101 ctgtagctac atttcagaa gttaacatca agccatcaaa cctgggtata gtcagaaaa
2161 cgtggcacac actgaccaca cattaggctg tgtcaccatt gtgtggtgta cctgctggaa
2221 gaattctagc atgctacttg gggacataat ttcagtggga aatatgccac tgaccgattt
2281 ttttttttc ctcttgcag tggggctagg acagttgatt caacaaagta ttttttcttt
2341 tttctcagt cctaattga acaggtcaaa gatgtgttca ggcattccag gtaacaggtg
2401 tgtatgtaaa gttaaaata ggcttttag gaactcactc tttagatatt tacatccagc
2461 ttctcatgtt aaatatttgt cctaaaggg tttgagatgt acatctttca tttcgtattt
2521 ctcataggct atgccatgtg cggaattcaa gttaccaatg taacactggc cagcgggccc
2581 agcaatctcc atgtgtactt attacagtct tatttaacca ggggtcctaa ccactaacat
2641 tgtgactttg ctttgagacc tttcctctcc tgggtactga ggtgctatga agccaactga
2701 caaagatgca taacgtgtct taggctgatg ccactacccg atttgtttat ttgcaatttg
2761 agccatttaa agaccaataa acttcctttt taaaaaaaa aaaaaaaaaa aaaaaaa
```

PHOSPHORYLATED RALA

This application is a continuation of U.S. patent application Ser. No. 12/599,826, filed on Nov. 11, 2009, which is the National Stage of International Application No. PCT/US2008/006177, filed May 14, 2008, which claims priority to and U.S. Provisional Patent Application Ser. No. 60/917,745, filed on May 14, 2007. The contents of each of these applications are hereby incorporated by reference in their entireties.

TECHNICAL FIELD

This disclosure relates to cancer diagnostics, and more particularly to immunoglobulins, antibodies and aptamers that may be used to diagnose cancer and/or monitor the progression of cancer and/or the response of cancer to therapy in a subject. More specifically, the present disclosure is concerned with immunoglobulins, antibodies and aptamers that may be used to predict cancer and/or monitor the progression of cancer and/or response of cancer to therapy in a subject suspected of having a cancer associated with PP2A.

This disclosure relates to cancer diagnostics, and more particularly to phosphor-serine specific immunoglobulins, antibodies and aptamers that bind to the PP2A substrate, RalA and are useful in the diagnosis of cancer.

BACKGROUND

The causal association between inappropriate protein kinase activation and cancer is well established, and several protein kinase oncogenes have been identified (Broach and Levine, *Current Opin. Genet. Dev.*, 25:6464-6474, 1997; Hanahan and Weinberg, *Cell*, 100:57-70, 2000). On the other hand, the role of protein phosphatases in cancer development has been under investigated and is less well understood.

The PP2A family is a diverse group of ubiquitously expressed serine-threonine phosphatases that have been causally linked to cancer development. Somatic mutations of the PP2A structural Aβ subunit have been observed in 8-15% of colon cancers, 15% of lung cancers, 13% of breast cancers, and 6% of tumor cell lines (Calin et al., *Oncogene*, 19:1191-1195, 2000; Ruediger et al., *Oncogene*, 20:1892-1899, 2001; Takagi et al., *Gut*, 47:268-271, 2000; Tamaki et al., *Oncol. Rep.*, 11:655-659, 2004; Wang et al., *Science*, 282:284-287, 1998). Furthermore, deletions of the PP2A Aβ gene and reduced expression of the PP2A Aβ subunit has been reported in 16 of 32 cancer cell lines derived from human lung, colon, breast, and cervical carcinomas (Baysal et al., Eur. J. Hum. Genet., 9:121-129, 2001; Zhou et al., *Biochem. J.*, 369:387-398, 2003). Despite recent advances in the search for cancer therapies, there still remains no truly effective treatment. While the examples above point to a clear association between the PP2A family and cancer, the molecular mechanism involved have not been characterized and its potential for cancer therapy not investigated.

RalA is a multifunctional protein, regulating membrane transport, apoptosis, transcription, cell migration and cell proliferation (Camionis, J. H., and White, M. A., *Trends Cell Biol.*, 115:327-332, 2005; Feig, L. A., Trends Cell Biol., 13:419-425, 2003). RalA activation results in activation of several signaling pathways, including the activation of phospholipase D1 and Src kinase (Goi et al., *Embo. J.*, 19:623-630, 2000; Jiang et al., *Nature*, 378:409-412, 1995), vesicle transport (Moskalenko et al., *Nat. Cell. Biol.*, 4:66-72, 2002), filopodia formation (Ohta et al., *Proc. Natl. Acad. Sci.*, 96:2122-2128, 1999), epidermal growth factor-induced cell motility (Gildea et al., *Cancer Res.*, 62:982-985, 2002) and AI growth (Chien, Y., and White, M., A., *EMBO Rep.*, 4:800-806, 2003; Lim et al., *Cancer Cell.*, 7:533-545, 2005; Panner et al., *Mol. Cell. Biol.*, 2006). The activation of known RalA effector proteins such as RalBP1 or the exocyst has not previously been directly linked to tumorigenesis. However, other signaling molecules regulated by RalA, such as phospholipase D1, Src, JNK, NF-κB and cyclin D, may contribute to cancer progression (Feig, L. A., Trends Cell Biol., 13:419-425, 2003; Lim et al., *Cancer Cell.*, 7:533-545, 2005).

SUMMARY

Described herein is an isolated antibody molecule or antigen binding portion thereof that binds to (i.e., specifically binds to) a polypeptide consisting of SEQ ID NO: 9 (RalA) that is phosphorylated at one or both of Ser183 and Ser194. An antibody that specifically binds to or is specific for a given polypeptide or an epitope on a given polypeptide is one that binds to the given polypeptide or epitope without substantially binding to any other polypeptide or epitope. In various embodiments: the isolated antibody molecule or antigen binding portion thereof does not bind to a polypeptide comprising SEQ. ID NO:9 that is not phosphorylated at Ser183 and is not phosphorylated at Ser194; the isolated antibody molecule or antigen binding portion thereof does not bind to a polypeptide comprising SEQ ID NO:9 that is phosphorylated at Ser183 and is not phosphorylated at Ser194; the isolated antibody molecule or antigen binding portion thereof does not bind to a polypeptide comprising SEQ ID NO:9 that is not phosphorylated at Ser183 and is phosphorylated at Ser194; the isolated antibody molecule or antigen binding portion thereof binds to (i.e., specifically binds to) a polypeptide comprising SEQ ID NO: 9 that is phosphorylated at both Ser183 and Ser194; the antibody molecule or antibody binding portion thereof is a monoclonal antibody; the antibody molecule or antibody binding portion thereof is a polyclonal antibody; the antibody molecule comprises the antibody classes IgA, IgD, IgE, IgG, and IgM; the IgA antibody class comprises the subtypes IgA1 and IgA2; the IgG antibody class comprises the subtypes IgG1, IgG2, IgG2a, IgG2b, IgG3, and IgG4; the antibody molecule or antigen binding portion thereof is a recombinant antibody molecule or antigen binding portion thereof; the antibody molecule or antigen binding portion thereof has a dissociation constant ($K_d$) for the RalA epitope in the range of $10^{-6}$ M to $10^{-12}$ M. (e.g., the $K_d$ is $10^{-7}$ M to $10^{-11}$ M; the $K_d$ is $10^{-8}$ M to $10^{-11}$ M; the $K_d$ is $10^{-9}$ M to $10^{-11}$ M; the $K_d$ is $10^{-10}$ M to $10^{-11}$ M). Also described is a diagnostic composition comprising the antibody molecule or antigen binding portion in a detectibly labeled form.

Described herein is an aptamer (e.g., a peptide or nucleic acid aptamer) that binds to (i.e., specifically binds to) a polypeptide comprising SEQ ID NO: 9 that is phosphorylated at one or both of Ser183 and Ser194. In various embodiments: the aptamer does not bind to a polypeptide comprising SEQ ID NO:9 that is not phosphorylated at Ser183 and is not phosphorylated at Ser194; and the aptamer binds to a polypeptide comprising SEQ ID NO: 9 that is phosphorylated at both Ser183 or Ser194.

Described herein is a method of generating an antibody molecule or antigen binding portion thereof that binds to a polypeptide comprising SEQ ID NO: 9 (RalA) that is phosphorylated at one or both of Ser183 and Ser1941, the method comprising administering to an animal a polypeptide comprising SEQ ID NO:11 and a polypeptide comprising SEQ ID NO:12 including conservative mutations thereof. In various embodiments: the method comprises administering to an animal a polypeptide of SEQ ID NO:11 including conservative mutations thereof; the method comprises administering to an animal a polypeptide of SEQ ID NO:12 including conservative mutations thereof; and the animal is a mammal.

Described herein is a method of validating an antibody molecule or antigen binding portion thereof that binds to a polypeptide comprising SEQ ID NO: 9 (RalA) that is phosphorylated at one or both of Ser183 and Ser194, the method comprising contacting the antibody molecule or antigen binding portion thereof with a polypeptide comprising SEQ ID NO: 9 that is phosphorylated at one or both of Ser183 and Ser194. In certain cases: the method comprises contacting the antibody molecule or antigen binding portion thereof with a polypeptide comprising SEQ ID NO: 9 that is not phosphorylated at either Ser183 or Ser194; the method comprises contacting the aptamer with a polypeptide comprising SEQ ID NO: 9 that is phosphorylated at one or both of Ser183 and Ser194; and the method comprises contacting the aptamer with a polypeptide comprising SEQ ID NO: 9 that is not phosphorylated at either Ser183 or Ser194.

Described herein is a method for detecting the presence of a polypeptide comprising SEQ ID NO: 9 in a subject, wherein the polypeptide is phosphorylated at one or both of Ser183 and Ser194, the method comprising: (a) providing a biological sample; (b) contacting the biological sample with an antibody molecule or antigen binding portion thereof that binds to a polypeptide comprising SEQ ID NO: 9 (RalA) that is phosphorylated at one or both of Ser183 and Ser194; and (c) detecting the presence or absence of RalA or a polypeptide comprising SEQ ID NO: 9 bound to an antibody molecule or antigen binding portion thereof that binds to a polypeptide comprising SEQ ID NO: 9 (RalA) that is phosphorylated at one or both of Ser183 and Ser194.

In certain cases: the subject is a human; the antibody or antigen binding portion thereof binds to a polypeptide comprising SEQ ID NO: 9 is phosphorylated at both Ser183 and Ser194; and the antibody or antigen binding portion thereof is detectably labeled.

Described herein is a method for monitoring the degree of phosphorylation of a polypeptide comprising SEQ ID NO: 9 in a subject undergoing therapy, wherein one or both of Ser183 and Ser194 are phosphorylated, the method comprising: (a) providing a first biological sample taken from a subject at a first time point during or prior to therapy; (b) providing a second biological sample taken from the subject at a second time point after the first time point; (c) contacting each of the first and the second biological samples with an antibody molecule or antigen binding portion thereof that binds to a polypeptide comprising SEQ ID NO: 9 (RalA) that is phosphorylated at one or both of Ser183 and Ser194; (d) detecting the presence or absence of RalA or a polypeptide comprising SEQ ID NO: 9 bound to the antibody molecule or antigen binding portion thereof that binds to a polypeptide comprising SEQ ID NO: 9 (RalA) that is phosphorylated at one or both of Ser183 and Ser194; wherein an equal or lower level of detection of a polypeptide comprising SEQ ID NO: 9 phosphorylated at one or both of Ser183 and Ser194 bound to the antibody or antigen binding portion thereof in the second sample compared to the first sample indicates that therapy is beneficial for the subject.

Described herein is a method for monitoring the degree of phosphorylation of a polypeptide comprising SEQ ID NO: 9 in a subject undergoing therapy, wherein one or both of Ser183 and Ser194 are phosphorylated, the method comprising: (a) providing a first biological sample taken from a subject at a first time point during or prior to therapy; (b) providing a second biological sample taken from the subject at a second time point after the first time point; (c) determining the relative amount of a polypeptide comprising SEQ ID NO: 9 phosphorylated at one or both of Ser183 and Ser194 in the first and second samples; wherein an equal or lower level a polypeptide comprising SEQ ID NO: 9 phosphorylated at one or both of Ser183 and Ser194 in the second sample compared to the first sample indicates that therapy is beneficial for the subject. In various cases: the antibody or antigen binding fragment thereof binds a polypeptide comprising SEQ ID NO: 9 that phosphorylated at both of Ser183 and Ser194; the subject is a human; and the method is performed at intervals until the end of therapy.

Described herein is a method of diagnosing a cancer in a subject, the method comprising detecting the presence of a polypeptide comprising SEQ ID NO:9, wherein the polypeptide comprising SEQ ID NO:9 is phosphorylated at one or both of Ser183 and Ser194, the method comprising: (a) providing a biological sample from a first test subject; (b) contacting the biological samples with an antibody molecule or antigen binding portion thereof that binds to a polypeptide comprising SEQ ID NO: 9 (RalA) that is phosphorylated at one or both of Ser183 and Ser194; (c) measuring the level of a polypeptide comprising SEQ ID NO: 9 bound to the antibody molecule or antigen binding portion thereof that binds to a polypeptide comprising SEQ ID NO: 9 (RalA) that is phosphorylated at one or both of Ser183 and Ser194; wherein an higher level of detection of a polypeptide comprising SEQ ID NO: 9 phosphorylated at one or both of Ser183 and Ser194 bound to the antibody in the sample when compared to a control is diagnostic for cancer.

Described herein is a method of diagnosing a cancer in a subject, the method comprising detecting the presence of a polypeptide comprising SEQ ID NO:9, wherein the polypeptide comprising SEQ ID NO:9 is phosphorylated at one or both of Ser183 and Ser194, the method comprising: (a) providing a biological sample from a first test subject; and (b) measuring the level of a polypeptide comprising SEQ ID NO: 9 that is phosphorylated at one or both of Ser183 and Ser194, wherein an higher level of a polypeptide comprising SEQ ID NO: 9 phosphorylated at one or both of Ser183 and Ser194 in the sample compared to a control is diagnostic for cancer.

Described herein is a method for detecting the presence of a polypeptide comprising SEQ ID NO: 9 in a biological sample, wherein the polypeptide is phosphorylated at one or both of Ser183 and Ser194, the method comprising: (a) providing a biological sample; (b) contacting the biological sample with an antibody molecule or antigen binding portion thereof that binds to a polypeptide comprising SEQ ID NO: 9 (RalA) that is phosphorylated at one or both of Ser183 and Ser194; (c) detecting the presence or absence of a polypeptide comprising SEQ ID NO: 9 bound to an antibody molecule or antigen binding portion thereof that binds to a polypeptide comprising SEQ ID NO: 9 (RalA) that is phosphorylated at one or both of Ser183 and Ser194. In various cases: the antibody molecule or antigen binding portion binds to a polypeptide comprising SEQ ID NO:9 that is phosphorylated at both Ser183 and Ser194; and the biological sample comprises a cultured cell.

Described herein is a method for evaluating a kinase inhibitor, wherein the kinase inhibitor inhibits the phosphorylation of a polypeptide comprising SEQ ID NO:9 at one or both of Ser183 and Ser194, the method comprising: (a) providing a biological sample; (b) contacting the biological sample with a test compound inhibitor; (c) contacting the biological sample with an antibody molecule or antigen binding portion thereof that binds to a polypeptide comprising SEQ ID NO: 9

(RalA) that is phosphorylated at one or both of Ser183 and Ser194; (d) detecting the presence or absence of RalA or a polypeptide comprising SEQ ID NO: 9 bound to the antibody molecule or antigen binding portion thereof that binds to a polypeptide comprising SEQ ID NO: 9 (RalA) that is phosphorylated at one or both of Ser183 and Ser194, wherein a lower level of detection of a polypeptide comprising SEQ ID NO: 9 phosphorylated at one or both of Ser183 and Ser194 bound to the an antibody molecule or antigen binding portion thereof that binds to a polypeptide comprising SEQ ID NO: 9 (RalA) that is phosphorylated at one or both of Ser183 and Ser194 indicates that test compounds is a candidate kinase inhibitor.

Described herein is a method for detecting the presence of a polypeptide comprising SEQ ID NO: 9 in a subject, wherein the polypeptide is phosphorylated at one or both of Ser183 and Ser194, the method comprising: (a) providing a biological sample; (b) contacting the biological sample with the aptamer that binds to a polypeptide comprising SEQ ID NO: 9 (RalA) that is phosphorylated at one or both of Ser183 and Ser194; (c) detecting the presence or absence of a polypeptide comprising SEQ ID NO: 9 bound to the aptamer. In various instances: the antibody molecule or antigen binding portion binds to a polypeptide comprising SEQ ID NO:9 that is phosphorylated at both Ser183 and Ser194; and the subject is a human.

Described herein is a method for monitoring the degree of phosphorylation of a polypeptide comprising SEQ ID NO: 9 in a subject, wherein one or both of Ser183 and Ser194 are phosphorylated, the method comprising: (a) providing a first biological sample taken from a subject at a first time point; (b) providing a second biological sample taken from the subject at a second time point after the first time point; (c) contacting each of the first and the second biological samples with an aptamer that binds to a polypeptide comprising SEQ ID NO: 9 (RalA) that is phosphorylated at one or both of Ser183 and Ser194; (d) detecting the presence or absence of a polypeptide comprising SEQ ID NO: 9 bound to the aptamer; and (e) comparing the level of polypeptide comprising SEQ ID NO:9 bound to the aptamer in the first and second samples.

Described herein is a method of diagnosing a cancer in a subject, the method comprising detecting the presence of a polypeptide comprising SEQ ID NO:9, wherein the polypeptide comprising SEQ ID NO:9 is phosphorylated at one or both of Ser183 and Ser194, the method comprising: (a) providing a first biological sample from a first test subject and a second biological sample from a second healthy subject; (b) contacting each of the first and second biological samples with the aptamer that binds to a polypeptide comprising SEQ ID NO: 9 (RalA) that is phosphorylated at one or both of Ser183 and Ser194; (c) detecting the presence or absence of a polypeptide comprising SEQ ID NO: 9 bound to the aptamer, wherein an higher level of detection of a polypeptide comprising SEQ ID NO: 9 phosphorylated at one or both of Ser183 and Ser194 bound to the aptamer in the first sample when compared to the second sample is diagnostic for cancer.

Described herein is a method for detecting the presence of a polypeptide comprising SEQ ID NO: 9 in a biological sample, wherein the polypeptide is phosphorylated at one or both of Ser183 and Ser194, the method comprising: (a) providing a biological sample; (b) contacting the biological sample with the aptamer that binds to a polypeptide comprising SEQ ID NO: 9 (RalA) that is phosphorylated at one or both of Ser183 and Ser194; (c) detecting the presence or absence of a polypeptide comprising SEQ ID NO: 9 bound to the aptamer. In various instances: the detected polypeptide comprising SEQ ID NO: 9 is phosphorylated at both Ser183 and Ser194; and the in vitro biological sample comprises a cultured cell.

Described herein is a method for evaluating a kinase inhibitor, wherein the kinase inhibitor inhibits the phosphorylation of a polypeptide comprising SEQ ID NO:9 at one or both of Ser183 and Ser194, the method comprising: (a) providing a biological sample; (b) contacting the biological sample with the kinase inhibitor; (c) contacting the biological sample with the aptamer that binds to a polypeptide comprising SEQ ID NO: 9 (RalA) that is phosphorylated at one or both of Ser183 and Ser194; (d) detecting the presence or absence of RalA or a polypeptide comprising SEQ ID NO: 9 bound to the aptamer, wherein a lower level of detection of a polypeptide comprising SEQ ID NO: 9 phosphorylated at one or both of Ser183 and Ser194 bound to the aptamer indicates that the kinase inhibitor is effective.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIGS. 6A-6H are immunoblots showing the interaction of PP2A Aβ with RalA. (A) Coomassie blue staining of a large scale immunoprecipitation of FLAG-tagged Aα or Aβ overexpressed in 293T cells. (B) Mass spectroscopy output showing results from analysis of proteins identified in (A). (C) Immuoblot showing validation of (A). FLAG-tagged PP2A Aα and Aβ were overexpressed in 293T cells and Aα or Aβ-specific complexes were precipitated using anti-FLAG (M2). Immunoblotting was performed using FLAG (M2), SG2NA, cdc2, cdk4, HDAC1, RalA, and FGFR-1 specific antibodies. (D) Immunoblot showing FLAG-tagged Aα or Aβ immunoprecipitation from 293T cells. (E) Immunoblot showing reciprocal immunoprecipitation of FLAG-tagged Aβ and HA-tagged RalA. Constructs were expressed in 293T cells and precipitated using FLAG (M2) or anti-HA (H7) agarose. (F) Immunoblot showing subcellular localization of Aα, Aβ, and RalA. Soluble and membrane fractions were isolated from 293T cells. (G) Immunoblots showing quantitative immunoprecipitations or RalA and Aβ. Constructs were expressed in 293T cells. Immunoprecipitations were performed using anti-HA agarose or anti-FLAG agarose. Immunoprecipitates were subsequently incubated with anti-HA or anti-FLAG agarose in a reciprocal manner. Densitometry analysis was performed using Scion image software. (H) Immunoblot showing the interaction between RalA and cancer-derived Aβ mutants. Anti-FLAG-epitope tag immunoprecipitation from HEK TER cells expressing wtPP2A Aβ or Aβ mutants.

FIGS. 7A-7D are immunoblots and bar graphs showing RalA expression, cell proliferation, AI growth and tumor formation. (A) Immunoblot showing RalA expression in HEK TER cells treated with shRalA (top panel) and bar graph showing cell proliferation of HEK TER cells expressing control vector (V), SV40 ST, low Aα (50% Aα expression), or shAβ, shRalA-1, shRalA-2, or shGFP. Proliferation data is mean±SD for 3 independent experiments. (B) Bar graph showing AI growth of cells described in (A). Number of AI colonies formed is presented as mean±SD for 3 independent experiments. (C and D) Immunoblots showing RalA activity in cell lines treated as described in (A).

FIG. 11 depicts various nucleic acid and polypeptide sequences, including the sequence of RalA polypeptide (SEQ ID NO:9).

DETAILED DESCRIPTION

Figure 1A:
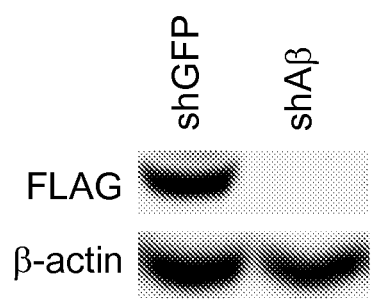
FIGS. 1A-1L show PP2A expression levels assayed by immunoblotting and RT-PCR as well as bar and lines graphs to represent cell proliferation, attachment independent growth, and tumorgenicity. (A) Immunoblot showing FLAG-tagged PP2AAβ expression levels in 293T cells treated with shGFP and shAβ assessed by immunoblotting. (B) Bar graph show in endogenous PP2A Aβ expression levels in HEK TER cells treated with shGFP and shAβ assessed by quantitative RT-PCR. (C) Immunoblot showing PP2A expression levels in HEK TER cells treated with shGFP, shAβ, or shAα assessed by immunoblotting. (D) Bar graph showing PP2A phosphatases activity levels in HEK TER cells treated with shGFP, shAβ, or shAα. (E) Line graph showing proliferation of HEK TER cells treated with shGFP, shAα, shAβ, or SV40 ST. (F) Bar graph showing attachment independent (AI) growth and tumorgenicity of the cells described in E. Tumors are reported as the number of tumors formed per number of injection sites. (G) Bar graph showing AI growth of AATER cells lacking Aβ expression. RA Aβ is an allele of PP2A Aβ resistant to shAβ. (H) Line graph showing HEK TER cells expressing shGFP (n=9), shAα (n=9), shAβ (n=9), and SV40 ST (n=6) were injected subcutaneously and xenograft growth was analyzed biweekly. (I) Immunoblot showing FLAG-tagged PP2A Aβ expression levels in HEK TER cells treated with shAβ-2. (J) Bar graph showing AI growth in HEK TER cells treated with shAβ-2. Data are mean number of colonies in soft agar in cells treated with shGFP, SV40 ST, or shAβ-2 for 3 independent experiments ±SD. (K) shAβ resistant mutant sequence (RAβ) (SEQ ID NOs: 13-15). Silent substitutions were introduced into PP2A Aβ sequence targeted by shAβ. (L) Immunoblot showing wild type (WT) and mutant RAβ FLAG-tagged PP2A Aβ expression levels in HEK TER cells treated with shAβ. For B, D, E, F, and G data are shown as mean±standard deviation (SD) for 3 independent experiments.

The compositions and methods described herein relate generally to diagnostic techniques involving the detection of RalA phosphorylation in a sample and/or a subject.

Cancer

Cancer has come to be understood as a class of diseases or disorders characterized by unregulated cellular proliferation. The unregulated, dividing cells can invade immediately adjacent tissue or metastasize into distant sites. The underlying cause is believed to be DNA damage that alters the expression of a specific subset of genes that encode proteins involved in the regulation of cell growth and differentiation. The genes that, when mutated or overexpressed, cause cancer are known as proto-oncogenes, and the mutant gene per se is an oncogene.

Studying transformation in human cell culture models has helped elucidate pathways related to spontaneous cancer development (Hahn, W. C., and Weinberg, R. A., *N. Engl. J. Med.*, 347:1593-1603). For example, ectopic expression of the telomerase catalytic subunit (hTERT), the SV40 Early Region (SV40 ER), and an oncogenic allele of H-RAS have been demonstrated to confer a tumorigenic phenotype to several types of normal human cells (Zhao et at, *Trends Mol. Med.*, 10:344-350, 2004). Furthermore, defined combinations of cancer-associated mutations that suffice to transform human cells have been identified (Boehm et al., *Mol. Cell Biol.*, 25:6464-6474, 2005; Drayton et al., *Cancer Cell*, 4:301-310, 2003; Seger et al., *Cancer Cell*, 2:401-413, 2002). For example, the SV40 ER encodes two oncoproteins, the SV40 large T (LT) and small t (ST) antigens. LT binds the retinoblastoma and p53 proteins and in turn inactivates these two tumor suppressor pathways (Ali, S. H., and DeCaprio, J. A., *Semin. Cancer Biol.*, 11:15-23, 2001), activities central to its role in human cell transformation (Hahn et al., *Mol. Cell Biol.*, 22:2111-2123, 2002; Voorhoeve, P. M., and Agami, R., *Cancer Cell*, 4:311-319, 2003).

ST binds the serine-threonine protein phosphatase 2A (PP2A), and this interaction is essential for ST to transform cells (Hahn et al., *Mol. Cell Biol.*, 22:2111-2123, 2002; Sugano et al., *J. Virol.*, 41:1073-1075, 1982; Yu et al., *Virology*, 290:192-198, 2001). The viral oncoproteins SV40 ST, the small and middle T antigens of polyoma virus, and the adenoviral protein E4orf4 all bind PP2A (Schonthal, A. H., *Cancer Lett.*, 170:1-13, 2001), suggesting that like other targets of viral oncoproteins, PP2A plays a important role in tumor suppression. The involvement of PP2A in transformation is also supported by the observation that the PP2A inhibitor, okadaic acid (OA), is a potent tumor promoter (Suganuma et al., *Proc. Natl. Acad. Sci.*, 85:1768-1771, 1988).

Inappropriate protein kinase activation has also been demonstrated to have a causal role in many cancers, and several protein kinases are known oncogenes capable of programming the malignant phenotype (Broach, J. R., and Levine, A. J., *Curr. Opin. Genet. Dev.*, 7:1-6. 1997; Hanahan. D., and Weinberg, R. A., *Cell*, 100:57-70, 2000). In contrast, the involvement of protein phosphatases in cancer development remains a grey area.

PP2A

PP2A comprises a family of ubiquitously expressed serine-threonine phosphatases implicated in regulation of many signaling pathways, and several PP2A complexes have been implicated in cancer development (Schonthal, 2001). PP2A holoenzymes are composed of three subunits, a catalytic C subunit, a structural A subunit, and a regulatory B subunit. Each of these subunits is encoded by several distinct genes, which are assembled to create numerous ABC holoenzymes (Janssens, V., and Goris, J., *Biochem. J.*, 353:417-439, 2001). The large number of different PP2A heterotrimers suggests that specific regulatory subunits mediate particular physiological functions.

Suppressing the expression of the PP2A B56γ regulatory subunit or partially depleting the structural Aα subunit cooperates with LT, hTERT and H-RAS to convert human cells to tumorigenicity (Chen et al., *Cancer Res.*, 65:8183-8192, 2005; Chen et al., *Cancer Cell*, 5:127-136, 2004). Although mutations of PP2A Aα occur at low frequency in human tumors (Calin et al., *Oncogene*, 19:1191-1195, 2000), mutations of the second PP2A A subunit, Aβ, are more common (Calin et al., *Oncogene*, 19:1191-1195, 2000; Ruediger et al., *Oncogene*, 20:1892-1899, 2001; Takagi et al., *Gut*, 47:268-271, 2000; Tamaki., *Oncol. Rep.*, 11:655-659, 2004; Wang et al., *Science*, 282:284-287, 1998). Specifically, somatic mutations of Aβ, including point mutations, deletions, frameshifts, and splicing abnormalities, have been found in 8-15% of colon cancers, 15% of lung cancers, 13% of breast cancers, and 6% of tumor cell lines (Calin et al., *Oncogene*, 19:1191-1195, 2000; Ruediger et al., *Oncogene*, 20:1892-1899, 2001; Takagi et al., *Gut*, 47:268-271, 2000; Tamaki et al., *Oncol. Rep.*, 11:655-659, 2004; Wang et al., *Science*, 282:284-287, 1998). These cancer-associated PP2A Aβ mutants are defective in binding to B and/or C subunits in vitro (Ruediger et al., *Oncogene*, 20:1892-1899, 2001). In addition to mutations, the PP2A Aβ gene is located at 11q23, a chromosomal region frequently deleted in human cancers (Baysal et al., *Eur. J. Hum. Genet.*, 9:121-129, 2001). Moreover, reduced expression of the PP2A Aβ subunit has been found in 16 of 32 cancer cell lines derived from human lung, colon, breast, and cervical carcinomas (Zhou et al., *Biochem. J.*, 369:387-398, 2003). While these observations implicate PP2A Aβ as a tumor suppressor gene, the mechanism by which Aβ loss of function contributes to tumor development remains undefined.

RalA

RalA is a multifunctional protein, regulating membrane transport, apoptosis, transcription, cell migration and cell proliferation (Camonis, J. H., and White, M. A., *Trends Cell Biol.*, 115:327-332, 2005; Feig, L. A., Trends Cell Biol., 13:419-425, 2003).

PP2A Aβ and RalA

Described below are studies that elucidate and characterize the association between the protein phosphatase PP2A and RalA. Studies described below show that the transforming capabilities of RalA are dependent on the phosphorylation of human RalA (SEQ ID NO:9), at one or both of serine 183 (Ser183) and serine 194 (Ser194). Other studies show that protein phosphatase PP2A complexes containing wild type Aβ subunits normally dephosphorylate RalA at one or both of Ser183 and Ser194 and that the dephosphorylation of one or both of these sites is required to suppress transformation. Furthermore, it is shown below that cancer-associated PP2A Aβ mutants fail to down regulate RalA, leading to increased RalA activity in cells lacking functional PP2A Aβ complexes, and that RalA phosphorylated at one or both of Ser183 and Ser194 accumulates in cells lacking functional PP2A Aβ complexes. It is shown that the accumulation of RalA phosphorylated at one or both or Ser183 and Ser194 induces cellular transformation and tumorgenicity. Because of the importance of RalA in several important cancers, including but not limited to pancreatic cancer and lung cancer, the studies show that RalA phosphorylated at one or both of Ser183 and Ser194 is an important and easily detectible cancer biomarker.

In one aspect, therefore, the present disclosure includes an isolated antibody molecule or antigen binding portion, not excluding a fragment, thereof that binds to (i.e., specifically binds to) RalA (e.g., a polypeptide, comprising, consisting of or consisting essentially of SEQ ID NO:9), that is phosphorylated at one or both of Ser183 and Ser194. In another embodiment the isolated antibody molecule or antigen binding portion binds to (i.e., specifically binds to) RalA (e.g., a polypeptide, comprising, consisting of or consisting essentially of SEQ ID NO:9) that is phosphorylated at both Ser183 and Ser194. In another embodiment the isolated antibody molecule or antigen binding portion binds to (i.e., specifically binds to) RalA (e.g., a polypeptide, comprising, consisting of or consisting essentially of SEQ ID NO:9) that is phosphorylated at Ser183 and is not phosphorylated at Ser194. In another embodiment the isolated antibody molecule or antigen binding portion binds to (i.e., specifically binds to) RalA (e.g., a polypeptide, comprising, consisting of or consisting essentially of SEQ ID NO:9) that is phosphorylated at Ser194 and is not phosphorylated at Ser183. In various embodiments of all of these antibodies or antigen binding portion thereof, the antibody or antigen binding portion thereof does not bind or binds with at least 10-fold, 100-fold or 1,000-fold less affinity to RalA (e.g., a polypeptide, comprising, consisting of or consisting essentially of SEQ ID NO:9) that is not phosphorylated at Ser194 and is not phosphorylated at Ser183. In some embodiments the RalA (e.g., a polypeptide comprising, consisting essentially of, or consisting of SEQ ID NO:9) is also phosphorylated at one or more additional amino acids.

In an additional exemplary embodiment, the present disclosure includes an isolated antibody or antigen binding portion thereof that binds to a polypeptide of RalA, herein designated SEQ ID NO:9, that is not phosphorylated at either of Ser183 and Ser194.

It is contemplated that the isolated antibody or antigen binding portion thereof of the present disclosure may be useful in methods to detect the presence of a polypeptide of RalA (e.g., a polypeptide comprising, consisting essentially of, or consisting of SEQ ID NO:9), that is phosphorylated at one or both of Ser183 and Ser194 in a cultured cell or in a subject. For example, the isolated antibody or antigen binding portion thereof of the present disclosure may be used for monitoring the degree of phosphorylation of a polypeptide of RalA (e.g., a polypeptide comprising, consisting essentially of, or consisting of SEQ ID NO:9) at one or both of Ser183 and Ser194. The isolated antibody or antigen binding portion thereof of the present disclosure may also be used for diagnosing cancer in a subject by detecting the presence of a polypeptide of RalA (e.g., a polypeptide comprising, consisting essentially of, or consisting of SEQ ID NO:9) that is phosphorylated at one or both of Ser183 and Ser194. Exemplary cancers that may be diagnosed include but are not limited to lung cancers, including non-small cell lung cancer and small cell lung cancer, pancreatic cancers, colon cancers, cervical cancers, and breast cancers. It is also contemplated that the isolated antibody or antigen binding portion thereof of the present disclosure may be useful to detect the presence of a polypeptide of RalA (e.g., a polypeptide comprising, consisting essentially of, or consisting of SEQ ID NO:9) that is not phosphorylated at either of Ser183 and Ser194.

Antibody Generation

As used herein, an "antibody" is a protein comprising one or more polypeptides selected from immunoglobulin light chains and immunoglobulin heavy chains. The component polypeptides of an antibody composed of more than one polypeptide may optionally be disulfide-bound or otherwise covalently crosslinked. Accordingly, antibodies include intact immunoglobulins of types IgA, IgG, IgE, IgD, IgM, as well as subtypes thereof, including IgA1, IgA2, IgG1, IgG2, IgG2a, IgG2b, IgG3, and IgG4. The light chains of the immunoglobulin may be of types kappa or lambda or antigen-binding portions thereof.

The isolated antibody described herein may also include but is not limited to an antigen-binding portions, including portions of intact immunoglobulins that retain antigen-binding specificity, e.g., Fab fragments, Fab' fragments, F(ab')$_2$ fragments, F(v) fragments, heavy chain monomers or dimers, light chain monomers or dimers, dimers consisting of one heavy and one light chain, and the like.

The antibody described herein is also contemplated as a chimeric recombinant antibody or an antibody produced by recombinant DNA technology, in which all or part of the hinge and constant regions of an immunoglobulin light chain, heavy chain, or both, have been substituted for the corresponding regions from another immunoglobulin light chain or heavy chain.

Many types of antibodies that bind to RalA or SEQ ID NO: 9 that is phosphorylated at one or both of ser183 and ser194 are useful in the methods of this disclosure. These include monospecific (e.g., monoclonal) antibodies, polyclonal antibodies, recombinant antibodies, chimeric recombinant antibodies, humanized recombinant antibodies, as well as antigen-binding portions of the foregoing.

The technology for producing monoclonal antibodies is well known. See generally, Harlow, E. and Lane, D. (1988) *Antibodies: A Laboratory Manual*, Cold Spring Harbor Laboratory Press, Cold Spring Harbor, N.Y.; Kohler et al., *Nature*, "Continuous Cultures of Fused Cells Secreting Antibody of Predefined Specificity," 256, pp. 495-97 (1975).

More specifically, the monoclonal antibodies of this disclosure can be generated by well known hybridoma technology. For instance, (3-6,–/–animals (e. g., a mammal including mice, rats, chickens, or rabbits) can be immunized with purified or crudecz preparations, cells transfected with cDNA constructs encoding the immunogen, or both antigens, cells that constitutively express the antigen, and the like. The antigen can be delivered as purified protein, protein expressed on cells, protein fragment or peptide thereof, or as naked DNA or viral vectors encoding the protein, protein fragment, or peptide. Immunogens may be individually injected into animals. Immunogens may also be co-injected into animals.

Exemplary immunogens for the purpose of generating the antibody molecule or antigen binding portion of this disclosure include but are not limited to cell-free preparations or polypeptides. Specifically, immunogens for the purpose of generating the antibody molecule or antigen binding portion of this disclosure include but are not limited to cell-free preparations or a peptide containing a fragment of RalA that includes phosphorylated Ser183 and/or phosphorylated Ser194 or an immunogen containing a peptide that is a fragment of RalA that includes phosphorylated Ser183 and a peptide that is a fragment of RalA that includes phosphorylated Ser194.

Phosphorylated polypeptides having fewer than, about 20 amino acids may be produced using conventional chemical synthesis techniques. Synthetically produced polypeptides useful in the methods of this disclosure can be advantageously produced in extremely high yields and can be easily purified.

Soluble polypeptides may be synthesized by solution phase or solid phase polypeptide synthesis and, optionally, digested with carboxypeptidase (to remove C-terminal amino acids) or degraded by manual Edman degradation (to remove N-terminal amino acids). The use of solution phase synthesis may allow for the direct addition of certain derivatized amino acids to the growing polypeptide chain, such as the O-sulfate ester of tyrosine. This obviates the need for a subsequent derivatization step to modify any residue of the polypeptides useful in the methods of this disclosure.

When required, proper folding of the polypeptides may be achieved under oxidative conditions which favor disulfide bridge formation as described by Kent, "Chemical Synthesis of Polypeptides and Proteins," Ann. Rev. Biochem., 57, pp. 957-89 (1988). Polypeptides produced in this way may then be purified by separation techniques widely known in the art.

Immunization can be accomplished using standard procedures, as described above. It will be appreciated that the unit dose and immunization regimen depend on the species of mammal immunized, its immune status, the body weight of the mammal, etc. Typically, the immunized mammals are bled and the serum from each blood sample is assayed for particular antibodies using appropriate screening assays. Alternatively, antibodies secreted by these hybridomas are screened for their ability to bind specifically to RalA (e.g., a polypeptide comprising, consisting essentially of, or consisting of SEQ ID NO:9) that has been phosphorylated at one or both of Ser183 and Ser194 (e.g., binding to transfected cells and not to untransfected parent cells) and for any other desired features, e. g., the inability to bind specifically to RalA (e.g., a polypeptide comprising, consisting essentially of, or consisting of SEQ ID NO:9) that is not phosphorylated at either Ser183 and Ser194. It is also contemplated that these peptides may include silent substitutions, mutations, or deletions that do not alter the immunogenicity of the peptide.

Hybridoma cells that test positive in the above screening assays are cultured in a nutrient medium under conditions that allow the cells to secrete the monoclonal antibodies into the culture medium. The conditioned hybridoma culture supernatant is then collected and antibodies contained in the supernatant are purified. Alternatively, the desired antibody may be produced by injecting the hybridoma cells into the peritoneal cavity of an unimmunized animal (e.g., a mouse). The hybridoma cells proliferate in the peritoneal cavity, secreting the antibody which accumulates as ascites fluid. The antibody may then be harvested by withdrawing the ascites fluid from the peritoneal cavity with a syringe.

The monoclonal antibodies can also be generated by isolating the antibody-coding cDNAs from the desired hybridomas, transfecting mammalian host cells (e. g., CHO or NSO cells) with the cDNAs, culturing the transfected host cells, and recovering the antibody from the culture medium.

The monoclonal antibodies of this disclosure can also be generated by engineering a cognate hybridoma (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e. g., a human). Methods of making chimeric antibodies are well known in the art.

The antibodies useful in the methods described herein can also be recombinant antibodies produced by host cells transformed with DNA encoding immunoglobulin light and heavy chains of a desired antibody. Recombinant antibodies may be produced by well-known genetic engineering techniques. See, e.g., U.S. Pat. No. 4,816,397, which is incorporated herein by reference. For example, recombinant antibodies may be produced by cloning cDNA or genomic DNA encoding the immunoglobulin light and heavy chains of the desired antibody from a hybridoma cell that produces an antibody useful in the methods of this disclosure. The cDNA or genomic DNA encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector.

Prokaryotic or eukaryotic host cells may be used. Expression in eukaryotic host cells is preferred because such cells are more likely than prokaryotic cells to assemble and secrete a properly folded and immunologically active antibody. It is possible that the host cells will produce portions of intact antibodies, such as light chain dimers or heavy chain dimers, which also are antibodies according to the methods described herein.

It may be desired to transform a host cell with DNA encoding either the light chain or the heavy chain (but not both) of an antibody homolog. Recombinant DNA technology may also be used to remove some or all of the DNA encoding either or both of the light and heavy chains that is not necessary for RalA binding. The molecules expressed from such truncated DNA molecules are useful in the methods of this disclosure. In addition, bi-functional antibodies may be produced.

Chimeric recombinant anti-RalA antibodies can be produced by transforming a host cell with a suitable expression vector comprising DNA encoding the desired immunoglobulin light and heavy chains, in which all or some of the DNA encoding the hinge and constant regions of the heavy and/or the light chain have been substituted with DNA from the corresponding region of an immunoglobulin light or heavy chain of a different species. When the original recombinant antibody is nonhuman, and the inhibitor is to be administered to a human, substitution of corresponding human sequences is preferred. An exemplary chimeric recombinant antibody has mouse variable regions and human hinge and constant regions. See generally, U.S. Pat. No. 4,816,397; Morrison et al., "Chimeric Human Antibody Molecules: Mouse Antigen-Binding Domains With Human Constant Region Domains", *Proc. Natl. Acad. Sci. USA,* 81, pp. 6851-55 (1984); Robinson et al., International Patent Publication PCT/US86/02269; Akira, et al., European Patent Application 184,187; Taniguchi, M., European Patent Application 171,496; Neuberger et al., International Application WO 86/01533; Better et al. (1988) *Science* 240:1041-1043; Liu et al. (1987) *PNAS* 84:3439-3443; Liu et al., (1987), *J. Immunol.* 139:3521-3526; Sun et al. (1987) *PNAS* 84:214-218; Nishimura et al., (1987), *Canc. Res.* 47:999-1005; Wood et al. (1985) *Nature* 314:446-449; and Shaw et al., (1988), *J. Natl Cancer Inst.* 80:1553-1559. For example, the isolated antibody or antigen binding fragment thereof of the present disclosure may contain a marker to facilitate detection of the isolated antibody or antigen binding fragment.

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. (1989) *Science* 246:1275; and Orlandi et al. (1989) *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR (Larrick et al., (1991), *Biotechniques* 11:152-156; Larrick et al., (1991), *Methods: Companion to Methods in Enzymology* 2:106-110).

Examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226: 889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982. Kits for generating phage display libraries are commercially available (e.g., the Pharmacia Recombinant Phage Antibody System, catalog no. 27-9400-01; and the Stratagene SurfZAP™ phage display kit, catalog no. 240612).

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., Nature (1990) 348:552-554, complete VH and VL domains of an antibody, joined by a flexible (Gly4-Ser)3 linker can be used to produce a single chain antibody which can render the display package separable based on antigen affinity. Isolated scFV antibodies immunoreactive with the antigen can subsequently be formulated into a pharmaceutical preparation for use in the subject method.

Fragments of anti-RalA antibodies that are not intact antibodies are also useful in the methods described herein. Such fragments can be derived from any of the antibodies described above. For example, antigen-binding fragments or antigen-binding portions, as well as full-length monomeric, dimeric or trimeric polypeptides derived from the above-described antibodies are themselves useful. Useful antigen-binding fragments or antigen-binding portions of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" or "antigen binding portion" of an antibody. These antibody fragments are obtained using conventional techniques known to those with skill in the art, and the fragments are screened for utility in the same manner as are intact antibodies.

Antibody fragments can also be produced by chemical methods, e.g., by cleaving an intact antibody with a protease, such as pepsin or papain, and optionally treating the cleaved product with a reducing agent. Alternatively, useful fragments can be produced by using host cells transformed with truncated heavy and/or light chain genes. Heavy and light chain monomers may be produced by treating an intact antibody with a reducing agent, such as dithioreitol, followed by purification to separate the chains. Heavy and light chain monomers may also be produced by host cells transformed with DNA encoding either the desired heavy chain or light chain, but not both. See, e.g., Ward et al., "Binding Activities of a Repertoire of Single Immunoglobulin Variable Domains Secreted from *Escherichia coli*", Nature, 341, pp. 544-46 (1989); Sastry et al., "Cloning of the Immunological Repertoire in *Escherichia coli* for Generation of Monoclonal Catalytic Antibodies: Construction of a Heavy Chain Variable Region-Specific cDNA Library", *Proc. Natl. Acad. Sci. USA,* 86, pp. 5728-32 (1989).

The isolated antibody or antigen binding portion thereof will have a binding affinity of $10^{-7}$-$10^{-11}$ K$_d$, $10^{-8}$-$10^{-11}$ K$_d$, $10^{-9}$-$10^{-11}$ K$_d$, and $10^{-10}$-$10^{-11}$ K$_d$.

Methods that are known in the art but not specifically described herein are also within the scope of this disclosure. For instance, antibodies of this disclosure can also be identified using phage-displayed antibody libraries, such as those described in Smith, 1985, Science 228: 1315-7; U.S. Pat. Nos. 5,565,332; 5,733,743; 6,291,650, and 6,303,313. Additional antibodies of this disclosure can be made by coupling the heavy chains identified herein with a noncognate light chain, e. g., a light chain identified by phage display technology.

Aptamer Generation

The use of an aptamer to detect a polypeptide of RalA (e.g., a polypeptide comprising, consisting essentially of, or consisting of SEQ ID NO:9) that is phosphorylated at one or both of Ser183 and Ser194 is within the scope of the present disclosure.

Nucleic acid "aptamers" can be developed for binding to virtually any target molecule, as is generally described in U.S. Pat. Nos. 5,270,163, 5,475,096, 5,567,588, 5,595,877, 5,637,459, 5,683,867, 5,705,337, and related patents, hereby incorporated by reference. The aptamers comprise nucleic acids. By "nucleic acid" or "oligonucleotide" or grammatical equivalents herein means at least two nucleotides covalently linked together. A nucleic acid of the present disclosure will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawal et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252-3 (1998); positive backbones (Denpcy et al., Proc. NaU. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifations in Antisense Research", Ed. Y. S. Sanghui and P. Dan Cook; Mesmaeker et al., Bloorganic.& Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed.Y. S. Sanghui and P. Dart Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. These modifications of the ribose-phosphate backbone may be done to increase the stability and half-life of such molecules in physiological environments.

As will be appreciated by those in the art, the antibody or aptamer can be attached to the solid support in a number of ways, including covalent and non-covalent methods, using techniques well known in the art. Preferably, the technique utilized does not mask or sterically hinder the binding region of most of the antibodies used in the experiments.

Generally, in their most basic form, in vitro selection techniques for identifying RNA aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques. The DNA pool is then transcribed in vitro. The RNA transcripts are then subjected to affinity chromatography. The transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand.

Peptide aptamers contain random combinations of a small number of amino acid residues, e.g., 5, 6, 7 or more, but preferably less than 100, more preferably less than 50, and most preferably less than 20. The peptide aptamers of the disclosure can be produced recombinantly, from a corresponding nucleic acid sequence, or synthetically using art recognized techniques in peptide chemistry. A library of nucleic acid sequences encoding random peptide aptamers can be generated by combinatorial mutagenesis at the nucleic acid level. Alternatively, a variegated library of nucleic acid sequences encoding random peptide aptamers can be produced using chemical synthesis of a degenerate aptamer gene sequence using an automatic DNA synthesizer, where the synthetic gene is then ligated into an appropriate expression vector, e.g., a retroviral vector. Use of a degenerate set of genes allows for, in one mixture, all of the sequences encoding the desired set of potential random peptide aptamer sequences to be represented. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

Screening for a Peptide of RalA, Herein Designated as SEQ ID NO:9 that is Phosphorylated at One or Both of Ser183 and Ser194

It is contemplated that the isolated antibody or antigen binding portion thereof may be used to detect a peptide of RalA, herein designated SEQ ID NO:9, that is phosphorylated at one or both of Ser183 and Ser194 in a biological sample, such as an in vitro cultured cell line or a subject. It is within the scope of the disclosure that the subject may be a mammal, for example, a human and a non-human mammal.

It will be understood there are multiple circumstances in which it will be advantageous to determine or detect the presence of a polypeptide of RalA (e.g., a polypeptide comprising, consisting essentially of, or consisting of SEQ ID NO:9) that is phosphorylated at one or both of Ser183 and Ser194 in a biological sample using the isolated antibody or antigen binding portion thereof of the present disclosure. Such a screen may involve screening a sample such as cultured cells. In all cases, such a screen will clearly require providing a biological sample, contacting the biological sample with the isolated antibody or antigen binding portion, and detecting the presence or absence of a polypeptide of RalA (e.g., a polypeptide comprising, consisting essentially of, or consisting of SEQ ID NO:9) that is phosphorylated at one or both of Ser183 and Ser194. Such a technique could easily be performed using, for example, standard immunoblotting, and quantification may be performed if necessary using densitometry analysis with, for example, using Scion image software. All these techniques are well known in the art.

In the instance that the screen is performed to monitor the degree of phosphorylation of a polypeptide of RalA (e.g., a polypeptide comprising, consisting essentially of, or consisting of SEQ ID NO:9) for example, during therapy to determine the effectiveness of the therapy or to assess the benefit of the therapy to the subject, the biological samples such be taken at pre-determined time points. For example, the first biological sample may be provided taken from a subject at a first time point before or during therapy. A second biological sample may then be provided taken from the subject at a second time point that occurs after that of the first time point. For example, the first and second sample may be taken with intervals of one hour, one day, one week, one month, and one year. A beneficial therapeutic effect of the therapy may then be assessed or determined based on the observation of an equal or lower level of detection of a polypeptide of RalA that is phosphorylated at one or both of Ser183 and Ser194 bound to the isolated antibody or antigen binding portion thereof. Likewise, it will be understood that the observation of an equal or lower level of detection of a polypeptide of RalA that is phosphorylated at one or both of Ser183 and Ser194 bound to the isolated antibody or antigen binding portion thereof will indicate that the therapy is effective. In other words, a subjects therapy could be perceived as effective or beneficial if the degree of RalA phosphorylation at one or both of Ser183 and Ser194 did not significantly increase between the first and the second samples being taken. Screening as such to determine the effectiveness of therapy or to assess the benefit of the therapy to the subject may then be continued until termination of therapy at pre-determined intervals, for example, screening may be performed yearly, monthly, weekly, and daily.

The isolated antibody or binding portion thereof may be useful for diagnosing a cancer in a subject. Suitable cancer for diagnosis include all those cancers in which altered RalA activity is causative or predictive or indicative. As described above, a provided biological sample will be contacted with the isolated antibody or antigen binding portion, and the presence or absence of a polypeptide of RalA (e.g., a polypeptide comprising, consisting essentially of, or consisting of SEQ ID NO:9) that is phosphorylated at one or both of Ser183 and Ser194, which is diagnostic for cancer, will be detected using, for example, standard: immunoblotting techniques. Quantification may be performed by densitometry analysis using, for example, using Scion image software. To ascertain if RalA phosphorylation levels at one or both of Ser183 and Ser194 are high in a the provided first biological sample taken from a test subject, second biological sample will be provided taken from a second known cancer free control subject or a known confirmed negative standard. In this case, statistically significant higher RalA phosphorylation at one or both of Ser183 and Ser194 will be diagnostic for cancer. In some cases the test sample is simply compared to a null sample, e.g., any detectable degree of phosphorylation is considered diagnostic.

It is within the scope of this disclosure, that the isolated antibody or antigen binding portion thereof will be used to screen potential inhibitors of the kinase responsible for phosphorylating RalA. Such inhibitors include, but are not limited to, small molecules, antibodies and antigen binding portions thereof, peptides, and chemical compounds. This screen generally entails providing a biological sample, such as a cultured cell or a cultured cell extract expressing or capable of expressing RalA phosphorylation at one or both of Ser183 and Ser194, for example, including but not limited to, a PP2A Aβ mutant cancer cell line. It is also contemplated that RalA may be introduced into a cell line containing a protein kinase that phosphorylates RalA, for example, including but not limited to Aurora-A kinase, Akt, Ras, or cells with elevated calmodulin. This biological sample will then be contacted with the putative kinase inhibitor described above (i.e., specifically binds to). This entire biological sample will then be contacted with the isolated antibody or antigen binding portion thereof described herein, and the presence or absence of RalA that is phosphorylated at one or both of Ser183 and Ser194 will be detected. Such a technique could easily be performed using, for example, standard immunoblotting, and quantification may be performed if necessary using densitometry analysis with, for example, using Scion image software. All these techniques are well known in the art. A viable inhibitor of the kinase that phosphorylates RalA will reduced the levels of detection of RalA that is phosphorylated at one or both of Ser183 and Ser194.

Antibody Kits

The isolated antibody or antigen binding portion thereof described herein may be packaged for distribution and use as a part of a kit. The isolated antibody or antigen binding fragment thereof described herein may be supplied in solution for freezing (i.e., a solution containing glycerol) or for refrigeration only. Alternatively, the isolated antibody or antigen binding fragment thereof may be supplied in a lyophillized form. The kit will also include a reagent to detect the bound antibody. The reagent may include a secondary antibody to detect the isolated antibody for example including but not limited to an anti-mouse, anti-rabbit, anti-chicken, and anti-rat immunoglobulins of types IgA, IgG, IgE, IgD, IgM, as well as subtypes thereof. The secondary antibody may be conjugated to an enzyme, such as horse radish peroxidase (hrp), to a fluorescent label, or to a radiolabel. The kit will also include instructions describing the details of the isolated antibody or antigen binding fragment thereof, for example, including but not limited to batch specific variables, such as affinity, concentration, and molecular weight, as well as describing rehydration instructions (if lyophilized) and optimum conditions for use thereof. The kit will be supplied in an insulated vehicle.

EXAMPLES

Example 1

PP2A Aβ Suppression Transforms Human Cells

To assess the role of the PP2A A structural subunits in human cell transformation, we suppressed PP2A Aα and Aβ expression in immortal, non-tumorigenic HEK cells expressing H-RAS (HEK TER) using short hairpin RNA (shRNA) designed to specifically target PP2A Aα (designated pMKO.1-shAα) and PP2A Aβ (designated pMKO.1-shAβ and pMKO.1-shAβ2). The methods required for generating these shRNA are well known in the art, as follows.

pMKO.1-shAα (designated shAα), pMKO.1-shAβ (designated shAβ), and pMKO.1-shAβ2 (designated shAβ2) were generated by introducing oligonucleotides corresponding to nucleotides 1798-1818 of SEQ ID NO:1 (gene accession number J02902), nucleotides 172-192, and nucleotides 1806-1826, respectively, of SEQ ID NO:2 (gene accession number AF087438) followed by a 6-bp loop and the corresponding antisense sequence, and followed by five thymidines into pMKO.1-Puro, according to a previously described protocol (Masutomi et al., *Cell*, 114:241-253, 2003). The pLKO.1-Puro, pLKO.1-shRalA-1, or pLKO.1-shRalA-2 vectors were provided by the RNAi Consortium (Broad Institute) (Moffat et al., *Cell*, 124:1283-1298, 2006).

A wild type (WT) FLAG epitope-tagged version of PP2A Aβ (designated wtPP2A Aβ), which was generated using RT-PCR and the sense oligonucleotide SEQ ID NO:3 and the antisense oligonucleotide SEQ ID NO:4:

```
                                            (SEQ ID NO: 3)
5'-GGCGGCGGATCCATGGACTACAAAGACGATGACGACAAGGCGGG
CGCATCAGAGCTCGGGACC-3'

(SEQ ID NO: 4)
5'-GGCGGCGGCCTCGAGTTATGCCAATGCAAGAACACTTATAGC-3'
```

This resulting PCR fragment was then subcloned into the retroviral vector pMIG.

All cells were cultured in minimal Eagle medium alpha (MEMα) supplemented with 10% heat-inactivated fetal calf serum (IFS).

wtPP2A Aβ was introduced into cells using amphotropic retroviruses to generate the stable cell lines, using a previously described protocol (Hahn et al., *Mol. Cell. Biol.*, 22:2111-2123, 2002). HEK TER shAβ and shAβ-2 cells were generated by infecting HEK TER cells with shAβ- or shAβ1-containing retroviruses and selecting with puromycin (0.5 μg/ml).

shAβ was verified by introducing shAβ into HEK TER cells, described supra, overexpressing wtPP2A Aβ. As shown in FIG. 1A, infection with shAβ-containing retroviruses led to suppression of ectopically expressed wtPP2A Aβ. In contrast, control shRNA targeting GFP (shGFP) did not suppress ectopically expressed wtPP2A Aβ.

To further verify shAβ, HEK TER cell lines were generated that stably harbored either shAβ (HEK TER-shAβ) or a control shGFP (HEK TER-shGFP), as described above. Endogenous Aβ mRNA levels were then assessed using quantitative RT-PCR, as follows.

Total RNA was prepared using TRIzol® Reagent (Invitrogen, Carlsbad, Calif.), and cDNA synthesis was performed using the RT-for-PCR kit (BD Biosciences, San Diego, Calif.). Aβ was amplified using the sense oligonucleotide SEQ ID NO:5 (also designated as S117) and the antisense oligonucleotide SEQ ID NO:6 (also designated as R399).

```
5'-GACGAGCTCCGCAATGAAG-3'    (SEQ ID NO: 5)

5'-GGGACTCCACAGCCTTGT-3'     (SEQ ID NO: 6)
```

Real-time PCR reactions were conducted in an ABI Prism 7700 Sequence Detection System (Applied Biosystems, Foster City, Calif.) using SYBR Green PCR Master Mix (Applied Biosystems).

Figure 1B:
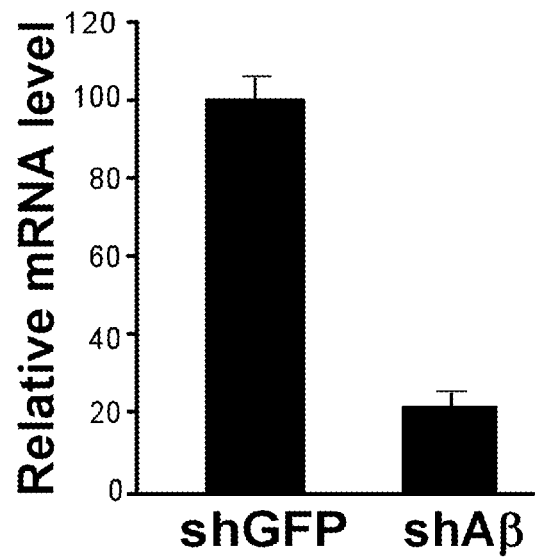

As shown in FIG. 1B, shAβ expression in HEK TER cells reduced endogenous Aβ mRNA levels by 78±6% compared to those found in shGFP treated control cells (FIG. 1B).

To assess the general consequences of PP2A Aα and Aβ suppression, an additional HEK TER cell line was generated stably expressing shAα, as described above. Cells were suspended in a lysis buffer [50 mM Tris-HCl, pH 7.5, 150 mM NaCl, 1 mM EDTA, protease inhibitor cocktail (Roche, Mannheim, Germany) and 0.5% NP-40] and cleared of insoluble material by centrifugation. Soluble proteins (100 μg) were subjected to SDS-PAGE followed by immunoblotting. To purify membrane-rich fraction of proteins, ProteoExtract Membrane Protein Extraction kit (Calbiochem) was used according the manufacturer's instructions. Membranes were probed with anti-PP2A A antibody (clone 6G3) (Covance, Richmond, Calif.), anti-PP2A Cα antibody (BD Biosciences, San Diego, Calif.), and affinity-purified polyclonal antibodies raised against the B55α, B56γ, and B56δ subunit, using the previously described method (Chen et al., *Cancer Cell*, 5:127-136, 2004). The anti-PP2A B56ε polyclonal antibody was obtained by immunizing rabbits with a peptide designated SEQ ID NO:7, which corresponds to amino acids 454-467 in SEQ ID NO: 8 (Accession Number NP_006237).

```
ELKRGLRRDGIIPT          (SEQ ID NO: 7)
```

Figure 1C:
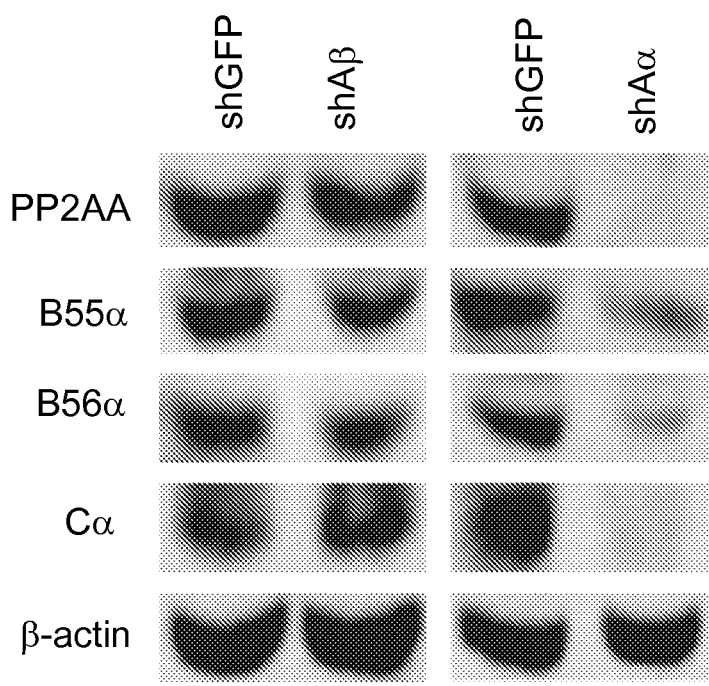
Figure 1D:
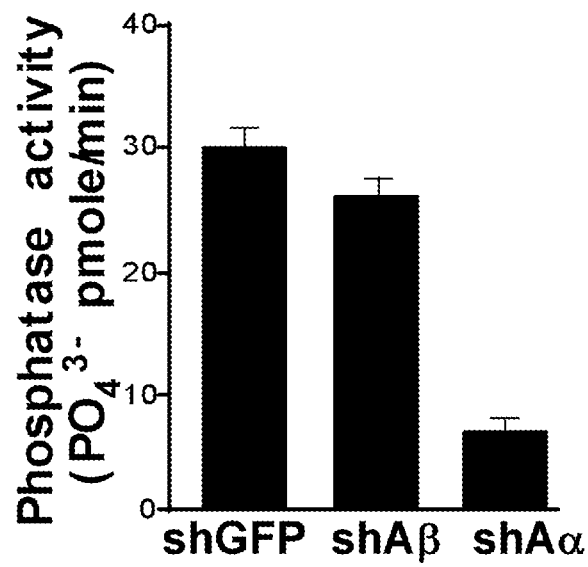

As shown in the left panel of FIG. 1C, Aβ suppression did not detectibly alter the levels of the various PP2A subunits. In contrast, as shown in the right panel of FIG. 1C, PP2A Aα suppression resulted in a substantial reduction in B55α and B56ε regulatory subunit levels as well as Cα catalytic subunit levels. This observation demonstrates that the PP2A regulatory and catalytic subunits exhibit limited stability when not bound to a structural PP2A A subunit, as described elsewhere (Silverstein et al., *Proc. Natl. Acad. Sci. U.S.A.*, 99:4221-4226, 2002). This putative decrease in PP2A was corroborated by quantifying PP2A protein phosphatases activity in whole cell lysates, as follows. Free phosphate was first removed from cell lysates by passage through a Sephadex G-25 column (Amersham, Piscataway, N.J.). Serine/threonine phosphatase activity in these cell lysates was then measured by the capacity to dephosphorylate a synthetic phosphothreonine peptide RRA(pT)VA specific for PP2A. Specificity was confirmed using purified PP2A core enzyme in the presence or absence of 5 nM OA. After 30 min incubation at RT, free phosphate was measured colorimetrically. As shown in FIG. 1D, we observed that PP2A-attributable phosphatase activity was decreased by 80±6% or 13±3% in cells expressing shAα or shAβ, respectively, compared to control shGFP cells (FIG. 1D). These findings confirm our observation above, and are in agreement with previous observations by others that concluded that PP2A complexes containing Aβ represent a small fraction of the total PP2A complexes (Hemmings et al., *Biochem.*, 29:3166-3173, 1990; Zhou et al., *Biochem. J.*, 369:387-398, 2003).

We next examined the effects PP2A Aα or Aβ suppression on proliferation, anchorage-independent (AI) growth and tumor formation, using the following art recognized techniques.

Briefly, 1×10$^4$ cells were plated in triplicate and counted every 4 d. For population doublings, a seeding density of 1×10$^4$ cells in a 10-cm plate was used for all cultures. Soft agar and tumorigenicity assays were performed as described (Hahn et al., *Nat. Med.*, 5:1164-1170, 1999). AI colonies were counted 4 wk after seeding at 10× magnification. The number of tumors formed was determined 40 d after injection.

Figure 1E:
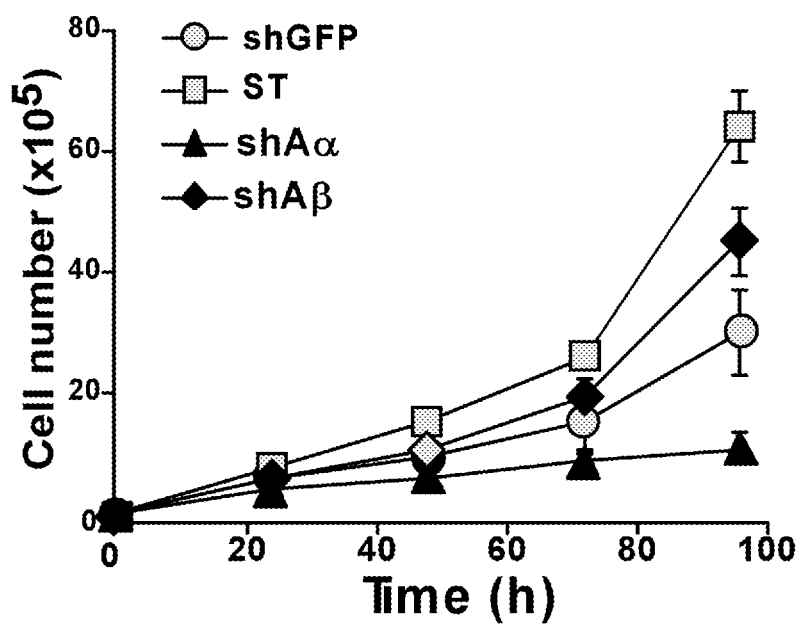
Figure 1F:
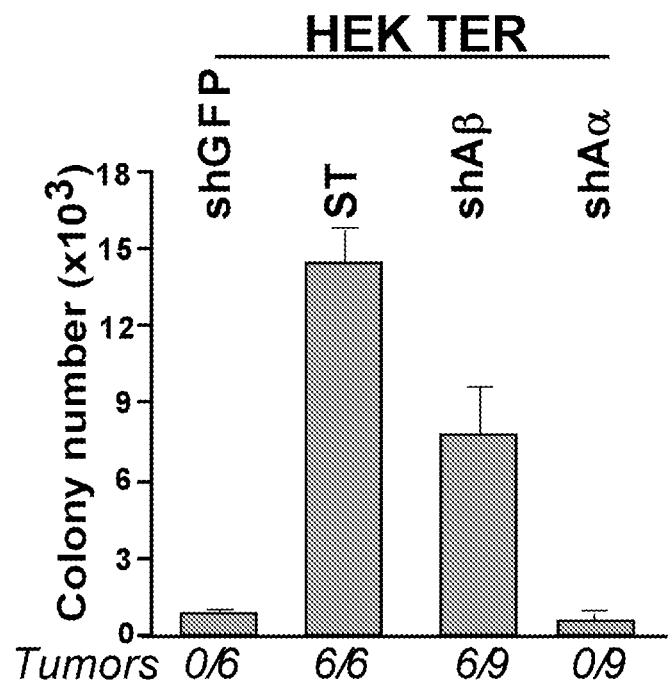
Figure 1G:
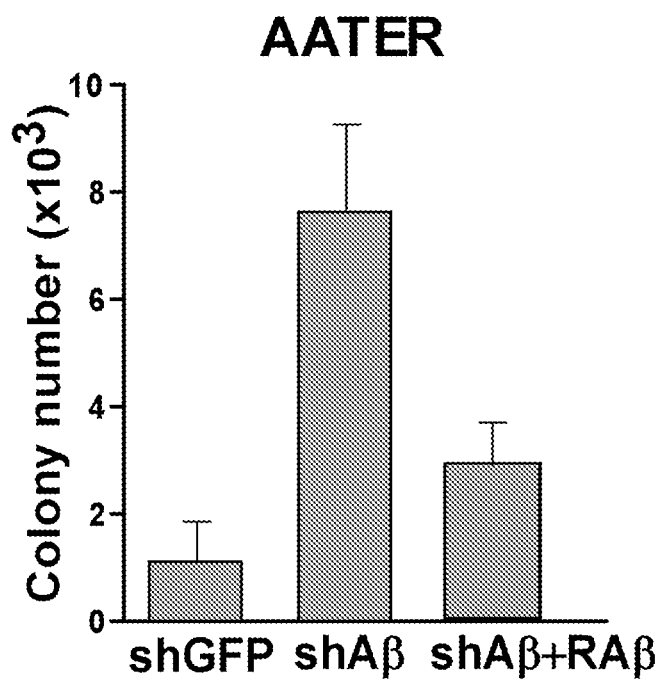
Figure 1H:
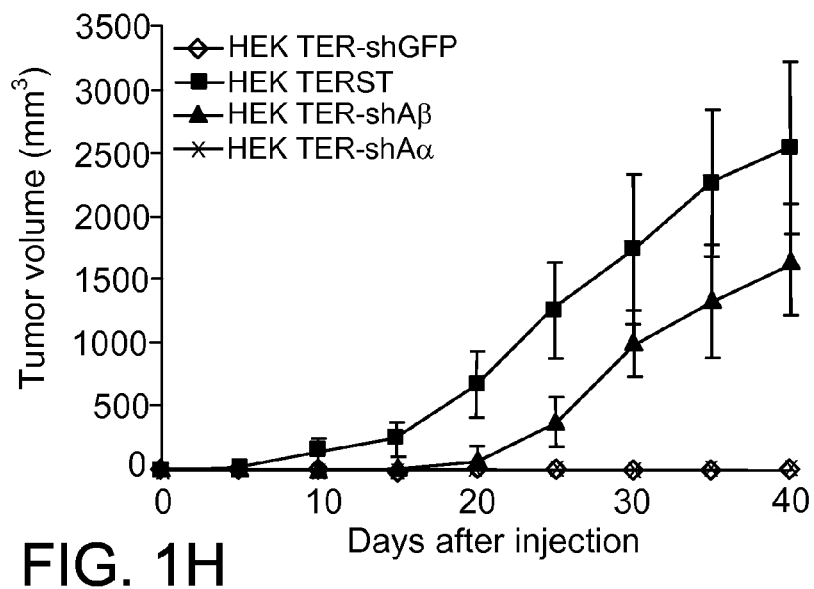

As shown in FIGS. 1E, 1F, and 1H, we found that HEK TER cells expressing very low levels of Aα proliferated poorly and failed to grow in an AI manner or to form tumors, in agreement with our previously published work (Chen et al, *Cancer Res.*, 65:127-136, 2005). In contrast, suppression of the PP2A Aβ subunit induced an increase in the rate of proliferation (see FIG. 1E), conferred the ability to grow in an AI manner (see FIG. 1F), and permitted these cells to form tumors (FIGS. 1F and 1H).

Figure 1I:
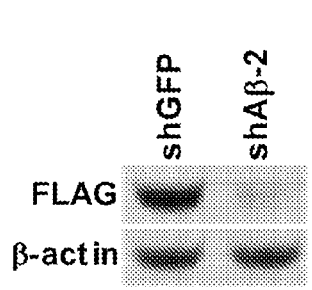
Figure 1J:
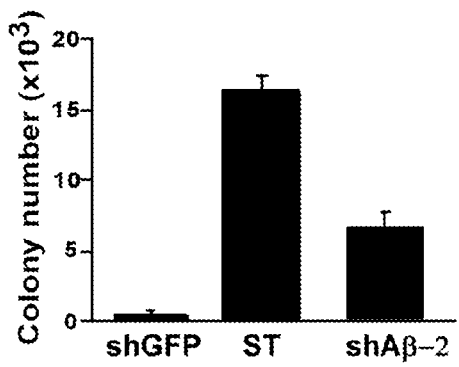

To exclude the possibility that these observations were due to off-target effects of RNAi, we used a second shRNA targeted to a different region of the PP2A Aβ mRNA (shAβ2), described supra. As show in FIG. 1I and consistent with FIG. 1A, shAβ2 also efficiently suppressed wtPP2A Aβ expression in HEK TER cells, As shown in FIG. 1J and consistent with FIG. 1F, shAβ2 also permitted cell growth in an AI manner.

Figure 1K:
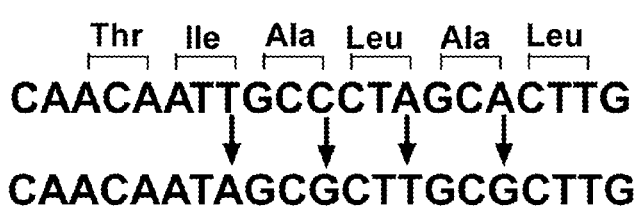

To further demonstrate the specificity of the above observations, a mutant PP2A Aβ allele (shown in FIG. 1K) that is resistant to suppression by shAβ was designed by inserting silent substitutions into the PP2A Aβ sequence targeted by shAβ (nucleotides 172-192 in SEQ ID NO:2, as described above) and generated using the QuickChange® Multi Site-Directed Mutagenesis kit, according to the Manufacturer's instruction (Stratagene, La Jolla, Calif.). FLAG-tagged mutant-PP2A Aβ (designated mutPP2A Aβ and RAβ) was generated as described supra for wtPP2A Aβ.

Figure 1L:
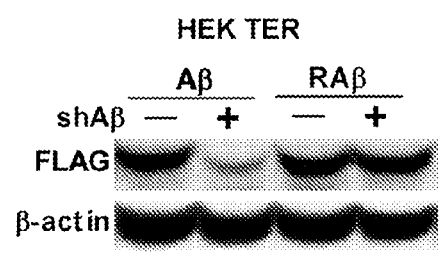
Figure 2A:
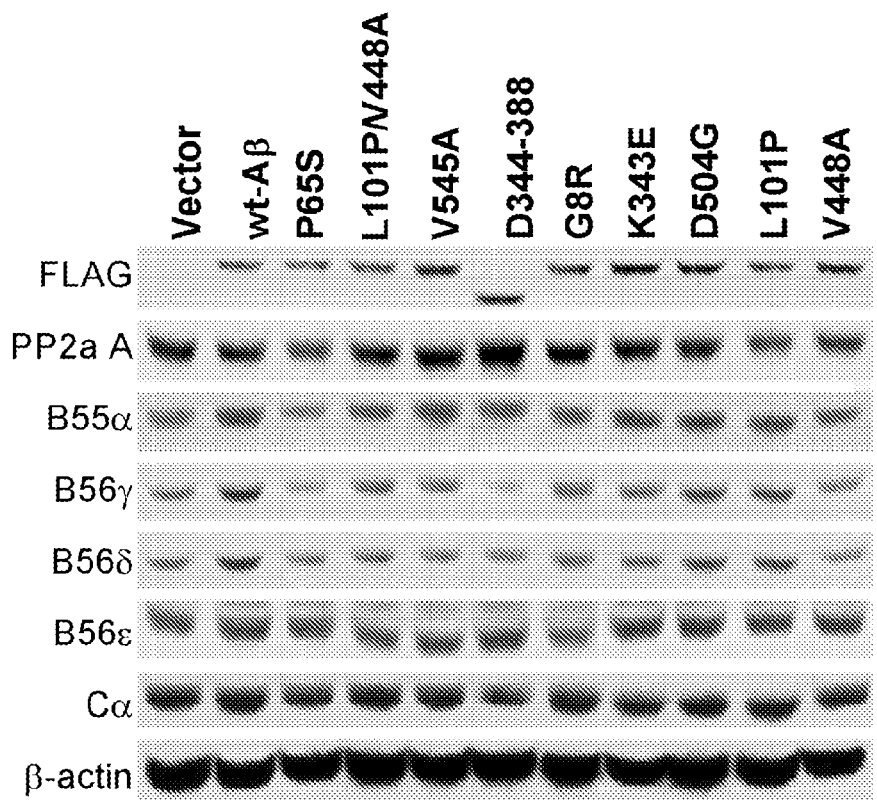
FIGS. 2A-2F show PP2A subunit association and activity. (A) Immunoblot showing PP2A FLAG-taggged wild type and mutant Aβ expression in HEK TER cells. (B) Immunoblot showing immunoprecipitation of FLAG-tagged PP2A Aβ wild type and mutants to PP2A subunits B55α, B56α, B56γ, B56δ, B56ε, and Cα. Immunoprecipitation was performed with anti-FLAG antibody. Immunoblotting was preformed with antibodies specific for B55α, B56α, B56γ, B56δ, B56ε, Cα and FLAG. (C) Immunoblot showing binding of Aβ mutants to PP2A catalytic subunit (bottom panel) and bar graph showing phosphatases activity of PP2A-specific complexes containing Aβ mutants (top panel). Immune complexes were precipitated using FLAG antibody and immunoblotting was performed using anti-FLAG, Cα, or β-actin antibodies. Aβ-specific phosphatases activity was determined in immune complexes by measuring $PO_4^{3-}$ release from the substrate phosphopeptide [RRA(pT)VA]. (D) Immunoblot showing expression of RAβ shAβ resistant forms in HEK TER-shAβ cells (bottom panel) and bar graph showing AI growth and tumor formation (top). Tumors were reported as the number of tumors formed per the number of injection sites. (E) Line graph showing the proliferation rate of HEK TER-shAβ cells expressing control vector or PP2A Aβ mutant alleles that are resistant to shAβ. SV40 ST expressing HEK TER cell line was used as control. Data is mean±SD for three independent experiments. (F) Line graph showing kinetics of tumor growth in (E). 9 xenografts per cell line were studied.

As shown in FIG. 1L, in contrast to overexpressed wtPP2A Aβ, overexpressed mut-PP2A Aβ was resistant to suppression by shAβ. Furthermore, as shown in FIG. 1G and FIG. 2D, mut-PP2A Aβ reversed the observed transformed phenotype. Moreover, we found that suppression of Aβ expression in immortal, human small airway epithelial cells expressing hTERT, LT, and H-RAS (AATER cells), previously described (Lundberg et al., Oncogene, 21:4577-4586, 2002), also permitted AI growth (FIG. 1G). Importantly, this final observation strongly indicates that the observations described above following Aβ suppression are not cell type specific.

Taken together, these results strongly suggest that loss of PP2A Aβ expression contributes directly to cell transformation.

Example 2

Cancer-Associated PP2A Aβ Mutants are Functionally Defective

Mutations in PP2A Aβ are found in lung, breast and colon cancers and include missense mutations involving P65S, L101P, V448A, V545A, G8R, K343E and L101P/V448A (Wang et al., Science, 282:284-287, 1998). In addition, one PP2A Aβ mutation involves the deletion of exon 9, resulting in an in-frame deletion of 45 amino acids (ΔE344-E388). To study the function of these cancer-associated mutants, we generated cancer-derived FLAG-tagged Aβ mutants, using the methods described in Example 1. Cancer-derived FLAG-tagged Aβ mutants were designated P65S, L101P/V448A, V545A, D344-388, G8R, K343E, D504G, L101P, and V448A.

These mutant Aβ alleles were subsequently overexpressed in HEK TER cells and analyzed using SDS-PAGE, as described in Example 1. Membranes were then probed with antibodies specific to FLAG, PP2a A (clone 6G3), B55α, B56γ, B56δ, B56ε, Cα described in Example 1 and β-actin (Sigma-Aldrich Co., St. Louis, Mo.) to confirm expression, as shown in FIG. 2A. Next the ability of these constructs to form functional PP2A complexes was assessed using immunoprecipitation, as follows.

Briefly, cells were lysed in a buffer containing 50 mM Tris-HCl, pH 7.5, 150 mM NaCl, 1 mM EDTA, protease inhibitor cocktail and 0.3% CHAPS. Cell lysates (2 mg) were incubated with the FLAG M5 or Aα (clone 6F9) antibody overnight at 4° C., followed by the addition of protein G Sepharose beads (Amersham, Piscataway, N.J.) for 2 h at 4° C., or overnight at 4° C. with FLAG-agarose (M2) or HA-agarose (HA7) (Sigma Aldrich). The beads were washed 3 times with lysis buffer and eluted with 3× FLAG peptide (150 ng/μl), 0.1M glycine (pH 3.5) or 2× SDS sample buffer, followed by SDS-PAGE and immunoblotting, as described in Example 1. Membranes were then probed with antibodies specific to FLAG, PP2a A (clone 6G3), B55α, B56γ, B56δ, B56ε, Cα described in Example 1 and β-actin (Sigma-Aldrich Co., St. Louis, Mo.).

Figure 2B:
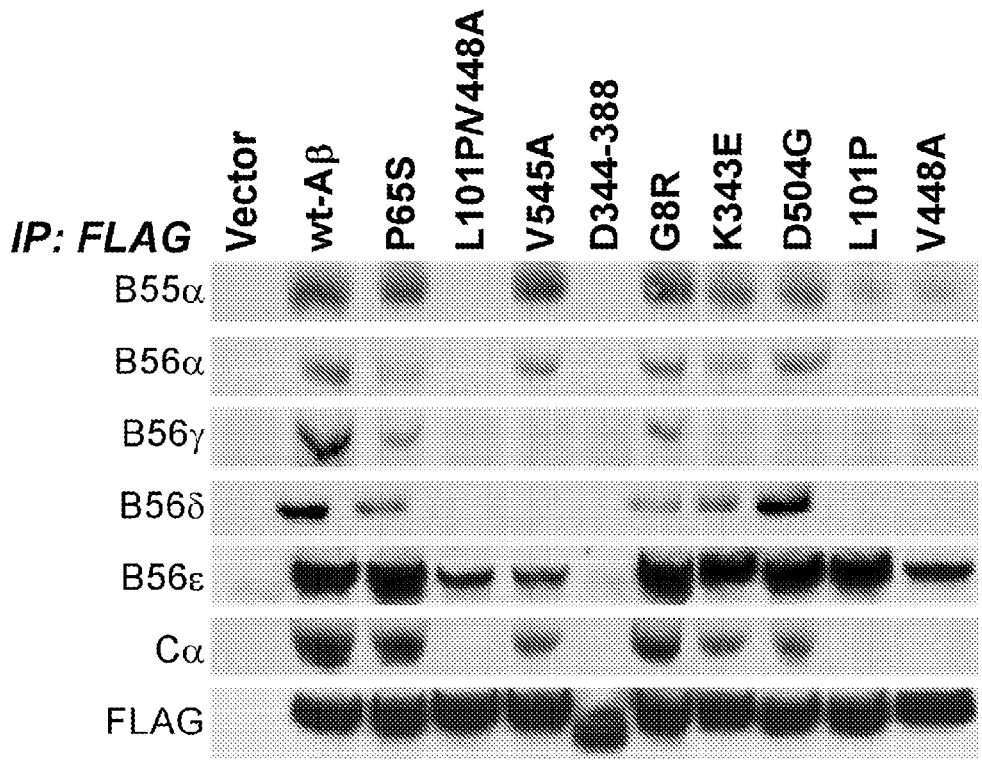
Figure 2C:
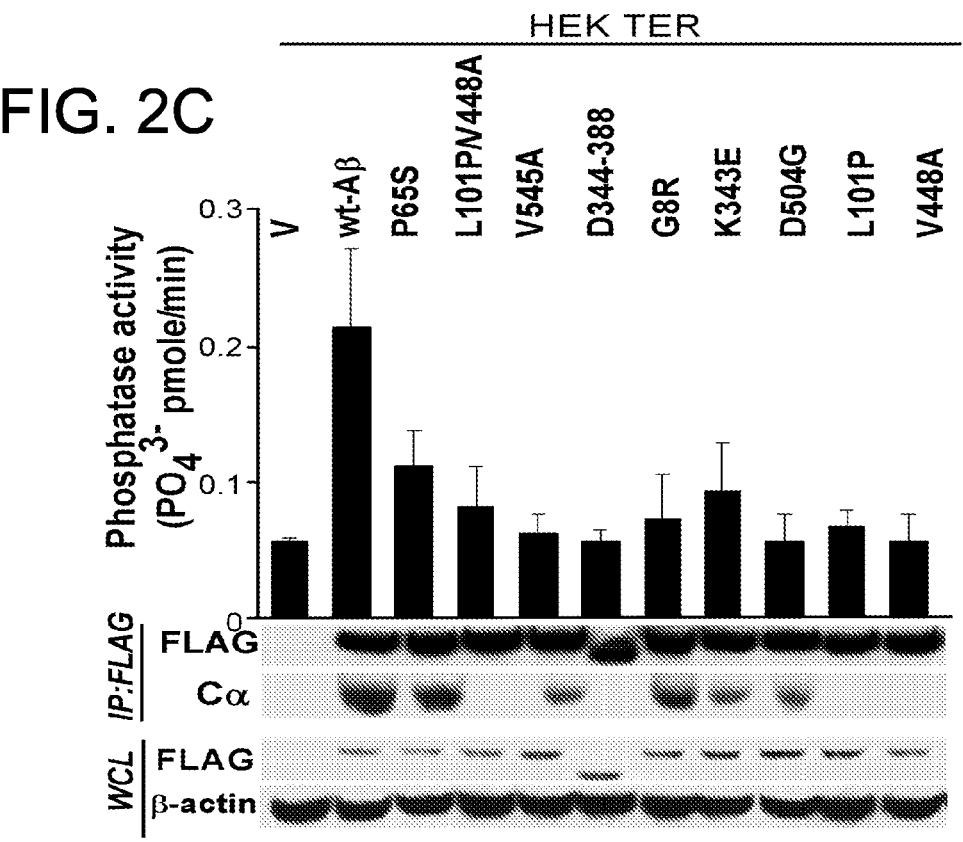
Figure 2D:
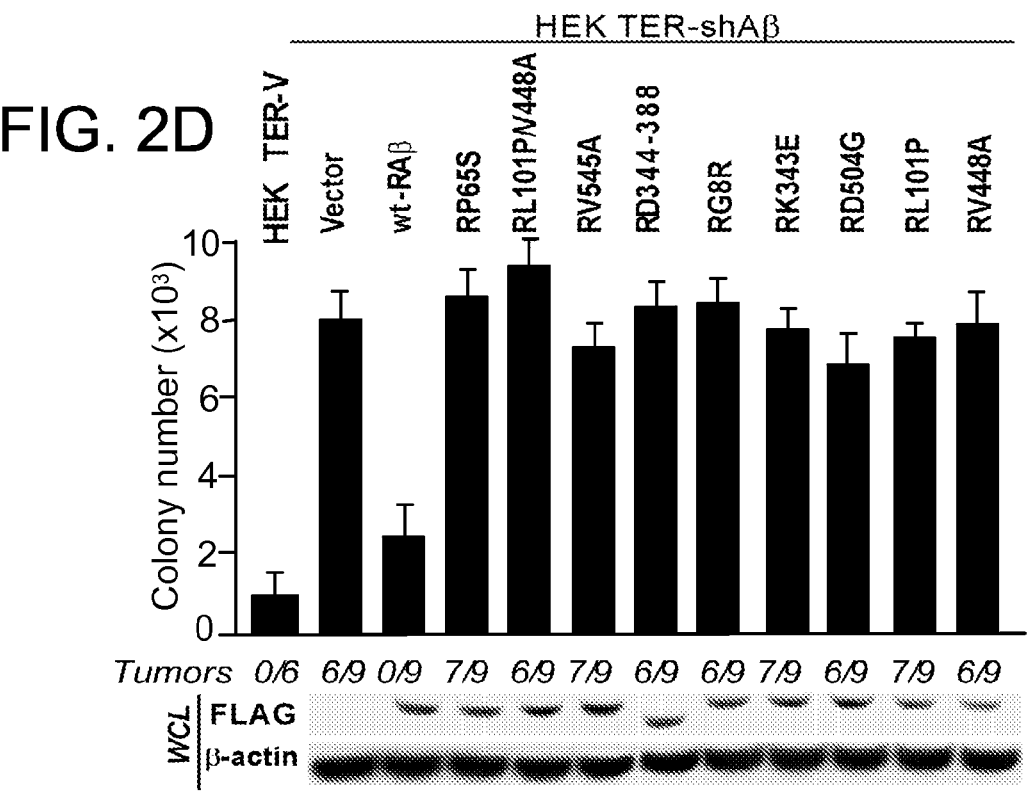

As shown in FIGS. 2B and 2C (lower panel), of the Aβ immune complexes, we found that wtPP2A Aβ formed heterotrimers with the catalytic Cα and each of the regulatory B subunits tested. In contrast, each of the cancer-derived Aβ mutants showed clear defects in their ability to form PP2A complexes, in agreement with previous reports (Ruediger et al., Oncogene, 20:1892-1899, 2001).

We next determined whether these Aβ mutants retained phosphatase activity by measuring PP2A Aβ-attributable phosphatase activity in Aβ immune complexes isolated from HEK TER cells expressing wtPP2A Aβ or mutant PP2A forms of Aβ using a previously described method (Chen et al., Cancer Cell, 5:127-136).

As shown in FIG. 2C, the phosphatase activity associated with the mutant Aβ immune complexes P65S, V545A, G8R, K343E and D504G was reduced by 48±5%, 70±7%, 68±9%, 52±4%, or 71±9% respectively, compared to the activity levels found with the WT Aβ subunit. We failed to detect any Aβ-attributable phosphatase activity in cells expressing the Aβ mutants L101P/V448A, ΔE344-E388, L101P, and V448A. Thus, we concluded that cancer-associated mutations of PP2A Aβ mutants fail to form the full compliment of PP2A complexes and demonstrate impaired mutant-specific phosphatase activity.

Example 3

Loss-of-Function of Both Aβ Alleles is Necessary to Transform Human Cells

To determine whether Aβ mutants exhibit gain of function properties, we measured the total PP2A-specific phosphatase activity in cells overexpressing WT Aβ or Aβ mutants from whole cell lysates, as described in Example 1.

Figure 3:
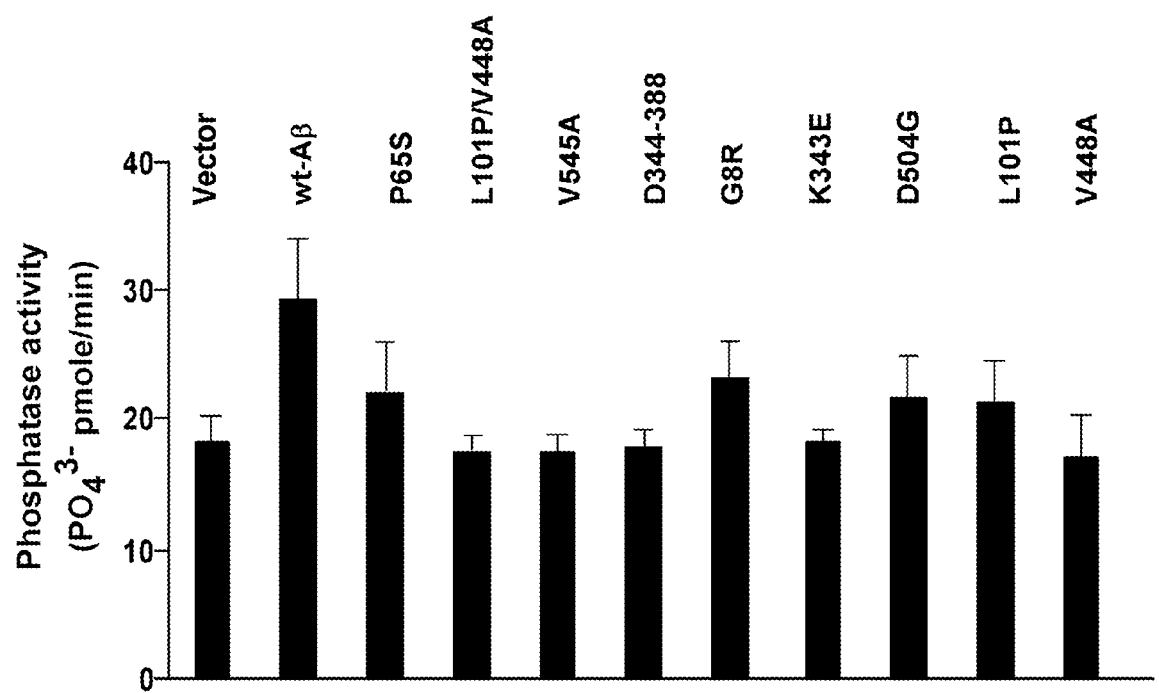
FIG. 3 shows phosphatases activity in HEK TER cells expressing wild type PP2A Aβ and the mutant PP2A Aβ constructs. PP2A-specific phosphatase activity was determined in whole cell lysates by measuring the release of $PO_4^3$ from the substrate [RRA(pT)VA]. Mean±SD are shown for 3 independent experiments.

As shown in FIG. 3, introduction of wtPP2A Aβ or the P65S or G8R Aβ mutants resulted in a slight increase in total phosphatase activity, while no changes in overall activity were found in cells expressing other Aβ mutants. This observation suggests that PP2A Aβ mutants did not disrupt endogenous phosphatase activity by acting as dominantly acting negative alleles. Moreover, introduction of the WT allele of PP2A Aβ or any of the mutant PP2A Aβ alleles into immortalized but non-tumorigenic HEK TER cells failed to transform these cells, confirming that these mutations fail to act as dominant oncogenes.

Figure 2E:
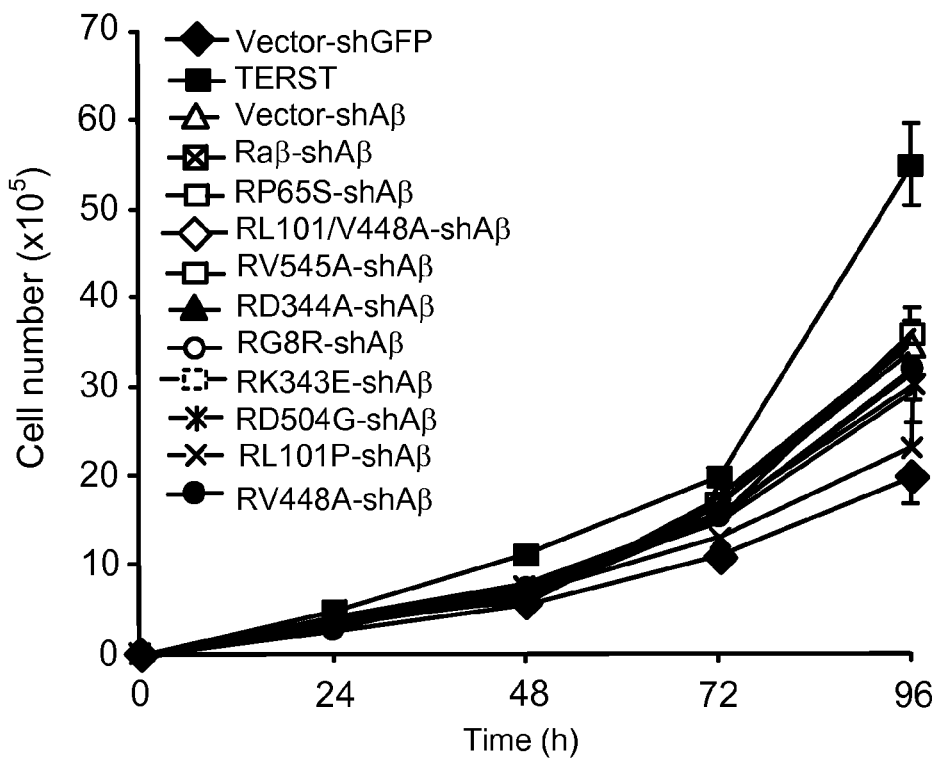
Figure 2F:
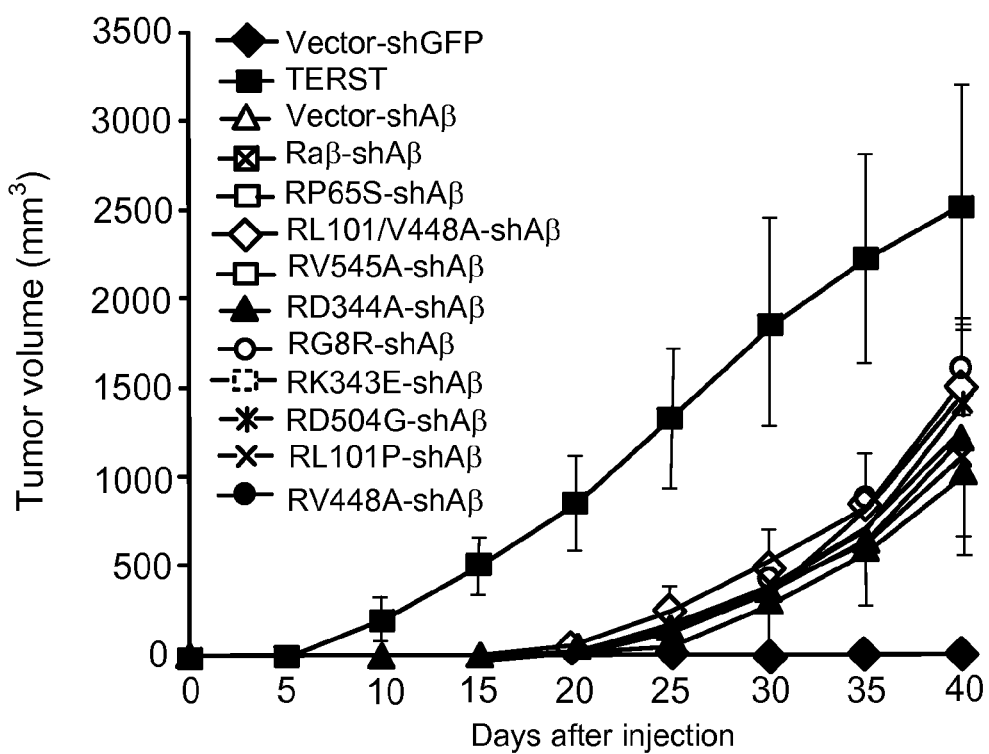

Consistent with these observations, Aβ mutant alleles are usually accompanied by the deletion of the second allele in human tumor samples (Tamaki et al., Oncol. Rep., 11:655-659, 2004; Wang et al., Science, 282:284-287, 1998). In an attempt to mimic this situation, we expressed mutPP2A Aβ (RAβ), described in Example 1, in HEK TER-shAβ cells. As shown in FIG. 2D lower panel and consistent with FIG. 1L, RAβ is insensitive to stable shAβ expression in tumorigenic HEK TER-shAβ cells. In addition, as shown in FIG. 2E, RAβ expression decreased cell proliferation by 36%. In contrast, expression of each of the Aβ mutants failed to alter substantially the proliferation rate of shAβ cells. Introduction of RAβ in HEK TER-shAβ or AATER-shAβ cells also significantly suppressed AI growth (62±8% and 67±9%, respectively) and reduced the number of tumors formed, whereas introduction of other Aβ mutants showed no inhibitory effects on the transformed phenotype (FIGS. 1G, 2D, and 2F). Taken together, these observations confirmed that each of cancer-associated PP2A Aβ mutants is a functionally null allele and that loss-of-function of both Aβ alleles is necessary to induce a fully transformed phenotype.

Example 4

Figure 4A:
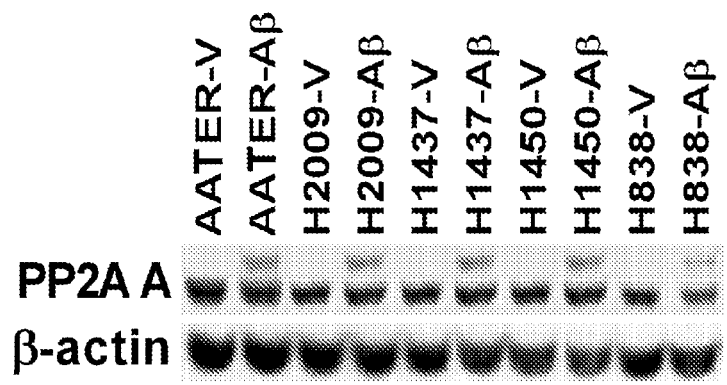
FIGS. 4A-4D include an immunoblot, line graphs, and a bar graph showing proliferation, AI growth, and tumorgenicity. (A) Immunoblot showing wtPP2A Aβ expression in AATER and lung carcinoma cells (H1437, H2009, H1450, and H838). Aβ expression was confirmed by immunoblotting using a pan-PP2A A subunit specific antibody. (B) Line graphs showing cell proliferation rates in AATER and lung cancer cells described in (A) expressing wtPP2A Aβ. Population doubling (PD) is previously defined (Chen et al., *Cancer Res.*, 65:127-136, 2005). (C) bar graph showing AI growth rates in AATER and lung cancer cell lines described in (A). *=p<0.0008 and **=p<0.0019 as determined using the Student's t-test. (D) Line graph showing kinetics of tumor growth of H2009 and H1450 cells expressing a control vector or wtPP2A Aβ. 6 xenografts for each cell line were studied. *=p<0.83. **=p<0.039, as determined by ANOVA. V=control vector. Data for B, C, and D shown mean±SD for 3 independent experiments.

Restoration of Aβ Function in Lung Carcinoma Cells Reverses the Tumorigenic Phenotype To investigate the role of PP2A Aβ mutations in patient-derived cancer cell lines, we determined the effects of restoring PP2A Aβ function in lung cancer cell lines that harbor PP2A Aβ mutations. The H1450 and H838 lung cancer cell lines harbor PP2A Aβ subunit mutations (Wang et al., *Science*, 282:284-287, 1998). The H1450 cell line carries one Aβ allele containing an in-frame deletion of residues 717-1583 and a second allele with point mutation D504G, while H838 harbors only one mutant Aβ allele (G8R). To examine whether expression of the Aβ subunit reverses the tumorigenic phenotype, we introduced the wtPP2A Aβ allele into these lung cancer cell lines harboring mutant PP2A Aβ and confirmed their expression using immunoblotting, as described in Example 1 (FIG. 4A). As control, we used the primary AATER cells and two lung carcinoma cell lines—H1437 that harbors two WT Aβ alleles and H2009 that has one WT Aβ allele and a G90D Aβ allele. When overexpressed, the Aβ G90D allele behaved in a manner indistinguishable from wtPP2A Aβ with regard to forming active PP2A complexes and suppressing AI growth.

Cell cycle and apoptosis in the each of the above described cells lines was analyzed, as follows. Cells were incubated with BrdU and then with fixed in 70% ethanol overnight. Fixed cells were subsequently double stained with PI and anti-BrdU antibodies (BD Biosciences), and cell cycle distribution was determined using flow cytometry. To detect apoptotic cells, attached and floating cells were harvested, washed with PBS and stained by binding buffer containing FITC-conjugated Annexin V (Calbiochem, La Jolla, Calif.) and PI. Apoptotic cells were quantitated by fluorescence-activated cell sorting and analyzed by CellQuest software.

Figure 4B:
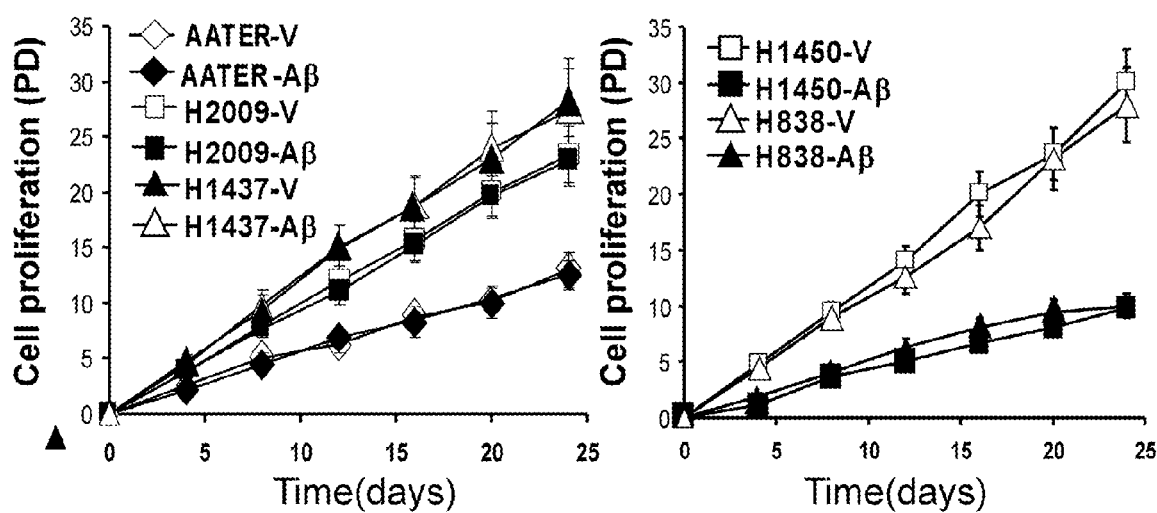
Figure 4C:
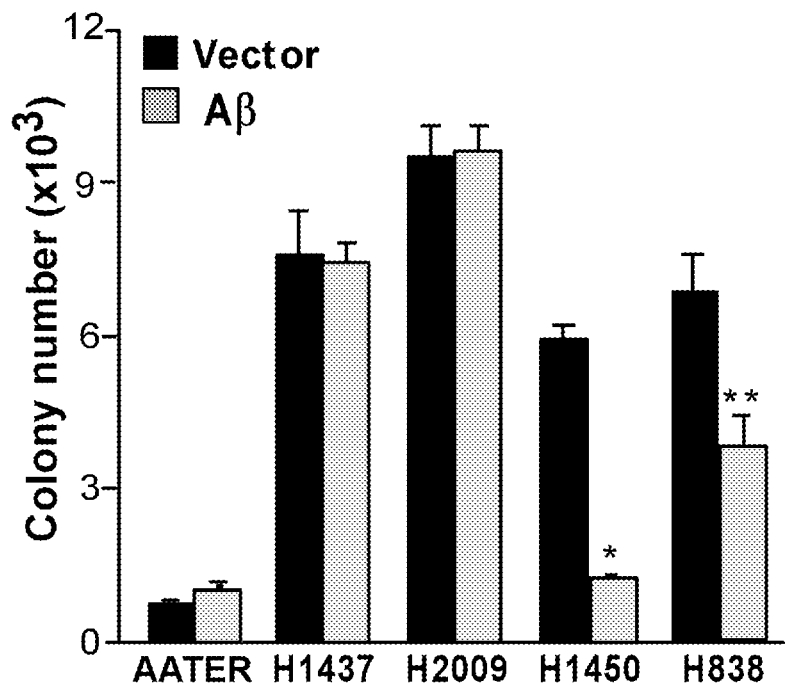
Figure 4D:
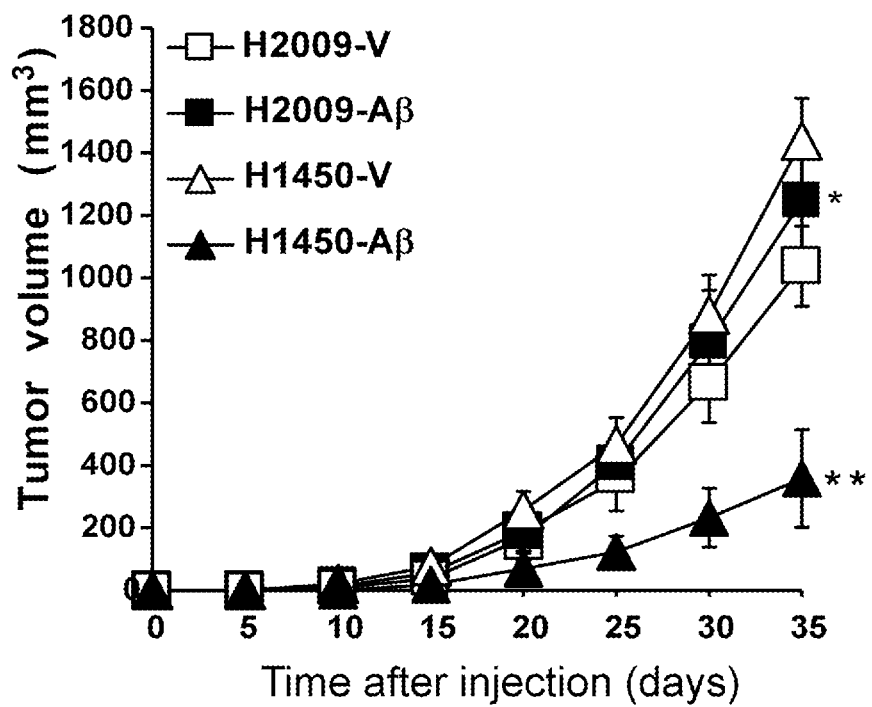

As shown in FIG. 4B and Table 1, expression of wtPP2A Aβ in the H1450 and H838 cell lines suppressed their doubling rate by 68±8% and 58±9%, respectively and reduced the number of AI colonies formed by these cell lines by 77±8% and 42±5%, respectively (FIG. 4C). Furthermore, WT Aβ expression in H1450 cells significantly suppressed tumor growth (FIG. 4D). In contrast, introduction of WT Aβ into the H1437, H2009 or AATER cell lines, each of which carries a WT Aβ allele, failed to inhibit cell proliferation, AI growth or tumor growth, suggesting that the decreased cell proliferation and AI growth observed in H1450 and H838 cells was not an artifact induced by overexpression of Aβ (FIGS. 4B-4D and Table 1).

As shown in Table 1, cell cycle analysis by double 5-bromo,3'-deoxyuridine/propidium iodide (BrdU/PI) staining showed that the introduction of wtPP2A Aβ into H838 and H1450 cells increased the percentage of cells present in the G1 phase of the cell cycle. In contrast, expression of wtPP2A Aβ failed to affect the cell cycle distribution of AATER, H1437 and H2009 cells. In addition, we did not detect any evidence of increased apoptosis following wtPP2A Aβ overexpression, suggesting that the decreased proliferative rate induced by wtPP2A Aβ in lung carcinoma cell lines harboring mutant Aβ was due to the lengthening of cell cycle rather than apoptosis.

Example 5

Suppression of PP2A Aα or Aβ Induces Transformation by Distinctive Mechanisms We previously reported that partial suppression of PP2A Aα imparts a tumorigenic phenotype by selectively eliminating PP2A B56γ containing complexes (Chen et al., *Cancer Cell*, 5:127-136, 2004). Although the two distinct PP2A A isoforms, Aα and Aβ, share 86% sequence identity (Hendrix et al., *J. Biol. Chem.*, 268:15267-15276, 1993), it remained unclear whether these isoforms share overlapping functions. To determine, therefore, if Aα and Aβ are interchangeable, we overexpressed Aα in HEK TER, cells in which we suppressed Aβ expression (HEK TER-shAβ), as described in Example 1. Cells were then analyzed as described in Example 1.

Figure 5A:
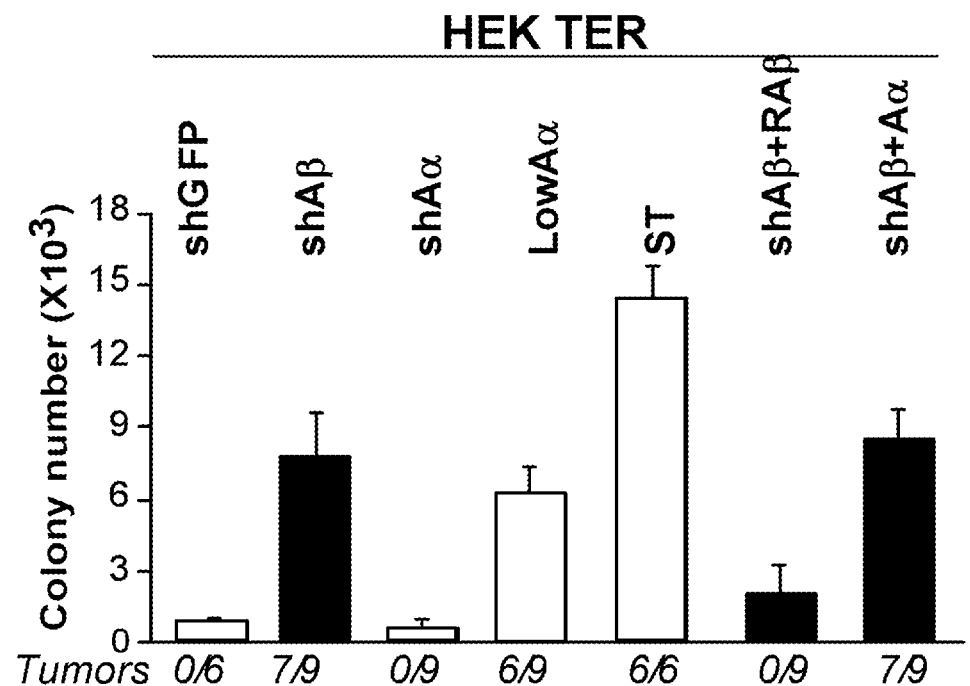
FIGS. 5A-5C include a bar graph, a line graph, and an immunoblot showing AI growth and tumor formation, tumor growth kinetics and a co-immunoprecipitation, respectively. (A) Bar graph showing AI growth and tumor formation of HEK TER cells expressing shGFP, shAβ, shAα (shAα and low Aα cell lines refer to cells that exhibit 90% and 50% suppression of Aα expression, respectively), or SV40 ST. AI colonies formed is presented as mean±SD for 3 independent experiments. Tumors are reported as the number of tumors formed per number of injection sites. (B) Line graph showing tumor growth kinetics in cells with suppressed PP2A Aα and Aβ. shGFP n=9; shAβ n=9; and shAα n=9. shAα and low Aα cell lines refer to cells that exhibit 90% and 50% suppression of Aα expression, respectively. SV40 ST (n=6) and HEK TER-shAβ cells expressing shAβ-resistant wtPP2A Aβ or Aα were injected subcutaneously and xenograft growth was analyzed biweekly. (C) Immunoblot showing interaction between SV40 ST and PP2A structural subunits.
Figure 5B:
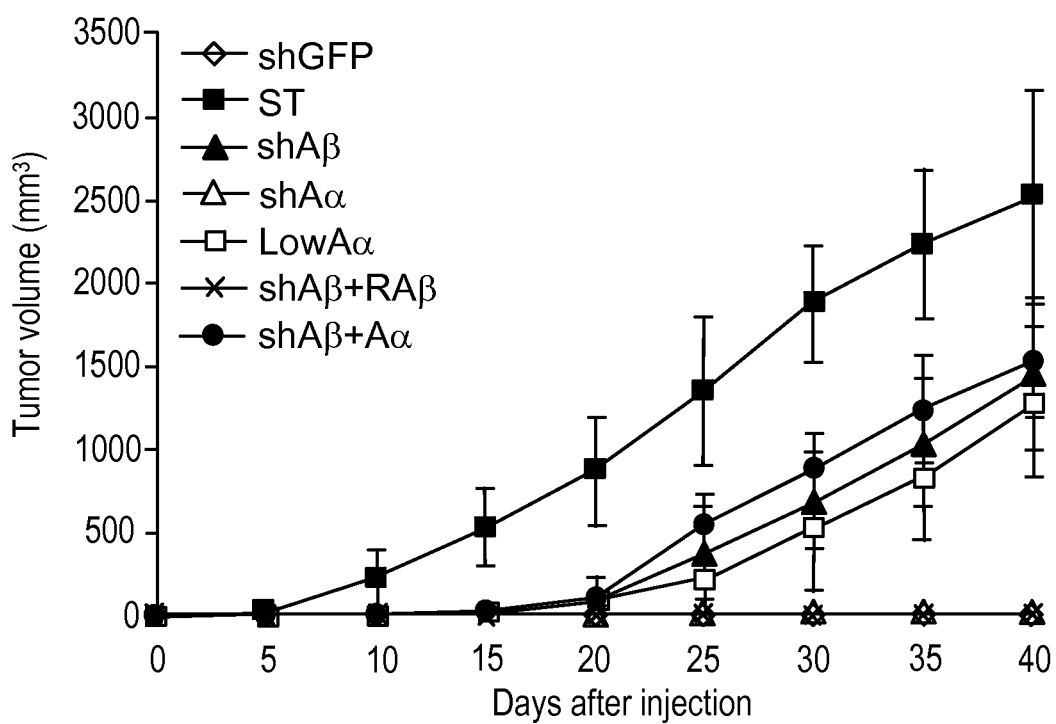

As shown in FIGS. 5A and 5B, PP2A Aα overexpression in HEK TER-shAβ cells failed to revert the transformed phenotype induced by Aβ suppression, indicating that the Aα isoform does not functionally substitute for loss of Aβ expression (FIG. 3A). Interestingly, consistent with our previous observation (Chen et al., *Cancer Cell*, 5:127-136, 2004), partial suppression of PP2A Aα imparts a tumorigenic phenotype.

To investigate the association between ST and PP2A Aα and Aβ, GST-tagged ST was mixed with 293T cell lysates containing control vector (Vector), FLAG-tagged Aα or FLAG-tagged Aβ. The ST-containing complexes were isolated with glutathione-agarose followed by immunoblotting using an affinity-purified polyclonal antibody raised against ST peptides or the polyclonal anti-FLAG antibody described in Example 1.

TABLE 1

Effects of wtPP2A Aβ Expression on Cell Cycle and Apoptosis

| Cell Line | Doubling Time (h) | G0/G1 (%) | S (%) | G2/M (%) | Apoptotic Cells (%) |
|---|---|---|---|---|---|
| AATER-V | 55 ± 9 | 55.4 ± 9.3 | 22.5 ± 4.3 | 22.1 ± 3.6 | 4.5 ± 0.5 |
| AATER-Aβ | 58 ± 8 | 58.3 ± 7.7 | 20.4 ± 3.1 | 21.3 ± 2.3 | 4.6 ± 0.3 |
| H1437-V | 21 ± 3 | 33.5 ± 5.3 | 42.6 ± 5.6 | 23.9 ± 2.5 | 2.3 ± 0.5 |
| H1437-Aβ | 41 ± 5 | 35.5 ± 4.4 | 45.9 ± 4.2 | 18.8 ± 2.4 | 3.5 ± 0.8 |
| H2009-V | 24 ± 3 | 51.3 ± 5.7 | 28.5 ± 2.7 | 20.2 ± 4.9 | 5.3 ± 0.6 |
| H2009-Aβ | 25 ± 1 | 53.5 ± 6.8 | 27.7 ± 1.8 | 19.9 ± 2.9 | 4.9 ± 0.5 |
| H1450-V | 20 ± 4 | 40.3 ± 5.5 | 33.5 ± 2.7 | 26.2 ± 4.7 | 5.3 ± 0.6 |
| H1450-Aβ | 53 ± 6 | 73.5 ± 9.6** | 8.7 ± 1.8** | 17.8 ± 2.9 | 4.9 ± 0.5 |
| H838-V | 22 ± 3 | 46.7 ± 6.6 | 36.4 ± 5.2 | 16.9 ± 2.6 | 3.8 ± 0.4 |
| H838-Aβ | 41 ± 6 | 75.3 ± 6.8** | 8.9 ± 1.2** | 15.8 ± 2.3 | 4.1 ± 0.5 |

Table 1 shows the proliferation rate of lung carcinoma cell lines expressing control vector (V) or wtPP2A Aβ (Aβ). Data shown as mean ± Standard Deviation (SD).
**= $p < 0.01$ as determined using Student's T-test.

Figure 5C:
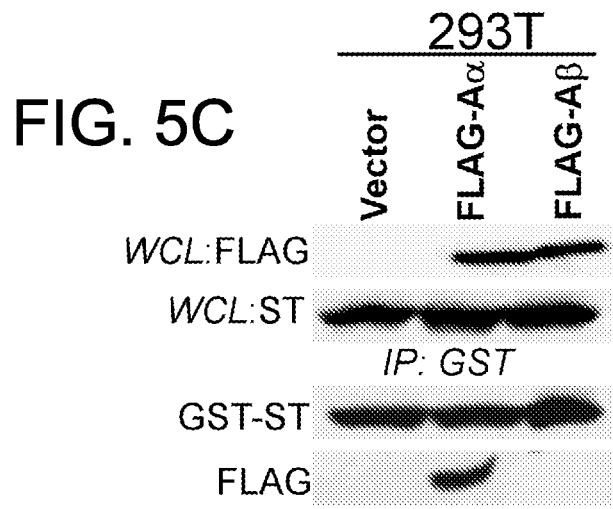

As shown in FIG. 5C, only the PP2A Aα isoform forms complexes with ST, consistent with previous reports (Zhou et al., Biochem., 369:387-398, 2003). Together, these observations indicate that suppression of Aβ induces transformation by a mechanism distinct from that caused by partial depletion of PP2A Aα or by expression of ST.

Example 6

The Small GTPase RalA Interacts with PP2 Aβ

To study the mechanism by which PP2A Aβ suppression contributes to transformation, we purified PP2A Aα and Aβ complexes and identified the proteins that bind uniquely to Aβ.

Figure 6A:
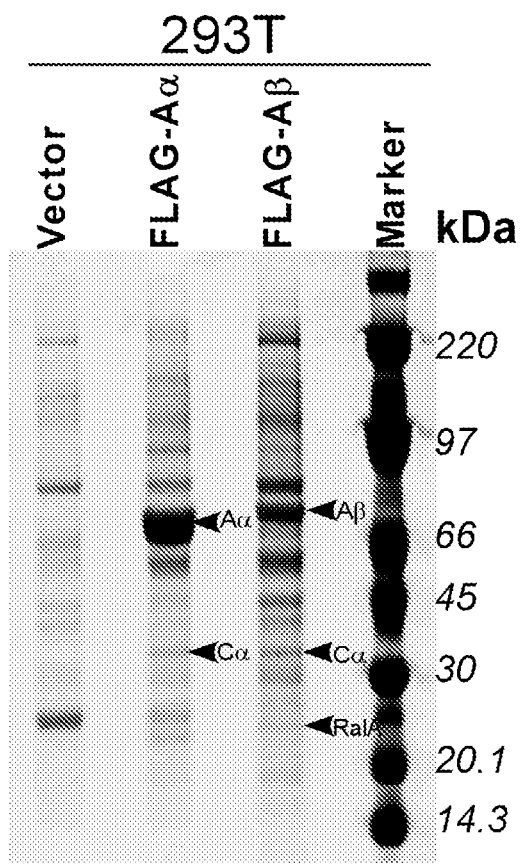

More specifically, FLAG-epitope tagged Aα (wtPP2A Aα), generated as described for wtPP2A Aβ in Example 1, and wtPP2A Aβ were overexpressed in HEK 293T cells. Cells were lysed as described in Example 1, and large scale immunoprecipitations were performed using anti-FLAG (M2) agarose. Proteins in the precipitated immune complexes were then resolved using SDS PAGE and stained with coomassie blue, as shown in FIG. 6A. Mass spectroscopy was then performed to identify interacting proteins and the data for which is presented in FIG. 6B.

As shown in FIGS. 6A and 6B, analysis of the samples described above identified the PP2A catalytic Cα and several regulatory B subunits associated with both the Aα- and Aβ-specific complexes; confirming that these conditions permitted the isolation of functional heterotrimers. Furthermore, although most proteins identified interacted with both Aα and Aβ, a small number of proteins were identified that bound exclusively to PP2A Aβ. These results were confirmed using immunoprecipitation and immunoblotting as described in Example 1. Briefly, wtPP2A Aα and wtPP2A Aβ were over expressed in 293T cells. Immunoprecipitations were then performed using anti-FLAG (M2) agarose and membranes were probed using commercially available FLAG (M2), SG2NA, cdc2, cdk4, HDAC1, RalA, and FGFR1-OP specific antibodies (FIG. 6C). Immunoblots were also performed using just RalA and FLAG (M2) specific antibodies (FIG. 6D).

Figure 6D:
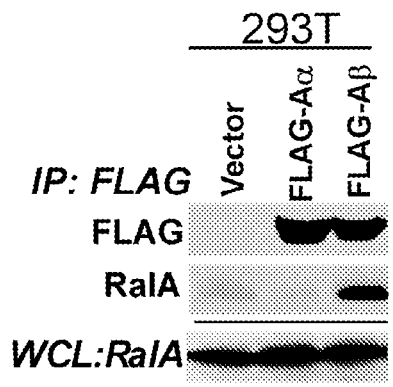

As shown in FIGS. 6C and 6D, the small GTPase protein RalA was the only protein that specifically formed complexes with Aβ subunit.

RalA has been implicated in the regulation of exocytosis, transcription, secretion, cell transformation and tumor progression (Feig L. A., Trends Cell Biol., 13:419-425, 2003; Feinstein E., Oncogene, 24:326-328, 2005).

To further confirm the observed association between PP2A Aβ and RalA reciprocal co-immunoprecipitation experiments were performed using overexpressed wtPP2A Aβ and HA-tagged RalA, as follows.

HA-tagged wild-type RalA were generated in the retroviral vectors pPs-neo and pBabe-puro. Overexpressed FLAG-tagged Aβ and HA-tagged RalA in 293T cells were subjected to immunoprecipitation with anti-HA agarose, or anti-FLAG-agarose. The supernatants from the first immunoprecipitation were sequentially incubated with anti-FLAG-agarose (M2), or anti-HA-agarose (HA7) in reciprocal manner. The proteins eluted from the beads were separated by SDS-PAGE and revealed by immunoblotting using HA and FLAG antibodies. Densitometry analysis was performed by using Scion Image Software.

Figure 6E:
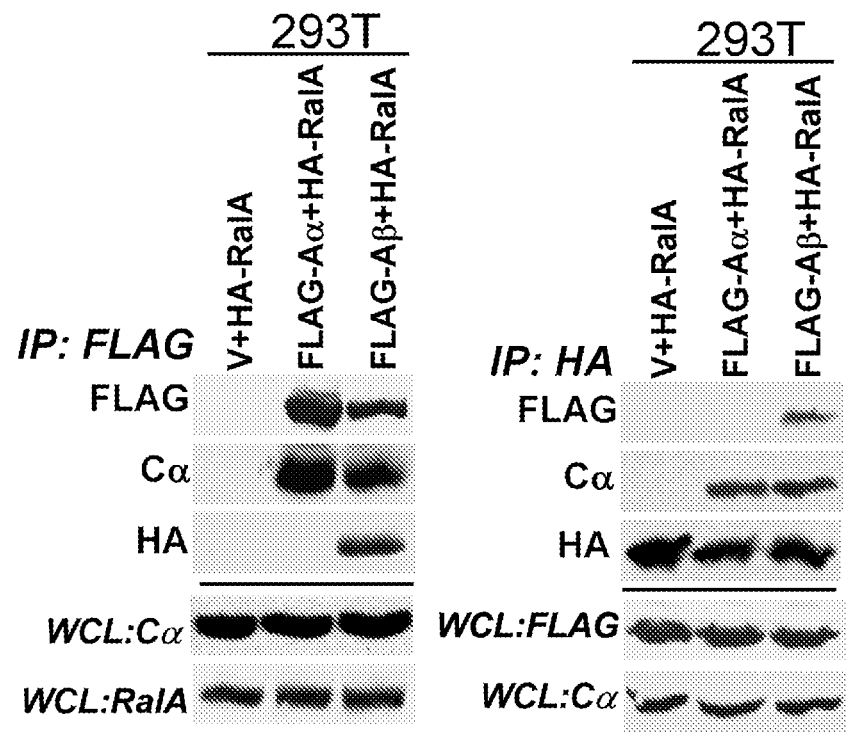

As shown in FIG. 6E, when we overexpressed HA-tagged-RalA and FLAG-tagged Aβ in 293T cells, we found that immune complexes isolated using either HA- or FLAG-specific antibodies contained both RalA and Aβ. As shown in FIGS. 6C and 6D, endogenous RalA also interacted with wtPP2A Aβ in 293T cells. In contrast, PP2A Aα failed to form complexes with RalA, confirming that RalA specifically binds PP2A Aβ-containing complexes.

To determine the subcellular localization of RalA and PP2A Aα and Aβ proteins, soluble and membrane fractions were isolated from 293T cells overexpressing a control vector (GFP), wtPP2A Aα, or wtPP2A Aβ. Cell lysates were then collected as described in Example 1. Membrane-rich fractions of proteins where then purified using ProteoExtract Membrane Protein Extraction kit, according to the Manufacturer's instructions (Calbiochem). Proteins were resolved as described in Example 1 and immunoblot analysis was performed using antibodies specific to FLAG, RalA, or β-actin.

As shown in FIG. 6F, both RalA and wtPP2A Aβ were found in the membrane fraction of HEK TER-Aβ cells.

Quantitative immunoprecipitations were performed using protein overexpression as described above coupled with densitometry analysis performed using Scion Image Software.

Data calculated from FIG. 6G revealed that RalA-Aβ complexes were comprised of 16±5% of the total RalA and 9±2% of the total Aβ proteins. These observations indicate that the interaction between the PP2A Aβ complex and RalA involves a small fraction of the total PP2A Aβ complexes and RalA and suggests that these interactions are likely short-lived as would be expected for interactions between phosphatases and their substrates.

We then determined whether cancer-associated Aβ mutants form complexes with endogenous RalA by immunoprecipitating PP2A Aβ immune complexes from HEK TER cells expressing WT Aβ or cancer-associated Aβ mutants (G8R, V454A, and V448A) using anti-FLAG (M2) antibody. Immunoblot analysis was then performed using antibodies specific to RalA (BD Biosciences, San Jose, Calif.) and FLAG (M2).

As shown in FIG. 6H, wtPP2A Aβ but not Aβ point mutants bound endogenous RalA.

We then determined whether the cancer-associated Aβ mutants form complexes with various PP2A subunits. The degree of binding was quantified using densitometry imaging software.

TABLE 2

Classification of Binding Defect of PP2A Aβ Mutants

| Defect Level | Aβ mutant | B55α | B56α | B56γ | B56δ | B56ε | Cα |
|---|---|---|---|---|---|---|---|
| No Defect | wtPP2A Aβ | +++ | +++ | +++ | +++ | +++ | +++ |
| Weak | P65S | +++ | + | + | ++ | +++ | ++ |
|  | G8R | +++ | +++ | + | + | +++ | ++ |
| Moderate | K343E | ++ | + | − | ++ | ++ | + |
|  | D504G | ++ | +++ | − | +++ | +++ | + |
|  | V545A | +++ | + | − | − | + | + |
| Severe | L101P | + | − | − | − | +++ | − |
|  | V448A | + | − | − | − | + | − |
|  | L101P/V448A | − | − | − | − | + | − |
|  | ΔE344-E388 | − | − | − | − | − | − |

Binding levels are expressed as +++ (>90%); ++ (50-90%); + (<50%); and − (not detectable)

As shown in Table 2, all of the Aβ mutants showed an impaired ability to form complexes with the PP2A subunits. In contrast, wtPP2A complex formation was strong.

These observations makes it unlikely that interaction between WT Aβ and RalA is non-specific and suggests that loss of Aβ function also impairs RalA complex formation.

Example 7

RalA is Necessary for Transformation induced by PP2A Aβ Suppression

HA-tagged wt-RalA-V23G and A194S-Ral-V23G were the gift of Dr. Chi-Ying F. Huang (Division of Molecular and Genomic Medicine, National Health Research Institutes, Taipei). HA-tagged wild-type RalA and S11A, S183A and S194A mutants were generated by site-directed mutagenesis and then subcloned into the retroviral vectors pPs-neo and pBabe-Puro.

The pLKO.1-Puro, pLKO.1-shRalA-1, or pLKO.1-shRalA-2 (designated shRalA-1 and shRalA-2) vectors were provided by the RNAi Consortium (Broad Institute) (Moffat et al., *Cell*, 124:1283-1298, 2006).

To assess whether RalA expression was required for cell transformation induced by loss of Aβ expression, we suppressed RalA expression using shRalA-1 and shRalA2.

Briefly, HEK TER cells expressing a control vector (V), ST, LowAα (50% Aα suppression), or shAβ and 2 different shRalAs or shGFP were analyzed for RalA expression (top panel) and cell proliferation (see Example 1). Immunoblotting with RalA-specific antibodies to assess RalA expression (top). The proliferation data is presented as mean±SD for 3 independent experiments.

Figure 7A:
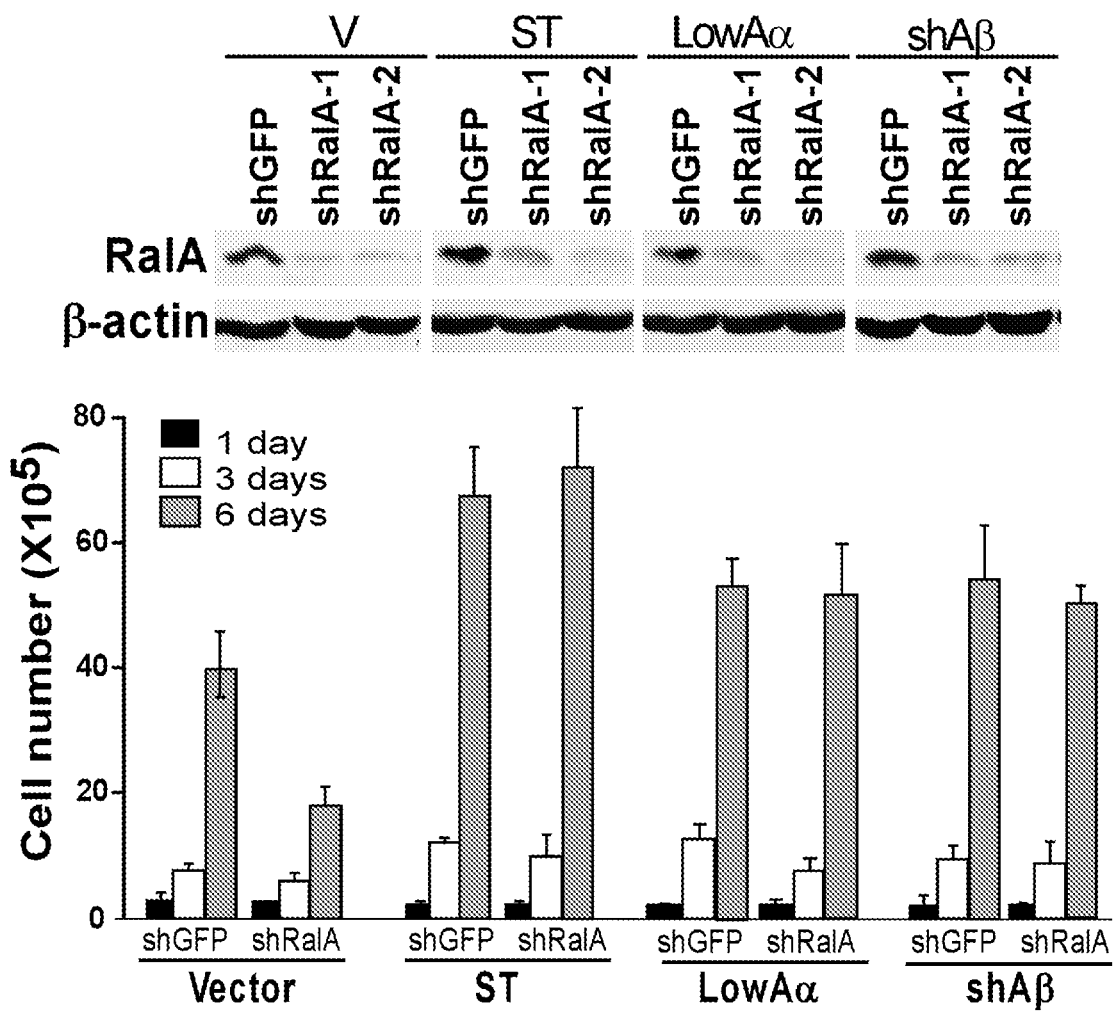

As shown in FIG. 7A, immunoblotting with a RalA-specific antibody, described above, revealed that both shRalA-1 and shRalA-2 efficiently suppressed RalA expression (top panel). This RalA suppression inhibited the proliferation of HEK TER cells expressing the control vector (V). In contrast, RalA suppression failed to affect the proliferation rate of the HEK TER-shAβ, HEK TER-LowAα, and HEK TER-ST cell lines. These findings are consistent with prior observations that showed that RalA is not limiting for serum-dependent proliferation of tumorigenic cells under standard culture conditions (Chien Y., and White M. A., *EMBO Rep.*, 4:800-806, 2003).

To examine the contribution of endogenous RalA to oncogenic transformation, we then tested the consequences of suppressing RalA expression on AI growth, using methods described in Example 1.

As shown in FIG. 7B, depletion of RalA inhibited the ability of HEK TER cells expressing shAβ to form AI colonies by 94±5%. In contrast, RalA suppression in HEK TER cells expressing ST or in which Aα expression was decreased by 50% (LowAα) only partially inhibited the ability of these cells to form AI colonies (37±6% and 61±6%, respectively). These data are consistent with prior observations that showed that oncogenic alleles of H-RAS also activate RalGEFs (Lim et al., *Cancer Cell*, 7:533-545, 2005).

Collectively, the findings in this Example indicate that RalA expression is necessary for the transformed phenotype induced by suppression of Aβ.

Example 8

PP2A Aβ Negatively Regulates RalA Activity

To determine whether the interaction of Aβ with RalA perturbs RalA function, we examined RalA activity in HEK TER cells in which Aβ expression was suppressed. RalA activity was analyzed by determining the amount of GTP-bound, and therefore active, RalA bound to recombinant Ral-BP1 protein, as follows.

The RalA activation assay was performed using RalA activation kit (Upstate Biotechnology, Lake Placid, N.Y.). Cell lysates (2 mg) were pre-cleared with glutathione agarose (Amersham Biosciences, Piscataway, N.J.) and then incubated with 20 μl of RalBP1 agarose for 1 h. The beads were washed, and the samples were subjected to 12% SDS-PAGE, transferred to nitrocellulose membranes and immunoblotted with an anti-RalA antibody (BD Biosciences, San Jose, Calif.). Amount of GTP-bound RalA was detected in HEK TER expressing shGFP, SV40 ST, LowAα, shAβ, or overexpressing wtPP2A Aα or wtPP2A Aβ.

As shown in FIG. 7C, a 4.5-fold increase in GTP-bound RalA levels was observed in cells lacking Aβ compared to control cells expressing shGFP. Expression of ST or partial suppression of Aα had no effect on the steady state amount of GTP-bound RalA. These observations are consistent with our prior observations that suggested that Aβ induces transformation by a mechanism distinct from that caused by partial inhibition of Aα or ST overexpression, see Example 7.

RalA activity was also assessed in HEK TER-shAβ cells expressing a control vector or shAβ-resistant forms of PP2A Aβ (see Example 1), or G8R Aβ mutant, and lung carcinoma H2009 and H838 cells expressing control vector (Vector) or wtPP2A Aβ.

As shown in FIG. 7D, in contrast to the above, introduction of exogenous PP2A Aβ inhibited RalA activity in both HEK TER and HEK TER-shAβ cells as measured by decreased levels of GTP-bound RalA. To examine whether cancer-derived Aβ mutants affected RalA activity, we overexpressed the shRNA-resistant G8R Aβ mutant in HEK TER cells lacking Aβ expression and observed that the G8R Aβ mutant, which does not form complexes with RalA (see FIG. 6H), failed to affect RalA activity. Consistent with these findings, the H838 lung cancer cell line that harbors a single mutant Aβ allele exhibited approximately 4-fold higher levels of RalA activity compared to the H2009 carcinoma cell line that harbors WT Aβ. Overexpression of wtPP2A Aβ in both H838 and H2009 cell lines decreased the amount of GTP-bound RalA identified using this Ral-BP1 binding assay. Moreover, introduction of WT PP2A Aβ into H838 cells decreased the amount of activated RalA to the level found in H2009 cells, as shown in FIG. 7D. Taken together, importantly, these experiments indicate that the interaction of Aβ with RalA inhibits RalA activity.

Example 9

PP2A Aβ Dephosphorylates RalA

We next determined whether PP2A Aβ complexes dephosphorylate RalA. Briefly, the phosphorylation status of RalA was assessed in cells expressing or lacking Aβ, as follows. Total serine phosphorylated proteins were isolated from HEK TER cells expressing shGFP or shAβ by immunoprecipitation with a phospho-serine antibody and immunoblot analysis was performed using anti-RalA antibody.

Figure 8A:
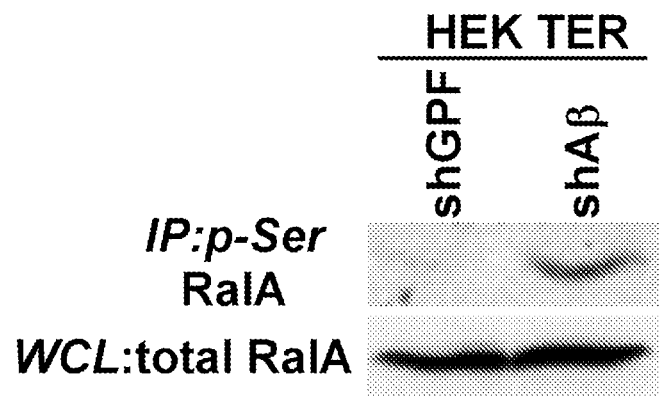
FIGS. 8A-8B are immunoblots showing immunoprecipitations performed in HEK TER and 293T cells. (A) Immunoblot showing phosphorylated RalA and total RalA levels in HEK TER cells expressing shGFP or shAβ. Immunoprecipitations were performed using a phosphoserine antibody. Immunoblotting was performed using anti-Ral-antibody. WCL=whole cell lysate. (B) Immunoblot showing interaction between Aβ and RalA mutants. FLAG-tagged Aβ and HA-tagged RalA (wt, S11A, S183A, S194A) were expressed in 293T cells and co-immunoprecipitations were performed using anti-FLAG agarose.

As shown in FIG. 8A, using a commercially available phospho-serine specific antibody (Qiagen PhosphoProtein Purification Kit to pull down phospho-ser/thr proteins and the Qiagen phospho-serine Q5 antibody), we observed elevated serine-phosphorylated RalA levels in those cell lines in which Aβ was suppressed. This observation suggested that RalA was a direct substrate for PP2A Aβ complexes.

RalA can be phosphorylated by Aurora A kinase at Ser194 (Wu et al., *J. Biol. Chem.*, 280:9013-9022, 2005). In an attempt to identify other potential RalA phosphorylation site(s), we isolated RalA from HEK TER-shAβ cells and performed mass spectrometric analysis. This search found evidence of RalA phosphorylation at Ser11 and Ser183 (data not shown) but no other serine or threonine residues.

To determine if these newly identified serine residues were the target of Aβ-containing PP2A complexes, we replaced each of these three serine residues with alanine using site-directed mutagenesis to generate HA-tagged S11A, S183A and S194A RalA mutants. Mutant clones were then subcloned into the retroviral vectors pPs-neo and pBabe-Puro, and these RalA alanine substitution mutants were co-expressed with FLAG-tagged Aβ (wtPP2A Aβ) in 293T cells. We then determined whether these RalA mutants retained the ability to bind Aβ, as follows. Briefly, Aβ-specific complexes were isolated using anti-FLAG agarose followed by immunoblotting using FLAG or RalA specific antibodies.

Figure 8B:
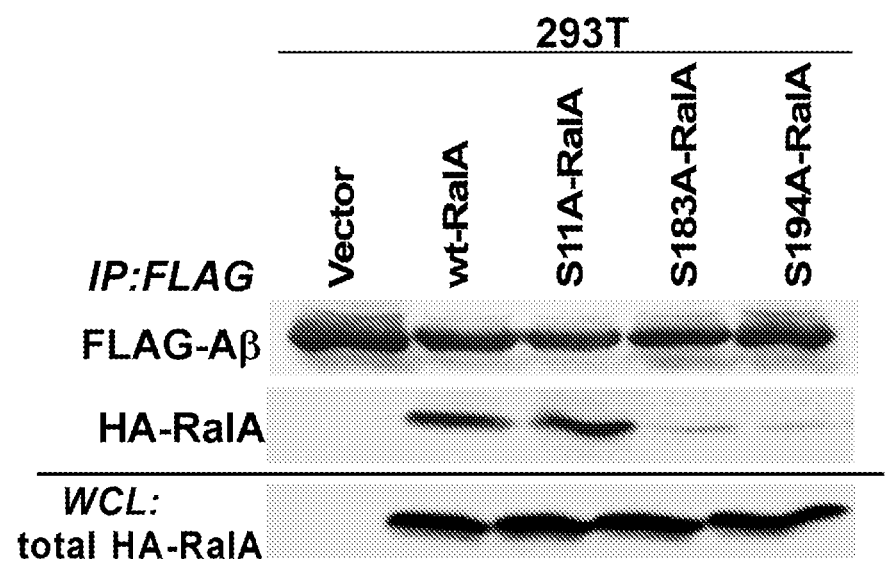

As shown in FIG. 8B, we found that wtPP2A Aβ bound to both WT RalA and the S11A RalA mutant. In contrast, the S183A and S194A RalA mutants showed diminished ability to form complexes with Aβ. These observations suggested that PP2A Aβ binds to and dephosphorylates RalA at Ser183 and Ser194.

Example 10

Generation of Phosphospecific RalA Antibodies

To confirm the observations made in Example 9, we created phosphospecific antibodies that recognize RalA phosphorylated at Ser183/Ser194 by immunizing mice with two KLH-conjugated phospho-peptides (phospho-Ser183 and phospho-Ser194), as follows.

To generate phosphospecific antibodies, 6 mice were immunized with two KLH-conjugated phospho-peptides phospho-Ser183, SEQ ID NO: 11, and phospho-Ser194, SEQ ID NO:12.

```
Ac-CRARKMED(pS)KEKNG-amide    (SEQ ID NO: 11)

Ac-KRK(pS)LAKRIRERC-amide     (SEQ ID NO: 12)
``` wherein (pS) indicates a phosphoserine.

After 3 rounds of immunizations, murine sera from 5 mice were tested by immunoblotting BSA-conjugated phosphorylated RalA peptides. Hybridomas were then generated from one of these mice and 1,000 supernatants were tested by ELISA. This screen identified 13 positive supernatants, which were subsequently analyzed by immunoblotting RalA phospho-peptides.

As shown in FIGS. 9A-9D, the sera from one of immunized mouse (designated IMS) and several hybridoma supernatants derived from this immunized mouse, particularly the hybridoma supernatant designated XL13, contained antibodies specific for RalA phosphorylated at Ser183 and Ser194.

More specifically, control vector (vector); WT RalA and S11A, S183A, S194A and S183/194A RalA mutants were overexpressed in HEK TERV and HEK TER-shAβ. Immunoprecipitation was then performed as described in Example 1, albeit, using an anti-HA antibody (clone 12C5; Boehringer Mannheim). Isolated HA-immune complexes were then resolved using SDS-PAGE, as described in Example 1, and immunoblotting was performed using sera form mice immunized with phospho-Ser183 RalA and phospho-Ser194 RalA peptides (designated IMS), XL13 hybridoma supernatant, or FLAG (M2) antibodies.

Figure 9A:
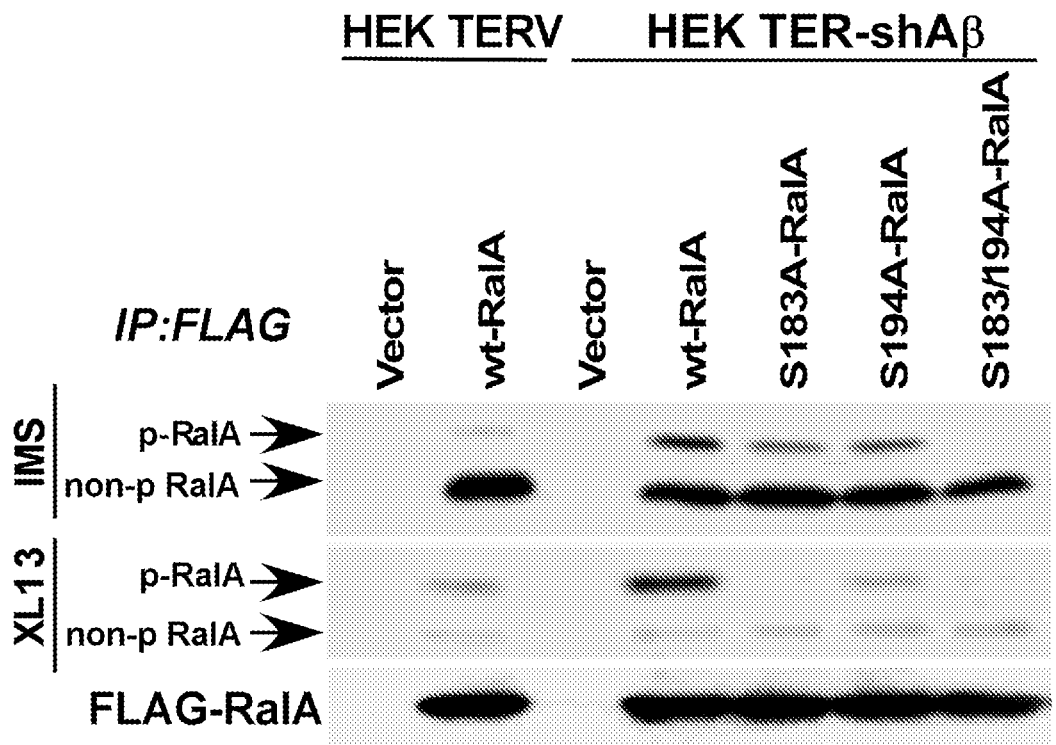
FIGS. 9A-9I are immunoblots a bar graph, and a line graph showing RalA phosphorylation levels, RalA activation, AI growth, tumor formation, RalA mutant sequence, and tumor growth kinetics. (A) Immunoblot showing RalA phosphorylation at amino acids serine 183 and serine 194 as assessed using sera of immunized mice (IMS) and XL13 antibodies. Control vector (vector), wtRalA, S11A, S183A, S194A, and S183/194A RalA mutants were over expressed in HEK TERV amd HEK TER-shAβ cells. Precipitations were performed using anti-HA agarose. (B) Immunoblot showing specificity of IMS antibody. RalA phosphorylation was assessed in HEK TER-shAβ cells expressing empty vector (V) or HA-tagged RalA. Immunoprecipitation was performed using anti-HA agarose (HA7). One half of the resulting HA-precipitated RalA was treated with calf intestinal alkaline phosphatases (CIP). Immunoblotting was performed with pre-immunized murine sera (pre-IMS) or IMS. (C) Immunoblots as described for (B) probed with XL13. (D) Immunoblots as described for (B) probed with RalA antibodies (BD Biosciences). (E) Immunoblot showing phospho-RalA expression levels in the membrane fractions of lung carcinoma cell lines H1437, H2009, H1450, and H838. Immunoblotting was performed using XL13 or anti-FLAG antibody for total RalA. (F) Silent mutations generated in RalA (nucleotides 225 to 246) sequence targeted by shRalA. (G) Immunoblot showing RalA and RalA mutant (described in (F)) activity levels. GTP-bound RalA levels were determined in HEK TER-shAβ-shRalA cells expressing shRalA resistant RalA (see (F)). (H) Bar graph showing AI growth and tumor formation of HEK TER-shAβ-shRalA cells expressing shRalA-resistant mutants. The number of AI colonies formed is presented as the mean±SD for 3 independent experiments. Tumors are reported as the number of tumors formed per injection site. (I) Line graph showing the effect of RalA phosphorylation on tumor growth. HEK TER-shAβ cells and HEK TER-shAβ-shRalA cells expressing shRalA-resistant wild type RalA, S11A, S183A, S194A mutants (n=6) were injected subcutaneously and xenograft growth was measured biweekly.

As shown in FIG. 9A, IMS bound both phosphorylated and non-phosphorylated forms of RalA, whereas XL13 bound only phosphorylated RalA.

The newly generated phospho-specific IMS and XL13 antibodies were then used to determine whether RalA Ser183 and Ser194 were indeed targets of PP2A Aβ, as follows.

Figure 9B:
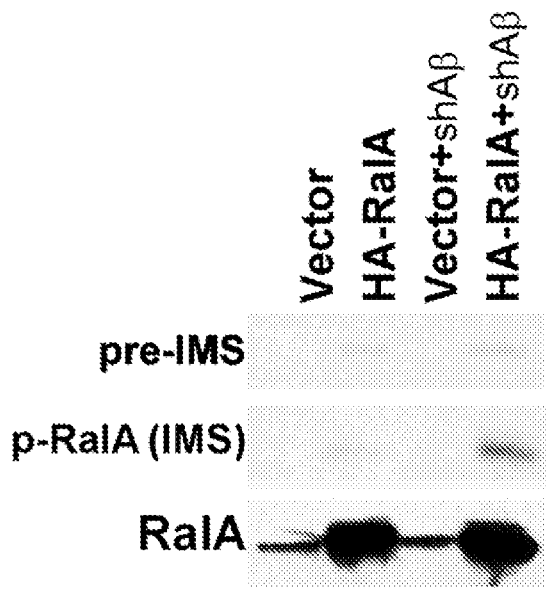

Interestingly, in cells lacking the expression of Aβ, a condition in which we previously observed increased RalA activity, IMS and XL13 antibodies recognized higher levels of phosphorylated RalA, compared to those cells expressing Aβ (see FIG. 9A (compare wt-RalA levels in HEK TER-shAβ and HEK TERV, respectively) and FIG. 9B (compare HA-RalA lane with HA-RalA+shAβ lane). Note, as shown in FIG. 9B, pre-immunized murine sera (pre-IMS) did not cross react with RalA.

Figure 9C:
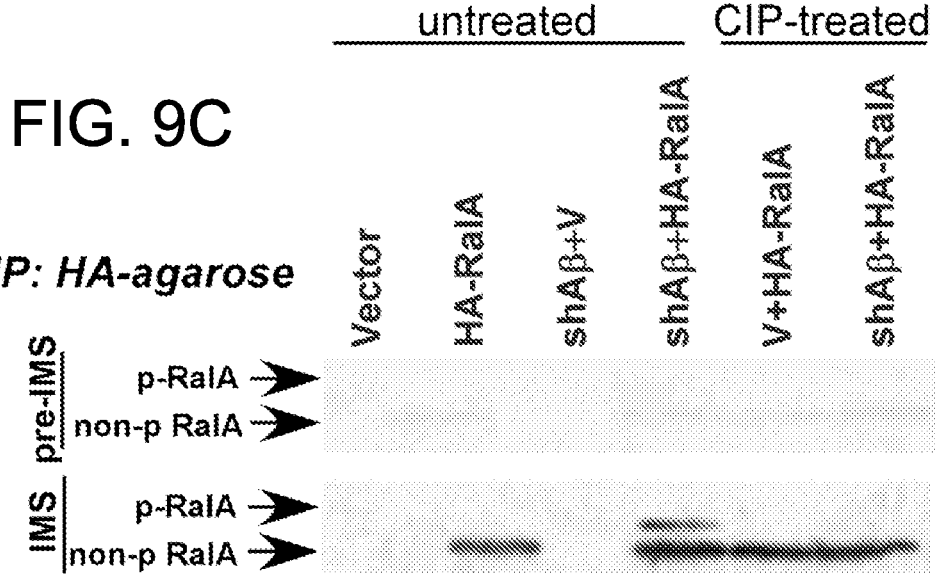
Figure 9D:
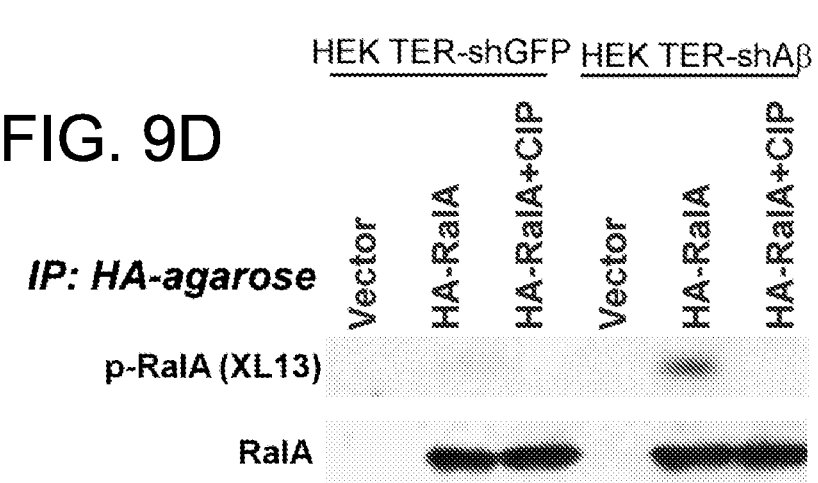

To verify the specificity of these antibodies, we treated RalA immune complexes with calf intestinal phosphatase (CIP), which eliminated the RalA species detected by these phosphospecific antibodies without affecting total RalA levels, as shown in FIGS. 9C-9D.

Briefly, RalA phosphorylation levels were analyzed in HEK TER-shGFP and HEK TER-shAβ cells expressing empty vector (V) or HA-tagged RalA. HA-tagged RalA was then pulled down using HA-agarose (HA7). Immunoprecipitated samples were then divided into two, one of which was subsequently treated with calf intestinal alkaline phosphatase (CIP). The remaining sample was left untreated. Immunoblotting was performed using pre-IMS and IMS (see FIG. 9C), or XL13 antibody and anti-RalA antibody (BD Biosciences) (see FIG. 9D).

As shown in FIG. 9C, consistent with FIG. 9B, pre-IMS did not cross-react with immunoprecipitated RalA (top panel). IMS, however, recognized total RalA (non-phosphorylated) and phosphorylated RalA only in those sample containing RalA with suppressed Aβ (bottom panel). As shown in FIG. 9D, XL13 antibody bound to/recognized only phosphorylated RalA. RalA was not detected following CIP treatment. These observations strongly support the specificity of the newly generated IMS and XL13 antibodies.

As shown in FIG. 9A, when we overexpressed WT RalA and S183A, S194A and S183/194A RalA mutants in HEK TER cells lacking Aβ expression (HEK TER-shAβ), we found that the S183A and S194A RalA mutants showed decreased levels of phospho-RalA compared to WT RalA. In both cases, however, both phosphospecific IMS and XL13 antibodies still detected phosphorylated RalA. Importantly, detection of phosphorylated RalA by both phosphospecific IMS and XL13 antibodies was only abolished in cells expressing the S183/194A RalA mutant (see FIG. 9A). This result strongly suggests that both phosphospecific IMS and XL13 antibodies bind to both Ser183 and Ser194, and not one or the other. In other words, both Ser183 and Ser194 are the targets bound to or recognized by both of the newly generated phosphospecific IMS and XL13 antibodies. In addition, these results confirm that Ser183 and Ser194 in RalA are the targets of PP2A Aβ-containing complexes.

Next, we analyzed phosphor-RalA levels in the lung cancer cell lines described in Example 4.

Figure 9E:
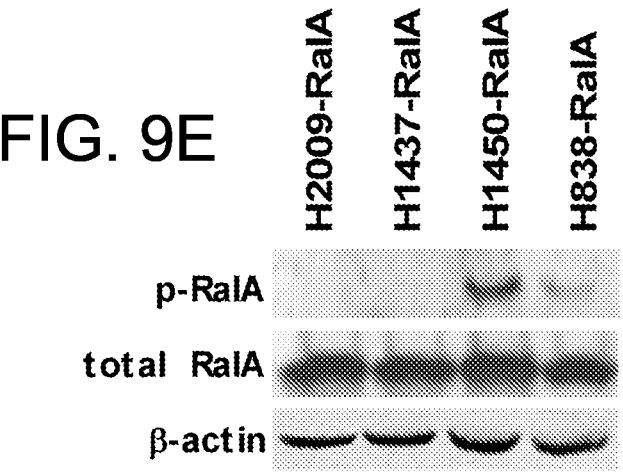

Briefly, phospho-RalA expression levels were analyzed in the membrane fraction of lung carcinoma cell lines (H1437, H2009, H1450 and H838), using the method described in Example 6. Immunoblotting was performed using XL13 hybridoma supernatant. Total RalA was immunoblotted using RalA specific antibody. β-actin was probed as a loading control. As shown in FIG. 9E, phosphorylated forms of RalA were undetectable in the H1437 and H2009 cell lines that harbor WT Aβ. In contrast, RalA was phosphorylated in H838 and H1450 cell lines that lack functional Aβ alleles.

Together, these studies further strongly implicate RalA Ser183 and Ser194 as substrates of PP2A complexes containing Aβ.

Figure 9F:
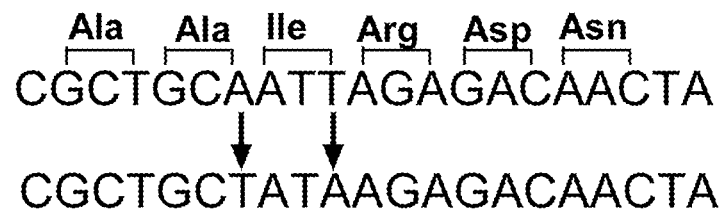

To determine whether the phosphorylation state of RalA contributes to transformation induced by loss of Aβ function, we created S183A and S194A RalA mutants resistant to the RalA-specific shRNA (shown in FIG. 9F; sequence corresponds to nucleotides 225 to 246 of RalA; see SEQ ID NO:9) by introducing silent substitutions into the RalA coding sequence using site-directed mutagenesis. The newly generated shRNA-resistant RalA mutants were then overexpressed in HEK TER cells in which both RalA and Aβ were suppressed using the shRNAs described above (HEK TER-shAβ-shRalA) and the amount of GTP-bound RalA was determined in HEK TER-shAβ-shRalA cells expressing shRNA-resistant forms of RalA using GST-RalBP1, which exclusively binds to active (phosphorylated) RalA (Upstate Biotech.)

Figure 9G:
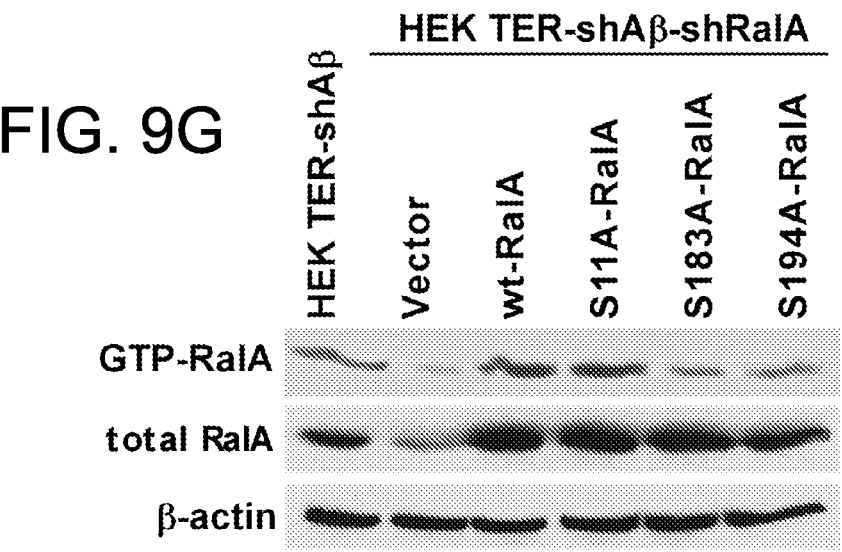
Figure 9H:
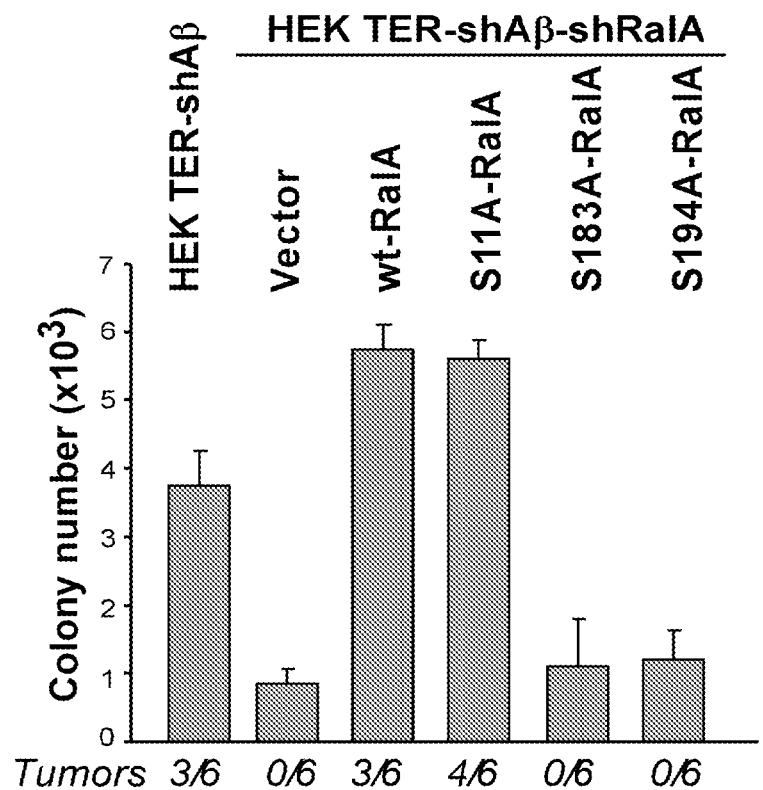
Figure 9I:
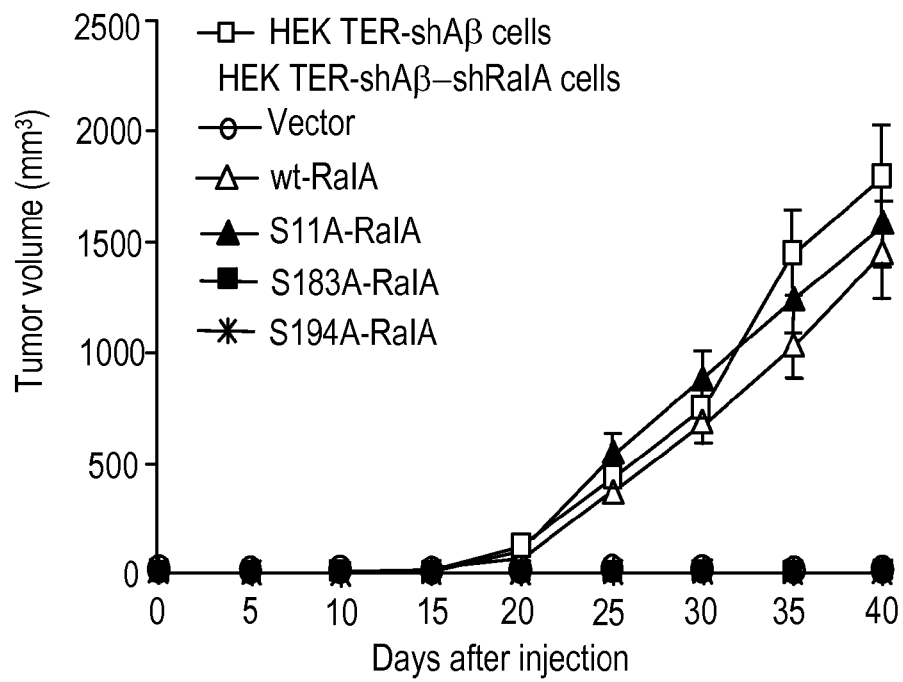

As shown in FIG. 9G, the overexpression of WT RalA or the S11A RalA mutant restored RalA activity while expression of the S183A or S194A RalA mutants was unable to complement the suppression of endogenous RalA. These observations strongly suggest that PP2A Aβ-mediated dephosphorylation of RalA at Ser183 and Ser194 down-regulates RalA activity. Consistent with these observations, as shown in FIGS. 9H and 9I, suppression of RalA in HEK TER-shAβ cells inhibited AI growth and tumor formation, and expression of a shRalA-resistant form of WT RalA or the S11A RalA mutant restored the tumorigenic phenotype caused by Aβ suppression. In contrast, overexpression of shRalA-resistant S183A or S194A RalA mutants failed to reverse the transforming phenotype induced by loss of Aβ expression.

Figure 10:
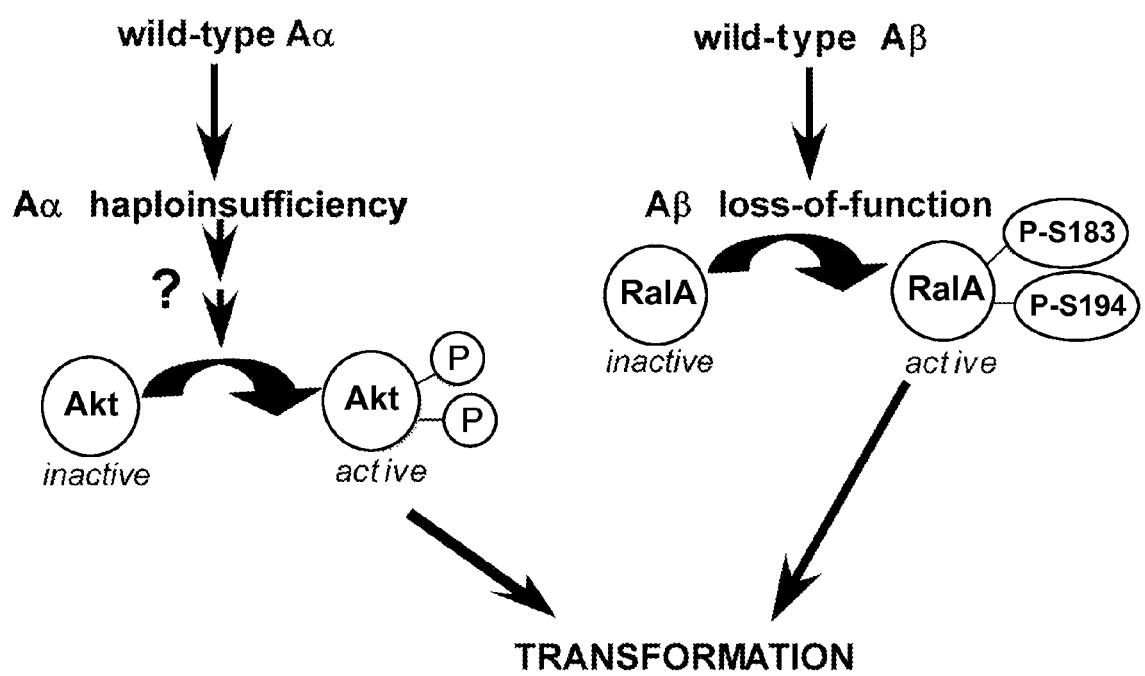
FIG. 10 is a schematic representation summarizing the distinct mechanisms used by PP2A Aα and Aβ subunit mutants in transformation.

An illustrated summary of the distinct mechanisms used by PP2A Aα and Aβ subunits in cell transformation is presented in FIG. 10. Cancer-associated PP2A Aα mutations result in Aα haploinsufficiency, which induces human cell transformation by selectively eliminating PP2A B56λ containing complexes. One consequence is constitutive Akt phosphorylation. In contrast, PP2A Aβ loss-of-function permits the accumulation of activated RalA.

The above observations establish PP2A Aβ as a serine threonine phosphatase tumor suppressor gene that contributes to cell transformation by regulating the phosphorylation status and activity of RalA necessary for the initiation and/or maintenance of tumors.

In toto, these observations implicate the control of phosphorylation of RalA at Ser183 and Ser194 by PP2A Aβ as a critical regulatory step in RalA function and demonstrate the usefulness of the phosphospecific IMS and XL13 antibodies in monitoring the phosphorylation state of RalA.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method for detecting the presence of a polypeptide comprising SEQ ID NO: 9 in a subject, wherein the polypeptide is phosphorylated at one or both of Ser183 and Ser194, the method comprising:
 (a) providing a biological sample;
 (b) contacting the biological sample with an antibody or antigen binding portion thereof, wherein the antibody: i) binds to a polypeptide consisting of SEQ ID NO: 9 (RalA) that is phosphorylated at one or both of Ser183 and Ser194; and ii) does not bind to a polypeptide consisting of SEQ ID NO:9 that is not phosphorylated at Ser183 and is not phosphorylated at Ser194; and
 (c) detecting the presence or absence of a polypeptide comprising SEQ ID NO: 9, that is phosphorylated at one or both of Ser183 and Ser194 bound to the antibody or antigen binding portion thereof.

2. A method for detecting the presence of a polypeptide comprising SEQ ID NO: 9 in a subject at two time points, wherein the polypeptide is phosphorylated at one or both of Ser183 and Ser194 the method comprising:
 (a) providing a first biological sample taken from a subject at a first time point;
 (b) providing a second biological sample taken from the subject at a second time point after the first time point; and
 (c) contacting each of the first and the second biological samples with an antibody or antigen binding portion thereof, wherein the antibody: i) binds to a polypeptide consisting of SEQ ID NO: 9 (RalA) that is phosphorylated at one or both of Ser183 and Ser194; and ii) does not bind to a polypeptide consisting of SEQ ID NO:9 that is not phosphorylated at Ser183 and is not phosphorylated at Ser194;
 (d) detecting the presence or absence of RalA or a polypeptide comprising SEQ ID NO: 9, that is phosphorylated at one or both of Ser183 and Ser194 bound to the antibody or antigen binding portion thereof in each of the first and second biological samples.

3. The method of claim 1 or 2 wherein the isolated antibody molecule or antigen binding portion thereof binds to a polypeptide comprising SEQ ID NO: 9 that is phosphorylated at both Ser183 and Ser194.

4. The method of claim 1 or 2 wherein the antibody molecule or antigen binding portion thereof is a recombinant antibody molecule or antigen binding portion thereof.

5. The method of claim 1 or 2 wherein the antibody molecule or antigen binding portion thereof has a dissociation constant ($K_d$) for the polypeptide consisting of SEQ ID NO: 9 that is phosphorylated at one or both of Ser183 and Ser194 in the range of $10^{-6}$ M to $10^{-12}$ M.

6. The method of claim 1 or 2 wherein the antibody molecule or antigen binding portion thereof is detectably labeled.

* * * * *

UNITED STATES PATENT AND TRADEMARK OFFICE
CERTIFICATE OF CORRECTION

PATENT NO. : 8,637,260 B2  
APPLICATION NO. : 13/108951  
DATED : January 28, 2014  
INVENTOR(S) : William C. Hahn, Laura Corral and Anna A. Sablina Page 1 of 1

It is certified that error appears in the above-identified patent and that said Letters Patent is hereby corrected as shown below:

On the Title Page, item (54) and in the Specification, Column 1, Line 1 (Title), delete "RAIA" and insert -- RALA --, therefor.

Signed and Sealed this  
Twenty-fourth Day of June, 2014

Michelle K. Lee  
*Deputy Director of the United States Patent and Trademark Office*

SEQUENCE LISTING

<160> NUMBER OF SEQ ID NOS: 15

<210> SEQ ID NO 1
<211> LENGTH: 2205
<212> TYPE: DNA
<213> ORGANISM: Homo sapiens

<400> SEQUENCE: 1

```
gaattccggt tctcactctt gacgttgtcc agctccagca ccttggcaac tcccccagct      60
tggacggccg gcccgccgct ccatggggga gtcatctgag cacagctgct ggccgcagtc     120
tgacaggaaa gggacggagc caagatggcg gcggccgacg gcgacgactc gctgtacccc     180
atcgcggtgc tcatagacga actccgcaat gaggacgttc agcttcgcct caacagcatc     240
aagaagctgt ccaccatcgc cttggccctt ggggttgaaa ggacccgaag tgagcttctg     300
cctttcctta cagataccat ctatgatgaa gatgaggtcc tcctggccct ggcagaacag     360
ctgggaacct tcactaccct ggtgggaggc ccagagtacg tgcactgcct gctgccaccg     420
ctggagtcgc tggccacagt ggaggagaca gtggtgcggg acaaggcagt ggagtccta     480 cgggccatct cacacgagca ctcgccctct gacctggagg cgcactttgt gccgctagtg     540
aagcggctgg cgggcggcga ctggttcacc tcccgcacct cggcctgcgg cctcttctcc     600
gtctgctacc cccgagtgtc cagtgctgtg aaggcggaac ttcgacagta cttccggaac     660
ctgtgctcag atgacacccc catggtgcgg cgggccgcag cctccaagct gggggagttt     720
gccaaggtgc tggagctgga caacgtcaag agtgagatca tccccatgtt ctccaacctg     780
gcctctgacg agcaggactc ggtgcggctg ctggcggtgg aggcgtgcgt gaacatcgcc     840
cagcttctgc cccaggagga tctggaggcc ctggtgatgc ccactctgcg ccaggccgct     900
gaagacaagt cctgggccgt ccgctacatg gtggctgaca agttcacaga gctccagaaa     960
```

```
gcagtggggc ctgagatcac caagacagac ctggtccctg ccttccagaa cctgatgaaa    1020
gactgtgagg ccgaggtgag ggccgcagcc tcccacaagg tcaaagagtt ctgtgaaaac    1080
ctctcagctg actgtcggga gaatgtgatc atgtcccaga tcttgccctg catcaaggag    1140
ctggtgtccg atgccaacca acatgtcaag tctgccctgg cctcagtcat catgggtctc    1200
tctcccatct tgggcaaaga caacaccatc gagcacctct gcccctcttt cctggctcag    1260
ctgaaggatg agtgccctga ggtacggctg aacatcatct ctaacctgga ctgtgtgaac    1320
gaggtgattg gcatccggca gctgtcccag tccctgctcc ctgccattgt ggagctggct    1380
gaggacgcca gtggcgggt gcggctggcc atcattgagt acatgcccct cctggctgga    1440
cagctgggag tggagttctt tgatgagaaa cttaactcct tgtgcatggc ctggcttgtg    1500
gatcatgtat atgccatccg cgaggcagcc accagcaacc tgaagaagct agtggaaaag    1560
tttgggaagg agtgggccca tgccacaatc atccccaagg tcttggccat gtccggagac    1620
cccaactacc tgcaccgcat gactacgctc ttctgcatca atgtgctgtc tgaggtctgt    1680
gggcaggaca tcaccaccaa gcacatgcta cccacggttc tgcgcatggc tggggacccg    1740
gttgccaatg tccgcttcaa tgtggccaag tctctgcaga gatagggcc catcctggac    1800 aacagcacct gcagagtga agtcaagccc atcctagaga agctgaccca ggaccaggat    1860
gtggacgtca atactttgc ccaggaggct ctgactgttc tgtctctcgc tgatgctgg    1920 aagaggagca aacactggcc tctggtgtcc accctccaac cccacaagt ccctctttgg    1980 ggagacactg gggggccttt ggctgtcact ccctgtgcat ggtctgaccc caggcccctt    2040 ccccccagcac ggttcctcct ctccccagcc tgggaagatg tctcactgtc cacctcccaa    2100
cggctagggg agcacggggt tggacaggac agtgaccttg ggaggaaggg gctactccgc    2160
catccttaaa agccatggag ccggaggtgg caattcaccg aattc                    2205
```

<210> SEQ ID NO 2
<211> LENGTH: 1922
<212> TYPE: DNA
<213> ORGANISM: Homo sapiens

<400> SEQUENCE: 2

```
gggtgaccag cagcaggagg agaaagaaca tggcgggcgc atcagagctc gggaccggcc      60
caggagcagc gggtggagat ggagatgatt cgctataccc gatcgcggtt ttaatcgacg     120
agctccgcaa tgaagacgtg cagctccgac tcaacagtat taagaagtta tcaacaattg     180
ccctagcact tggagtagaa aggacccgaa gtgaattgtt gccatttctt acagatacaa     240
tttatgatga agatgaggta ctattagctc ttgctgagca gctgggaaat ttcactggcc     300
tagtgggagg tcctgacttt gcccactgtc tgctgcctcc tttggaaaat ctggcaactg     360
tggaagagac tgttgttcgt gacaaggctg tggagtccct gagacagatc tcccaggagc     420
atactcctgt tgctctggaa gcttatttg tacctctggt gaaacgctta gcaagtgggg     480
attggttcac ctctcgcaca tctgcatgtg gtttgttcag cgtttgctat cccagggcat     540
caaatgctgt taaagcagaa atcagacagc aattccgttc cttgtgctca gatgacacac     600
caatggtacg acgtgctgct gcttccaaat tgggtgaatt tgcaaaagtt ttggaattag     660
acagtgtgaa aagtgaaatt gttccactgt tcactagtct agcttcagat gaacaggatt     720
cagtgcgcct ccttgctgtg aagcttgtg tcagtattgc ccagttattg tctcaggatg     780 acccttgagac tttggtgatg cctacacttc gacaagcagc agaagataaa tcttggcgcg     840
ttcgctatat ggtggctgac agattttcag agctccagaa agccatgggt cctaaaatca     900
```

```
ccctaaatga cctcatcccc gcctttcaga acctacttaa agactgtgaa gctgaagtcc    960
gggcagctgc tgcccacaaa gtaaaagaac ttggtgagaa cttgcccatt gaagatagag   1020
agaccataat tatgaatcaa attctgcctt atataaagga attagtatcc gataccaatc   1080
aacatgtcaa atcggctcta gcttctgtaa ttatgggatt gtctactatt ttgggcaaag   1140
aaaataccat tgaacatctt ctacctctttt tcttagctca gttaaaggat gagtgtcctg   1200
acgttcgttt gaatatcatc tccaatttgg attgtgtaaa tgaagtgatt ggaatccgtc   1260
agctctctca gtctctcctt cctgccatag tggagctggc agaagatgcc aaatggaggg   1320
tccgcctggc catcattgag tatatgccgc tgctggcagg ccagctgggt gtggaattct   1380
ttgatgaaaa gctgaattct ttatgtatgg cttggctcgt ggaccatgta tacgccatcc   1440
gagaagctgc caccaacaac ctcatgaaac tagttcagaa gtttggtaca gagtgggccc   1500
aaaatactat tgttcccaaa gtgttagtaa tggcaaatga tcctaattac ttgcatagaa   1560
tgaccacttt attctgcatt aatgcactgt ctgaggcctg tggtcaggaa ataactacta   1620
agcaaatgct gcccatcgta ttaaaaatgg caggagacca agtagcaaat gttcgcttca   1680
atgtggccaa atctctacaa aagattggac caattctaga taccaatgct ttacagggag   1740
aagtgaagcc agtactacag aagttaggtc aagatgaaga catggatgtc aaatactttg   1800
cacaggaagc tataagtgtt cttgcattgg cataatgagg agcaggaggg aaaaggcctt   1860
tactagattc ttgtcacaaa tttctagtca atgtgttctt aactgggtgg agaaagaatg   1920
ga                                                                  1922

<210> SEQ ID NO 3
<211> LENGTH: 63
<212> TYPE: DNA
<213> ORGANISM: Artificial Sequence
<220> FEATURE:
<223> OTHER INFORMATION: Synthetically generated oligonucleotide

<400> SEQUENCE: 3
ggcggcggat ccatggacta caaagacgat gacgacaagg cgggcgcatc agagctcggg    60
acc                                                                  63

<210> SEQ ID NO 4
<211> LENGTH: 42
<212> TYPE: DNA
<213> ORGANISM: Artificial Sequence
<220> FEATURE:
<223> OTHER INFORMATION: Synthetically generated oligonucleotide

<400> SEQUENCE: 4
ggcggcggcc tcgagttatg ccaatgcaag aacacttata gc                       42

<210> SEQ ID NO 5
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 5
gacgagctcc gcaatgaag                                                 19

<210> SEQ ID NO 6
<211> LENGTH: 18
<212> TYPE: DNA
<213> ORGANISM: Artificial Sequence
<220> FEATURE:
```

-continued

<223> OTHER INFORMATION: Synthetically generated oligonucleotide

<400> SEQUENCE: 6
gggactccac agccttgt                                                  18

<210> SEQ ID NO 7
<211> LENGTH: 12
<212> TYPE: PRT
<213> ORGANISM: Artificial Sequence
<220> FEATURE:
<223> OTHER INFORMATION: Synthetically generated polypeptide

<400> SEQUENCE: 7

Glu Leu Lys Arg Gly Leu Arg Arg Asp Gly Pro Thr
1               5                   10

<210> SEQ ID NO 8
<211> LENGTH: 467
<212> TYPE: PRT
<213> ORGANISM: Homo sapiens

<400> SEQUENCE: 8

Met Ser Ser Ala Pro Thr Thr Pro Ser Val Asp Lys Val Asp Gly
1               5                   10                  15

Phe Ser Arg Lys Ser Val Arg Lys Ala Arg Gln Lys Arg Ser Gln Ser
                20                  25                  30

Ser Ser Gln Phe Arg Ser Gln Gly Lys Pro Ile Glu Leu Thr Pro Leu
            35                  40                  45

Pro Leu Leu Lys Asp Val Pro Ser Ser Glu Gln Pro Glu Leu Phe Leu
50                  55                  60

Lys Lys Leu Gln Gln Cys Cys Val Ile Phe Asp Phe Met Asp Thr Leu
65                  70                  75                  80

Ser Asp Leu Lys Met Lys Glu Tyr Lys Arg Ser Thr Leu Asn Glu Leu
                85                  90                  95

Val Asp Tyr Ile Thr Ile Ser Arg Gly Cys Leu Thr Glu Gln Thr Tyr
            100                 105                 110

Pro Glu Val Val Arg Met Val Ser Cys Asn Ile Phe Arg Thr Leu Pro
        115                 120                 125

Pro Ser Asp Ser Asn Glu Phe Asp Pro Glu Glu Asp Glu Pro Thr Leu
130                 135                 140

Glu Ala Ser Trp Pro His Leu Gln Leu Val Tyr Glu Phe Phe Ile Arg
145                 150                 155                 160

Phe Leu Glu Ser Gln Glu Phe Gln Pro Ser Ile Ala Lys Lys Tyr Ile
                165                 170                 175

Asp Gln Lys Phe Val Leu Gln Leu Leu Glu Leu Phe Asp Ser Glu Asp
            180                 185                 190

Pro Arg Glu Arg Asp Tyr Leu Lys Thr Val Leu His Arg Ile Tyr Gly
        195                 200                 205

Lys Phe Leu Gly Leu Arg Ala Phe Ile Arg Lys Gln Ile Asn Asn Ile
210                 215                 220

Phe Leu Arg Phe Val Tyr Glu Thr Glu His Phe Asn Gly Val Ala Glu
225                 230                 235                 240

Leu Leu Glu Ile Leu Gly Ser Ile Ile Asn Gly Phe Ala Leu Pro Leu
                245                 250                 255

Lys Ala Glu His Lys Gln Phe Leu Val Lys Val Leu Ile Pro Leu His
            260                 265                 270

Thr Val Arg Ser Leu Ser Leu Phe His Ala Gln Leu Ala Tyr Cys Ile
        275                 280                 285

```
Val Gln Phe Leu Glu Lys Asp Pro Ser Leu Thr Glu Pro Val Ile Arg
    290                 295                 300

Gly Leu Met Lys Phe Trp Pro Lys Thr Cys Ser Gln Lys Glu Val Met
305                 310                 315                 320

Phe Leu Gly Glu Leu Glu Glu Ile Leu Asp Val Ile Glu Pro Ser Gln
                325                 330                 335

Phe Val Lys Ile Gln Glu Pro Leu Phe Lys Gln Ile Ala Lys Cys Val
                340                 345                 350

Ser Ser Pro His Phe Gln Val Ala Glu Arg Ala Leu Tyr Tyr Trp Asn
                355                 360                 365

Asn Glu Tyr Ile Met Ser Leu Ile Glu Glu Asn Ser Asn Val Ile Leu
    370                 375                 380

Pro Ile Met Phe Ser Ser Leu Tyr Arg Ile Ser Lys Glu His Trp Asn
385                 390                 395                 400

Pro Ala Ile Val Ala Leu Val Tyr Asn Val Leu Lys Ala Phe Met Glu
                405                 410                 415

Met Asn Ser Thr Met Phe Asp Glu Leu Thr Ala Thr Tyr Lys Ser Asp
                420                 425                 430

Arg Gln Arg Glu Lys Lys Lys Glu Lys Glu Arg Glu Glu Leu Trp Lys
                435                 440                 445

Lys Leu Glu Asp Leu Gly Leu Lys Arg Gly Leu Arg Arg Asp Gly Ile
450                 455                 460

Ile Pro Thr
465

<210> SEQ ID NO 9
<211> LENGTH: 206
<212> TYPE: PRT
<213> ORGANISM: Homo sapiens

<400> SEQUENCE: 9

Met Ala Ala Asn Lys Pro Lys Gly Gln Asn Ser Leu Ala Leu His Lys
1               5                   10                  15

Val Ile Met Val Gly Ser Gly Gly Val Gly Lys Ser Ala Leu Thr Leu
                20                  25                  30

Gln Phe Met Tyr Asp Glu Phe Val Glu Asp Tyr Glu Pro Thr Lys Ala
                35                  40                  45

Asp Ser Tyr Arg Lys Lys Val Val Leu Asp Gly Glu Glu Val Gln Ile
    50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Cys Val Phe Ser Ile Thr
                85                  90                  95

Glu Met Glu Ser Phe Ala Ala Thr Ala Asp Phe Arg Glu Gln Ile Leu
                100                 105                 110

Arg Val Lys Glu Asp Glu Asn Val Pro Phe Leu Leu Val Gly Asn Lys
            115                 120                 125

Ser Asp Leu Glu Asp Lys Arg Gln Val Ser Val Glu Glu Ala Lys Asn
    130                 135                 140

Arg Ala Glu Gln Trp Asn Val Asn Tyr Val Glu Thr Ser Ala Lys Thr
145                 150                 155                 160

Arg Ala Asn Val Asp Lys Val Phe Phe Asp Leu Met Arg Glu Ile Arg
                165                 170                 175

Ala Arg Lys Met Glu Asp Ser Lys Glu Lys Asn Gly Lys Lys Lys Arg
                180                 185                 190
```

Lys Ser Leu Ala Lys Arg Ile Arg Glu Arg Cys Cys Ile Leu
        195                 200                 205

<210> SEQ ID NO 10
<211> LENGTH: 2818
<212> TYPE: DNA
<213> ORGANISM: Homo sapiens

<400> SEQUENCE: 10

| | | | | | |
|---|---|---|---|---|---|
| aagtgatctg | tggcggctgc | tgcagagccg | ccaggaggag | ggtggatctc | cccagagcaa | 60 |
| agcgtcggag | tcctcctcct | ccttctcctc | ctcctcctcc | tcctcctcca | gccgcccagg | 120 |
| ctcccccgcc | acccgtcaga | ctcctccttc | gaccgctccc | ggcgcggggc | cttccaggcg | 180 |
| acaaggaccg | agtaccctcc | ggccggagcc | acgcagccgc | ggcttccgga | gccctcgggg | 240 |
| cggcggactg | gctcgcggtg | cagattcttc | ttaatccttt | ggtgaaaact | gagacacaaa | 300 |
| atggctgcaa | ataagcccaa | gggtcagaat | tctttggctt | tacacaaagt | catcatggtg | 360 |
| ggcagtggtg | gcgtgggcaa | gtcagctctg | actctacagt | tcatgtacga | tgagtttgtg | 420 |
| gaggactatg | agcctaccaa | agcagacagc | tatcggaaga | aggtagtgct | agatggggag | 480 |
| gaagtccaga | tcgatatctt | agatacagct | gggcaggagg | actacgctgc | aattagagac | 540 |
| aactacttcc | gaagtgggga | ggggttcctc | tgtgttttct | ctattacaga | aatggaatcc | 600 |
| tttgcagcta | cagctgactt | cagggagcag | attttaagag | taaagaagga | tgagaatgtt | 660 |
| ccatttctac | tggttggtaa | caaatcagat | ttagaagata | aagacaggt | ttctgtagaa | 720 |
| gaggcaaaaa | acagagctga | gcagtggaat | gttaactacg | tggaaacatc | tgctaaaaca | 780 |
| cgagctaatg | ttgacaaggt | atttttgat | ttaatgagag | aaattcgagc | gagaaagatg | 840 |
| gaagacagca | agaaaagaa | tggaaaaaag | aagaggaaaa | gtttagccaa | gagaatcaga | 900 |
| gaaagatgct | gcattttata | atcaaagccc | aaactccttt | cttatcttga | ccatactaat | 960 |
| aaatataatt | tataagcatt | gccattgaag | gcttaattga | ctgaaattac | tttaacattt | 1020 |
| tggaaattgt | tgtatatcac | taaaagcatg | aattggaact | gcaatgaaag | tcaaatttac | 1080 |
| tttaaaaga | aattaatatg | gcttcaccaa | gaagcaaagt | tcaacttatt | tcataattgc | 1140 |
| ctacatttat | catggtcctg | aatgtagcgt | gtaagcttgt | gtttcttggg | cagtcttttct | 1200 |
| tgaaattgaa | gaggtgaaat | ggggtgggg | agtgggagga | aagtgactt | cctctggtgt | 1260 |
| ttattataaa | gcttaaattt | tatatcattt | taaaatgtct | tggtcttcta | ctgccttgaa | 1320 |
| aaatgacaat | tgtgaacatg | atagttaaac | taccactttt | tttaaccatt | attatgcaaa | 1380 |
| atttagaaga | aaagttattg | gcatggttgt | tgcatatagt | taaactgaga | gtaattcatc | 1440 |
| tgtgaatctg | ctttaattac | ctggtgagta | acttagaaaa | gtggtgtaaa | cttgtacatg | 1500 |
| gaatttttg | aatatgccttt | aatttagaaa | ctgaaaaata | tctggttata | tcattctggg | 1560 |
| tgtgttctta | ctgacaccag | gggtccgctg | cccatgtgt | cctggtgaga | aaatatatgc | 1620 |
| ctggcacagc | ttttgtatag | aaaattcttg | agaagtaact | gtccgctaga | agtctgtcca | 1680 |
| aatttaaaat | gtgtgccata | ttctggttct | tgaaaataag | attccagagc | tctttgatcg | 1740 |
| cttttaataa | actgcaagtt | catttaaat | gaagggccag | catatatact | tgcaagataa | 1800 |
| ttttcagctg | caaggattca | gcaccagtta | tgtttgaatg | aaccctcctt | ttctctgaga | 1860 |
| ttctggtccc | tggaaatccc | tttctgctag | tggtgagcat | gtaagtgtta | agtttttaat | 1920 |
| ctgggagcag | ggcataggaa | gaaaatgtca | gtagtgctaa | tgcattttgc | actagaacgc | 1980 |
| ttcgggaaaa | tattcatgct | tgccatctgt | tcatttctaa | atttatattc | ataaagttac | 2040 |

```
agtttgatac aggaattatt aggagtaatt cttttctgtt tctgtttata atgaagaaca  2100
ctgtagctac attttcagaa gttaacatca agccatcaaa cctgggtata gtgcagaaaa  2160
cgtggcacac actgaccaca cattaggctg tgtcaccatt gtgtggtgta cctgctggaa  2220
gaattctagc atgctacttg gggacataat ttcagtggga aatatgccac tgaccgattt  2280
tttttttttc ctctttgcag tggggctagg acagttgatt caacaaagta ttttttttctt  2340 ttttctcagt cctaatttga acaggtcaaa gatgtgttca ggcattccag gtaacaggtg  2400
tgtatgtaaa gttaaaaata ggcttttttag gaactcactc tttagatatt tacatccagc  2460
ttctcatgtt aaatatttgt ccttaaaggg tttgagatgt acatctttca tttcgtattt  2520
ctcataggct atgccatgtg cggaattcaa gttaccaatg taacactggc cagcgggccc  2580
agcaatctcc atgtgtactt attacagtct tatttaacca ggggtcctaa ccactaacat  2640
tgtgactttg ctttgagacc tttcctctcc tgggtactga ggtgctatga agccaactga  2700
caaagatgca tcacgtgtct taggctgatg ccactacccg atttgtttat ttgcaatttg  2760
agccatttaa agaccaataa acttccttttt taaaaaaaa aaaaaaaaa aaaaaaa  2818
```

<210> SEQ ID NO 11
<211> LENGTH: 14
<212> TYPE: PRT
<213> ORGANISM: Artificial Sequence
<220> FEATURE:
<223> OTHER INFORMATION: Synthetically generated oligopeptide
<220> FEATURE:
<221> NAME/KEY: acetylation
<222> LOCATION: 1
<220> FEATURE:
<221> NAME/KEY: phosphorylation
<222> LOCATION: 9
<220> FEATURE:
<221> NAME/KEY: amidation
<222> LOCATION: 14

<400> SEQUENCE: 11

Cys Arg Ala Arg Lys Met Glu Asp Ser Lys Glu Lys Asn Gly
1               5                   10

<210> SEQ ID NO 12
<211> LENGTH: 13
<212> TYPE: PRT
<213> ORGANISM: Artificial
<220> FEATURE:
<223> OTHER INFORMATION: Synthetically generated oligopeptide
<220> FEATURE:
<221> NAME/KEY: acetylation
<222> LOCATION: 1
<220> FEATURE:
<221> NAME/KEY: phosphorylation
<222> LOCATION: 4
<220> FEATURE:
<221> NAME/KEY: amidation
<222> LOCATION: 13

<400> SEQUENCE: 12

Lys Arg Lys Ser Leu Ala Lys Arg Ile Arg Glu Arg Cys
1               5                   10

<210> SEQ ID NO 13
<211> LENGTH: 6
<212> TYPE: PRT
<213> ORGANISM: Artificial Sequence
<220> FEATURE:
<223> OTHER INFORMATION: synthetically generated oligopeptide

<400> SEQUENCE: 13

```
Thr Ile Ala Leu Ala Leu
1               5
```

```
<210> SEQ ID NO 14
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 14
caacaattgc cctagcactt g                                              21

<210> SEQ ID NO 15
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 15
caacaatagc gcttgcgctt g                                              21
```